United States Patent [19]
Toda et al.

[11] Patent Number: 4,847,275
[45] Date of Patent: Jul. 11, 1989

[54] (FUSED) BENZ (THIO) AMIDES

[75] Inventors: Masaaki Toda, Mishima; Tumoru Miyamoto, Johyoh; Yoshinobu Arai, Mishima, all of Japan

[73] Assignee: Ono Pharmaceutical Co., Ltd., Japan

[21] Appl. No.: 207,994

[22] Filed: Jun. 17, 1988

Related U.S. Application Data

[62] Division of Ser. No. 767,538, Aug. 20, 1985, Pat. No. 4,780,469.

[30] Foreign Application Priority Data

Aug. 20, 1984 [JP] Japan .............................. 59-172570
Dec. 20, 1984 [JP] Japan .............................. 59-243412
Dec. 22, 1984 [JP] Japan .............................. 59-246363

[51] Int. Cl.⁴ ................ A61K 31/335; A61K 31/385; C07D 319/16; C07D 339/08
[52] U.S. Cl. ..................... 514/382; 514/434; 514/452; 548/253; 549/15; 549/362
[58] Field of Search ................ 548/253; 549/15, 362; 514/382, 434, 452

[56] References Cited

U.S. PATENT DOCUMENTS 4,205,076 5/1980 Durham et al. .................. 514/365
4,205,079 5/1980 Durham et al. .................. 514/365

Primary Examiner—Richard L. Raymond
Attorney, Agent, or Firm—Sughrue, Mion, Zinn, Macpeak, and Seas

[57] ABSTRACT

A (fused) benz (thio) amide of the general formula:

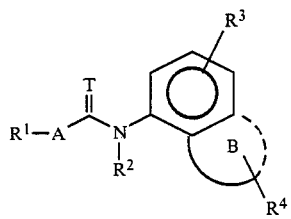

(wherein, symbol A represents a single bond or a group of methylene, ethylene, trimethylene, tetramethylene, vinylene, propenylene, butenylene, butadienylene or ethynylene group optionally being substituted by one, two or three of straight or branched alkyl group(s) of from 1 to 10 carbon atom(s) and/or phenyl group(s);
B represents a group of the general formula:

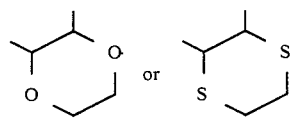

T represents an oxygen atom or a sulphur atom;
$R^1$ represents a group of general formula:

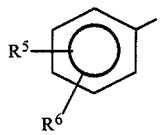

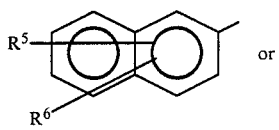

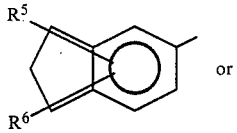

(iv) a straight or branched alkyl, alkenyl or alkynyl group of from 1 to 20 carbon atom(s);
(wherein $R^5$ and $R^6$ independently represent a hydrogen atom or a halogen atom or a straight or branched alkyl, alkenyl or alkynyl group of from 1 to 20 carbon atom(s) being unreplaced or replaced one, two, three, four or five of optional carbon atom(s) by oxygen atom(s), sulphur atom(s), halogen atom(s), nitrogen atom(s), benzene ring(s), thiophene ring(s), naphthalene ring(s), carbocyclic ring(s) of from 4 to 7 carbon atom(s), carbonyl group(s), carbonyloxy group(s), hydroxy group(s), carboxy group(s), azido group(s) and/or nitro group(s));
$R^2$ represents a hydrogen atom or a straight or branched alkyl group of from 1 to 6 carbon atom(s);
$R^3$ represents a hydrogen atom, a halogen atom, a hydroxy group, a nitro group, a group of general formula: —COOR⁷ (wherein $R^7$ represents a hydrogen atom or a straight or branched alkyl group of from 1 to 6 carbon atom(s).) or a straight or branched alkyl, alkoxy or alkylthio group of from 1 to 6 carbon atom(s).
$R^4$ represents
(i) when symbol B represents a closed ring, a group of general formula:

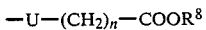

—U—(CH₂)ₙ—COOR⁸

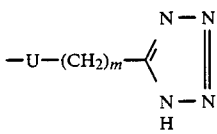

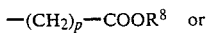

—(CH₂)ₚ—COOR⁸ or (Abstract continued on next page.)

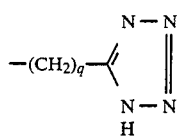

(wherein symbol U represents an oxygen atom or a sulphur atom. $R^8$ represents a hydrogen atom or a straight or branched alkyl group of from 1 to 6 carbon atom(s). n and m represent an integer of from 1 to 10, respectively, p and q represent zero or an integer of from 1 to 10, respectively;)

or non-toxic salts thereof possess an antagonistic activity on leukotrienes (SRS), inhibitory activity on 5α-reductase, on phospholipase and on aldose reductase and are therefore useful for the prevention and/or treatment for diseases induced by leukotrienes, 5α-reductase, phospholipase and aldose reductase in mammals, especially human beings.

77 Claims, No Drawings

(FUSED) BENZ (THIO) AMIDES

This is a division of application Ser. No. 06/767,538, filed Aug. 20, 1985, now U.S. Pat. No. 4,780,469.

SUMMARY

This invention is related to novel benz(thio)amides.

More particularly, this invention is related to novel (fused) benz(thio)amides having an antagonistic activity on leukotrienes (SRS) and an inhibitory activity on 5α-Reductase; processes for the preparation of them; and pharmaceutical agent containing them as active ingredient.

BACKGROUND

In the study of prostaglandins (abbreviated as PG hereafter), many important discoveries have been made continuously in recent years. And so it was found a large change in the direction of the research and development of PG. In the compounds which have been newly found or newly confirmed their structure in PG family, it can be said that PG endoperoxides, (i.e. $PGG_2$ and $PGH_2$), thromboxane $A_2$ (abbreviated as $TXA_2$ hereafter), prostacyclin (i.e. $PGI_2$) and leukotriene $C_4$, $D_4$ and $E_4$ (abbreviated as $LTC_4$, $LTD_4$ and $LTE_4$, respectively, hereafter) etc. have especially strong and unique biological activities.

All the compounds of PG family containing various PG previously known well in addition to the above compounds, are biosynthesized from the same mother compound, i.e. arachidonic acid in a living body and, therefore, the metabolic routes starting from arachidonic acid is called "Arachidonate cascade" as a whole. The detailed explanation of each route and the pharamcological character of each metabolite are described in Igaku No Ayumi, 114, 378 (1980), ibid, 114, 462 (1980), ibid, 114, 866 (1980), ibid, 114, 929 (1980), Gendai Iryo, 12, 909 (1980), ibid, 12, 1029 (1980), ibid, 12, 1065 (1980) and ibid, 12, 1105 (1980) etc.

The arachidonate cascade can be largely divided into two routes; one is the route that cyclooxygenase acts on arachidonic acid to convert, into various PGs, e.g. prostaglandin $F_2$ (abbreviated $PGF_2$ hereafter), prostaglandin $E_2$ (abbreviated $PGE_2$ hereafter), $PGI_2$, $TXA_2$, via $PGG_2$ and further $PGH_2$ and the other is the route that lipoxygenase acts on arachidonic acid to convert, in hydroxyeicosatetraenoic acid (abbreviated as HETE hereafter) or leukotrienes, via hydroperoxyeicosatetraenoic acid (abbreviated HPETE hereafter).

As the former route is well known, it is not described in the present specification in detail. See Prostaglandin (1978), edited by Makoto Katori et al., published by Kohdan-sha.

Concerning the latter route, it has been known that various compounds are produced according to the following scheme I.

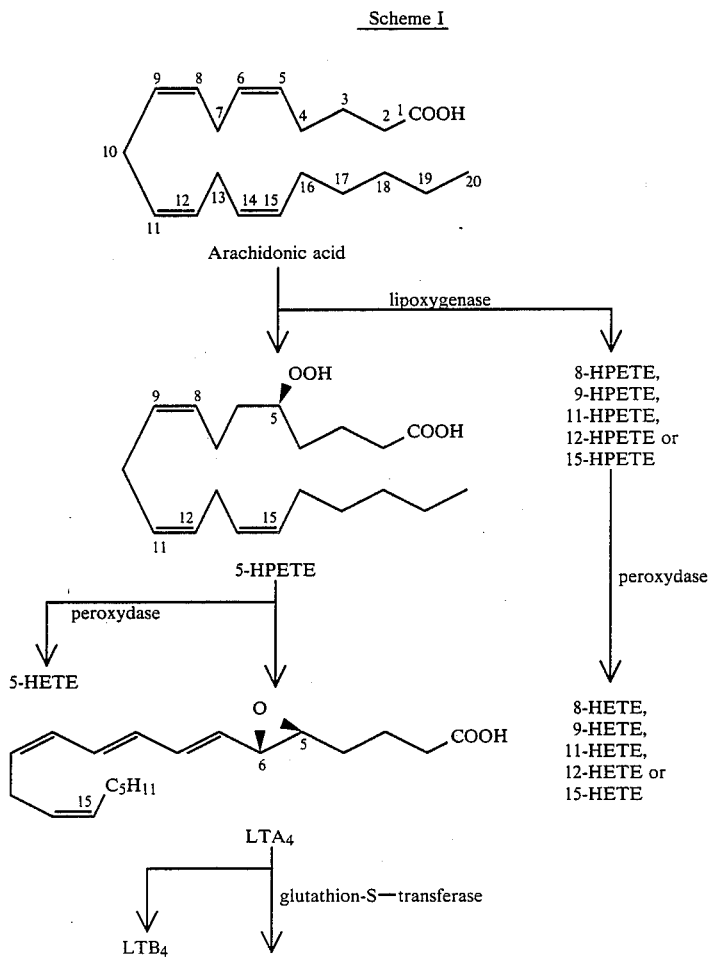

Scheme I

Scheme I -continued

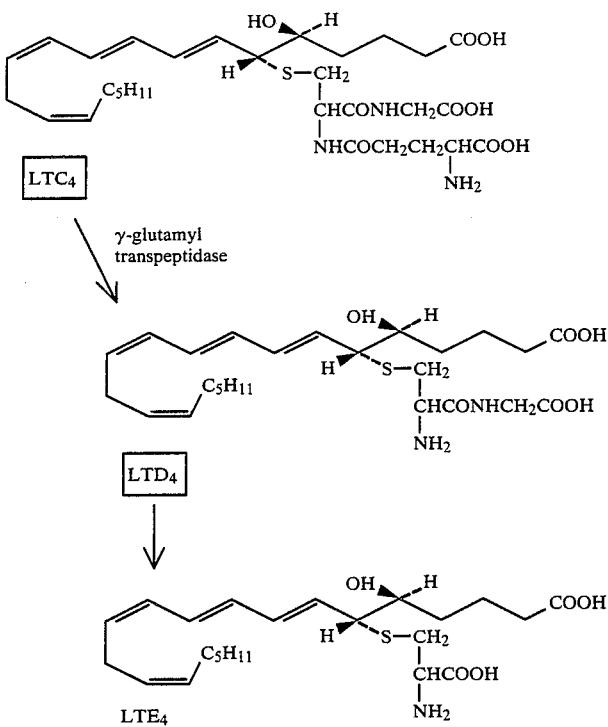

LTC4

γ-glutamyl transpeptidase

LTD4

LTE4

Besides being metablized through a well known route, i.e. the route via PG endoperoxides, arachidonic acid is also metabolized through another route by the action of lipoxygenase. That is to say, arachidonic acid is metabolized by the action of lipoxygenase, e.g. 5-lipoxygenase, 12-lipoxygase and 15-lipoxygenase, to 5-HPETE, 12-HPETE and 15-HPETE, respectively.

These HPETE are converted into 5-HPETE, 12-HPETE and 15-HPETE, respectively, by the action of peroxidase converting a hydroperoxy group into a hydroxy group. Furthermore, LTA4 is also produced from 5-HPETE by dehydration. LTA4 is converted into leukotriene B4 (abbreviated as LTB4 hereafter) or LTC4 enzymatically. Further, LTC4 is converted into LTD4 by the action of γ-glutamyl transpeptidase.

Moreover, it was recently defined that LTD4 is metabolized to LTE4 (see Biochem. Biophys. Res. Commun., 91, 1266 (1979) and Prostaglandins, 19(5), 645 (1980)).

Besides, SRS is an abbreviation of Slow Reacting Substance and it was named by Feldberg et al. for the substance released when perfusing cobra venom through isolated lung or incubating cobra venom with vitellus. And it was reported that the substance constricted ilem isolated from guinea pig slowly and continuously (see J. Physiol., 94, 187 (1938)).

Moreover, Kellaway et. al showed the relation between SRS-A and allergic reaction from the fact that SRS-A is released when antigen is sensitized to perfusing lung isolated from guinea pig (see Quant. J. Exp. Physiol., 30, 121 (1940)).

Brocklehurst reported that when the antigen is sensitized to a lung fragment isolated from a bronchial asthmatics whose specific antigen is defined, by an operation, histamine and SRS-A are released and strongly constrict bronchial muscle. Since such constriction can not be prevented by an antihistatinic agent, he suggested that SRS-A is an important bronchoconstrictor in an asthmatic paroxysm (see Progr. Allergy, 6, 539 (1962)).

Since then, many reports were published, for instance, SRS-A prepared from human lung slice constrict a tracheal spiral of normal human (see Int. Arch. Allergy Appl. Immunol., 38, 217 (1970)); when SRS-A prepared from rats is injected intravenously to guinea pig, significant increase of pulmonary resistance is observed (see J. Clin. Invest., 53, 1679 (1974)); in addition, a subcutaneous injection of SRS-A to guinea pig, rat and monkey enhances vscular permeability (see advances in Immunology, 10, 105 (1969). J. Allergy Clin. Immunol., 621, 371 (1978), Prostaglandins, 19(5), 779 (1980) etc. ).

Generally, the substance released by immunological reaction is called SRS-A. On the other hand, the substance released by non-immunological reaction such as calcium inonophore is called SRS. However, the above two substances have many similarities to each other and, therefore, it is considered they would probably be the same substance.

Further, it was confirmed that SRS or SRS-A is a mixture of LTLC4 and LTD4. So it can be udnerstood that the pharmacological characters of these leukotrienes are the same as those of SRS or sRS-A (see Proc. Natl. Acad. Sci. USA, 767, 4275 (1979), Biochem. Biophys. Res. Commun., 91, 1266 (1979), Proc. Natl. Acad. Sci. USA, 77, 2014 (1980) and Nature, 285, 104 (1980)).

Based on the results of thse studies, various leukotrienes (the structures of LTC4, LTD4 and LTE4, and further other leukotrienes which may be confirmed in the future) biosynthesized from arachidonic acid via LTA4, are considered to be important factors relating to the appearance of allergic tracheal and bronchial diseases, allergic lung diseases, allergic shock and various allergic inflammations.

To surpress leukotrienes is useful for the prevention and/or treatment of tracheal bronchial or lung diseases such as asthma, allergic lung diseases, allergic shock or various allergic diseases.

On the other hand, arachidonic acid is released from phosphoslipids by the action of phospholipase, and two routes were generally accepted that (1) one is the route that phospholipase $A_2$ is reacted on phosphatidyl choline, and (2) the other is the route that phospholipase C was reacted on phosphatidyl inositol to produce 1,2-diglyceride, and diglyceridelipase followed by monoglycerdielipase were reacted on it to release arachidonic acid (see Kagaku to Seibutsu (Chemistry and Biology, 21, 154 (1983)).

And it was known that arachidonic acid released is metabolized through two different routes i.e. (1) metabolizing route to bioactive substances e.g. prostaglandins (PGs), thromboxane $A_2$ (TXA$_2$) by cyclooxygenase, and (2) metabolizing route to bioactive substances e.g. SRS-A (Slow Reacting Substances of Anaphylaxis), hydroxyeicosatetraenoic acid (HETE) and leukotriene $B_4$ (LTB$_4$) by lipoxygenase (see Kagaku to Seibutsu (Chemistry and Biology), 21, 154 (1983)).

These metabolites are known as chemical mediators; for example, TXA$_2$ is a compound which have a potent activity of platelet aggregation and aotra contraction, SRS-A is a chemical mediator on asthma, LTB$_4$ is a chemical mediator on various inflammations (e.g. gout), and PGs are also chemical mediators on various inflammations which enhance a vascular permeability and a pain, and have a vasodilative action, pyrogenetic action and chemotactic action (see Prostaglanin (1978), edited by Makoto Katori et al, published by Kohdan-sha).

Arachidonic acid is converted and metabolized to various chemical mediators which act important physioloical part in living body. And it was known that illbalances of those chemical mediators induce various disorders.

And as antagonist of SRS, the groups of the compounds of general formula:

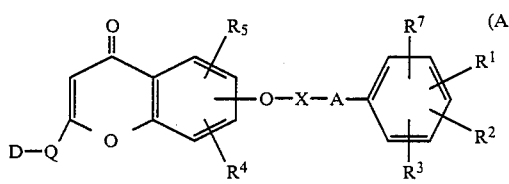

(wherein from $R^1$ to $R^5$ and $R^7$ each represent a hydrogen atom, a hydroxy group, an alkyl group of from 1 to 6 carbon atom(s), an alkoxy group of from 1 to 6 carbon atom(s), an amino group, an acyl group, an acylamino group of from 2 to 6 carbon atoms, an alkenyl group of from 2 to 6 carbon atoms, a halogen atom or a phenylalkoxy group in which alkoxy have from 1 to 6 carbon atom(s); X representsa hydrocarbyl group of from 1 to 10 carbon atom(s) being optionally substituted by hydroxy group(s); A represents an oxygen atom or is absent; Q represents an alikylene, alkenylene or alkynylene group of from 2 to 6 carbon atoms which may be branched; D represents a carboxy group, a 5-tetrazolyl group or carbamido-5-tetrazolyl group) were described in the patent publication by Fisons Co., Ltd. (see Japanese Patent Application No. 55-1273841 i.e. European Patent Publication No. 17332 or U.S. Pat. No. 4,281,008).

And, the following compounds were discribed in the patent publication by Kissei Pharmaceutical Co., Ltd. as anti-allergic agent, of the general formula:

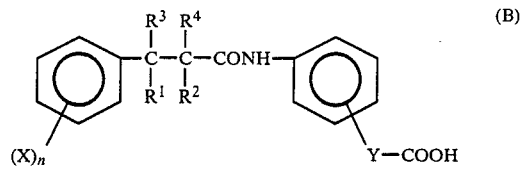

(wherein $R^1$ and $R^2$ each represent a hydrogen atom or an alkyl group with 1-4 carbon atoms; $R^3$ and $R^4$ each represent a hydrogen atom or may be combined together to form an additional chemical bond; X represents a hydroxyl group, a halogen atom, a straight or branched chain saturated or unsaturated alkyl group with 1-4 carbon atoms, a straight or branched chain saturated or unsaturated alkoxy group with 1-4 carbon atoms, an acyloxy group with 1-4 carbon atoms, or a cycloalkyl group with up to 6 carbon atome; n is zero or an integer of 1-3 with the proviso that when n is 2 or 3; X's may be the same or different and that when two X's are commonly the alkyl or alkoxy group, both X's may be combined together to form a ring; and Y represents a straight or branched chain alkylene group or a straight or branched chain oxyalkylene group connected to the benzene nucleus through an oxygen atom;)

as well as physioloically acceptable salts thereof. (see U.S. Pat. No. 4,026,896.)

And benzamides. i.e. compounds represented by the general formula (I) depicted hereafter, wherein the symbol B is opened and $R^4$ is a group of the formula: —OCH$_2$COOR, were described in the prior patent application by the present inventors. (see Japanese Patent Application Kokai Nos. 60-97946, 60-116657, 60-142941 and 60-146855.)

DISCLOSURE OF THE INVENTION

The present inventors have synthesized novel compounds of the general formula (I) depicted hereafter, which have a structure characterized as a (thio)amido group being substituted on a fused benzene ring or benzene ring and have found the compounds have potent antagonistic activity on leukotrienes (SRS), and then achieved the present invention.

And, the compounds of the present invention also inhibit phospholipase, so inhibit release of arachidonic acid from phospholipids, and therefore are useful for prevention and/or treatment of diseases induced by arachidonate metabolites e.g. TXA$_2$, PGs, leukotrienes in mammals including human beings, especially human beings.

Examples of the diseases to the subject are various allergic diseases induced by leukotrienes described above, thrombosis e.g. one induced by injury (damage) of cerebral or coronary, endothelium or intima and inflammations e.g. arthritis, rheumatism (see Junkan Kagaku (Cardiovascular science) 3, 484 (1983) Yakkyoku (Pharmacy) 34, 167 (1983)).

It was found that the compounds of the present invention also have an inhibitory activity on 5α-reductase described below, besides the activity of leukotriene antagonist and phospholipase inhibitor above.

5α-Reductase presents in endoplasmic reticulum and nucleic acid, and it converts testosterone which is taken into a target tissue, into active 5α-dihydrotestosterone. The activated 5α-dihydrotestosterone induces cell proliferaction by binding to an intracelluar receptor. Activation of this enzyme is considered to cause some diseases such as prostatic hypertrophy, make resulting in pattern baldness and acne.

As a matter of course, the compounds of the present invention have no activity peculiar like hormones, and inhibit 5α-reductase, so suppress increasing of 5α-dihydrotestosterone, therefore, suppress cell proliferaction, and therefore are useful for the prevention and/or treatment of prostatic hypertrophy, male pattern baldness and acne in mammals including human beings especially human beings.

Furthermore, it was found that the compounds of the present invention also have an inhibitory activity on aldose reductases.

An aldose reductase is an enzyme which reduces an aldose (e.g. glucose, galactose) into the corresponding polyol (e.g. sorbitol, galactitol) in human beings or other animals. The sorbitol and galactitol produced by the action of this enzyme are accumulated in the crystalloine lenses, the peripheral nerves, the kidney, etc. of diabetics including galactosemiacs thus causing the above described complications e.g. retinopathy, diabetic cataract, nerve disturbances or renal disorders (see Jap. J. Opthamol., 20, 399 (1976), Int. Congr. Ser. Excepta Med., 403, 594 (1977) and Metabolism, 28,456 (1979)).

The compounds of the present invention have inhibitory activity on an aldose reductase and are therefore effective for the prevention and/or treatment of diabetic complications described above in mammals including human beings especially human beings.

That is the present invention relates to novel (fused) benz(thio)amides of the general formula:

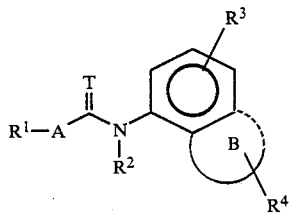
(I)

(wherein, A represents a single bond or a group of methylene, ethylene, trimethylene, tetramethylene, vinylene, propenylene, butenylene, butadienylene or ethylnylene group optionally being substituted by one, two or three of straight or branched alkyl group(s) of from 1 to 10 carbon atom(s) and/or phenyl group(s);

B represents (i) a carbocyclic ring of from 4 to 8 members being unreplaced or replaced one, two or three of optional carbon atom(s) by oxygen, nitrogen and/or sulphur atom(s) (the ring may optionally be substituted by group(s) of oxo, thioxo and/or hydroxy group(s)) or (ii) a divalent group of formula:

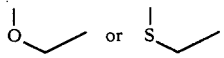

T represents an oxygen atom or a sulphur atom;

$R^1$ represents a group of general formula:

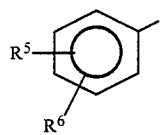
(i)

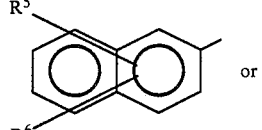
(ii)

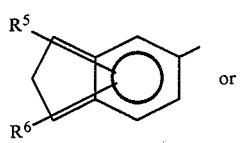
(iii)

(iv) a straight or branched alkyl, alkenyl or alkynyl group of up to 20 cabon atom(s);

(wherein $R^5$ and $R^6$ independently represent a hydrogen atom or a halogen atom or a straight or branched alkyl, alkenyl or alknynyl group of up to 20 carbon atom(s) unreplaced or replaced one, two, three, four or five of optional carbon atom(s) by oxygen atom(s), sulphur atom(s), halogen atom(s), nitrogen atom(s), benzene ring(s), thiophene ring(s), naphthalene rings), carbocyclic ring(s) of from 4 to 7 carbon atom(s), carbonyl group(s), carbonyloxy group(s), hydroxy group(s), carboxy group(s), azido group(s) and/or nitro group(s));

$R^2$ represents a hydrogen atom or a straight or branched alkyl group of from 1 to 6 carbon atom(s);

$R^3$ represents a hydrogen atom, a halogen atom, a hydroxy group, a nitro group, a group of general formula: —COOR$^7$ (wherein $R^7$ represents a hydrogen atom or a straight or branched alkyl group of from 1 to 6 carbon atom(s)) or a straight or branched alkyl, alkoxy or alkylthio group of from 1 to 6 carbon atom(s);

$R^4$ represents (i) when B represents a closed ring, a group of general formula:

—U—(CH$_2$)$_n$—COOR$^8$

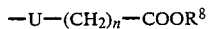

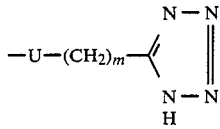

—(CH$_2$)$_p$—COOR$^8$  or

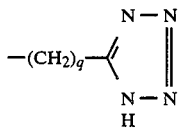

(wherein U represents an oxygen atom or a sulphur atom; $R^8$ represents a hydrogen atom or a straight or branched alkyl group of from 1 to 6 carbon atom(s), n and m represent an integer of from 1 to 10, respectively, p and q represent zero or an integer of from 1 to 10, respectively) or (ii) when B do not represent a ring, a group of general formula:

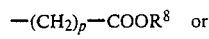

or

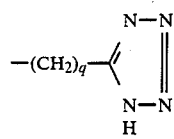

(wherein $R^8$, p and q represent the same meaning as depicted hereinbefore, with the proviso that, when B represents a group of formula:

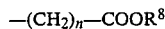

p does not represent zero,
with the proviso that, following compounds are excluded, i.e. compounds of general formula:

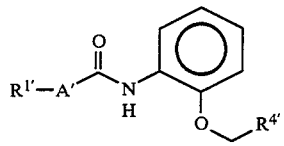

(I')

(wherein A' is a vinylene or ethylene group optionally being substituted by straight or branched alkyl group(s) of from 1 to 4 carbon atom(s), $R^{4'}$ is the general formula:

$$-(CH_2)_n-COOR^8$$

wherein $R^8$ and n are defined the same as hereinbefore, and $R^{1'}$ is
(i) a group of the general formula:

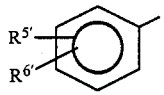

(wherein $R^{5'}$ and $R^{6'}$ are hydrogen atom(s), hydroxy group(s), halogen atom(s), straight or branched alkyl, alkenyl, alkynyl, alkoxy, alkenyloxy, alkynyloxy or acyloxy group(s) of up to 4 carbon atoms(s) or cycloalkyl group(s) of from 3 to 6 carbon atom(s), independently or
(ii) a group of the generalky formula:

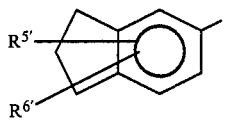

(wherein $R^{5'}$ and $R^{6'}$ are the same meaning as depicted hereinbefore))

and non-toxic salts thereof, and processes for their preparation, and pharmaceutical agents including them or it as active ingredient.

The compounds of the present invention may be largely divided into the following two groups in accordance with whether B is a closed ring or not.
That is the present invention includes compounds of the general formula:

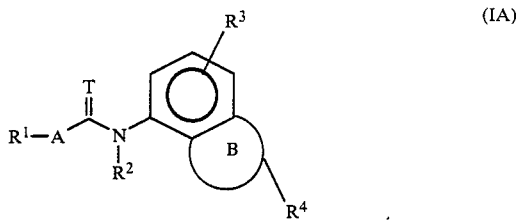

(IA)

and

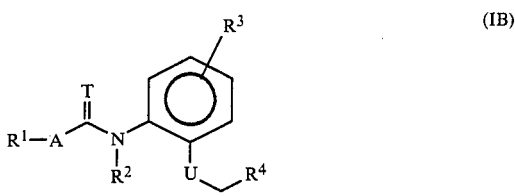

(IB)

wherein A, B, $R^1$, $R^2$, $R^3$, $R^4$, T and U have the same meaning as described hereinbefore.

Both of the compounds of the general formula (IA) and (IB) are novel compounds per se.

The compounds of the general formula (IA) are quite novel, in chemical structure, because they have a (thi-o)amido group as well as benzene ring(s) and/or chromone skeleton as the essential group, compared with the compounds of Fisons of the general formula (A), described hereinbefore in the part of background.

The compounds of the general formula (IB) are also novel compounds and have been first found to have inhibitory activities on 5α-reductase, on lipoxygenase and on aldose reductase, besides antagonistic activity on leukotrienes.

In the general formula (I), examples of the groups represented by $R^5$ and $R^6$ are the following:
a hydrogen atom, a halogen atom
an alkyl group of from 1 to 20 carbon atom(s)
an alkenyl or alkynyl group of from 2 to 20 carbon atoms
an alkoxy or alkylthio group of from 1 to 19 carbon atom(s)
an alkenyloxy, alkenylthio, alkynyloxy or alknylthio group of from 3 to 19 carbon atoms
an alkyl group of from 1 to 19 carbon atoms(s) substituted by halogen atom(s) and/or hydroxy group(s)
an alkenyl or alkynyl group of from 2 to 9 carbon atoms substituted by halogen atom(s) and/or hydroxy group(s)
an alkoxy or alkylthio group of from 1 to 18 carbon atom(s) substituted by halogen atom(s) and/or hydroxy group(s)
an alkenyloxy, alkenylthio, alkynylthio or alkynyloxy group of from 3 to 18 carbon atoms substituted by halogen atom(s) and/or hydroxy group(s)
an alkyloxyalkyl, alkenyloxyalkyl or alkyloxyalkenyl group of up to 19 carbon atoms
a cycloalkyl, cycloalkyloxy or cycloalkylthio group of from 4 to 7 carbon atoms
a phenyl, phenoxy or phenylthio group an alkyl group of from 1 to 19 carbon atom(s) which has carbocyclic ring(s) of from 4 to 7 carbon atoms, benzene ring(s), naphthalene ring(s) or thiophene ring(s) in the middle or at the terminal thereof an alkoxy, alkylthio, alkenyloxy, alkenylthio, alkynyloxy or alkynylthio group of up to 18 carbon atom(s) which have carbocyclic ring(s) of from 4 to 7 carbon atoms, benzene ring(s), naphthalene ring(s) or thiophene ring(s) in the middle or at the terminal thereof a phenylthioalkoxy or phenyloxyalkyloxy group wherein the alkyl moiety is a group from 1 to 17 carbon atom(s)

a carboxyalkyloxy alkoxycarbonylalkyloxy group of up to 9 carbon atoms an alkoxycarbonyloxyalkyloxy group of from 3 to 19 carbon atoms an alkenylcarbonyloxy group of from 3 to 20 carbon atoms an alkylcarbonyl group of from 2 to 20 carbon atoms an azidoalkyl, nitroalkyl, aminoalkyl, alkylaminoalkyl, dialkylaminoalkyl group of up to 19 carbon atom(s)

an azidoalkyloxy, nitroalkyloxy, aminoalkyloxy, alkylaminoalkyloxy, dialkylaminoalkyloxy group of up to 18 carbon atom(s)

an alkenylcarbonylamino group of from 3 to 9 carbon atoms an alkylamino group of from 1 to 19 carbon atom(s)

groups described above further substituted by halogen atom(s), hydroxy group(s), azido group(s), nitro group(s) and/or carboxy group(s)

Among the groups described above, preferable groups as $R^5$ and $R^6$ are the following groups:

a hydrogen atom a halogen atom a straight or branched alkyl group of from 1 to 20 carbon atom(s)

a straight or branched alkoxy group of from 1 to 19 carbon atom(s)

a straight or branched alkenyloxy group of from 3 to 19 carbon atoms a straight or branched alkynyloxy group of from 3 to 19 carbon atoms a straight or branched alkylthio group of from 1 to 19 carbon atom(s)

a straight or branched alkyl group of from 1 to 18 carbon atom(s) being substituted by halogen atom(s)

a straight or branched alkyloxyalkyl group of from 2 to 19 carbon atom(s)

a cycloalkyl, cycloalkylalkyl (wherein alkyl moiety is a group of from 1 to 8 carbon atom(s)) or cycloalkylalkyloxy (wherein alkyl moiety is a group of from 1 to 8 carbon atom(s)) group optionally substituted by straight or branched alkyl group(s) of from 1 to 8 carbon atom(s), hydroxy group(s), halogen atom(s) and/or nitro group(s)

a phenyl, phenylalkyl (wherein alkyl moiety is a group of from 1 to 8 carbon atoms(s)), phenylalkyloxy (wherein alkyl moiety is a group of from 1 to 8 carbon atom(s)) or phenylalkenyloxy (wherein alkenyl moiety is a group of from 2 to 8 carbon atoms(s)) group optionally substituted by straight or branched alkyl group(s) of from 1 to 8 carbon atom(s), hydroxy group(s), halogen atom(s) and/or nitro group(s)

an naphthyl, napthylalkyl (wherein alkyl moiety is a group from 1 to 8 carbon atoms(s), naphthylalkoxy (wherein alkyl moiety is a group from 1 to 8 carbon atom(s)) or naphthylalkenyloxy (wherein alkenyl moiety is a group from 2 to 8 carbon atoms) group optionally substituted by straight or branched alkyl group(s), hydroxy group, halogen atom(s) and/or nitro group(s)

a straight or branched alkoxy, alkenyloxy or alkyloxyalkyloxy group of up to 18 carbon atom(s) substituted by carbonyl, carbonyloxy and/or hydroxy group(s)

a straight or branched alkoxy group of from 1 to 17 carbon atom(s) substituted by phenoxy or phenylthio group(s)

a straight or branched alkoxy group of from 1 to 18 carbon atom(s) substituted by thiophene ring(s)

a straight or branched alkyl, alkenyl, alkoxy or alkenyloxy group of up to 18 carbon atom(s) substituted by azido or nitro group(s) or amino group(s) optionally substituted by an alkyl group of from 1 to 6 carbon atom(s) (including dialkylamino group(s))

a straight or branched alkyl, alkenyl, alkoxy or alkenyloxy group of up to 18 carbon atom(s) replaced by two kinds groups which are carbonyl groups(s) and amino group(s)

An alkyl group of from 1 to 20 carbon atom(s) in the present invention means a group of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicocyl group and an isomeric group thereof.

And an alkenyl and alkynyl group of from 2 to 20 carbon atom(s) mean corresponding groups described above.

An alkyl group of from 1 to 6 carbon atom(s) in the present invention means a methyl, ethyl, propyl, butyl, pentyl, or hexyl group, or an isomeric group thereof.

A cycloalkyl group of from 4 to 7 carbon atoms in the present invention means a cyclobutyl, cyclopentyl, cyclohexyl or cycloheptyl group.

A halogen atom in the present invention means a chlorine, bromine, iodine or fluorine atom.

In the present invention, when a certain carbon atom is replaced by another atom, a ring or a group, any carbon atom(s) can be replaced, so far as the replacement per se can be acceptable chemically or physically. For example, "an isobutyl group replaced by a benzene ring in the middle or at the terminal" means a isopropylphenyl, dimethylphenylmethyl or 2-phenylpropyl group. When a carbon atom is replaced, hydrogen atom(s) may be added or removed suitably. For example, "a pentyl group replaced by a nitrogen atom at the 2nd position" means N-propylaminomethyl group.

And, for example, 2-(phenoxy)ethoxy group and 5-(2-chloro-4-nitrophenylthio)-5-methylpent-2-enyloxy groups are replaced one, two, three, four or five of optional carbon atom(s) from pentyl group and 6,8-dimethylnon-3-enyl group, respectively, and therefore they are included in the present invention.

These examples are merely illustrative and should not be construed as limiting upon the scope of the present invention.

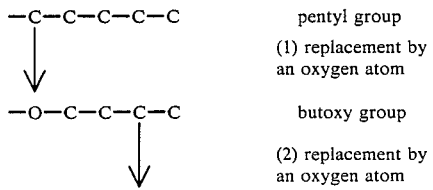

-continued

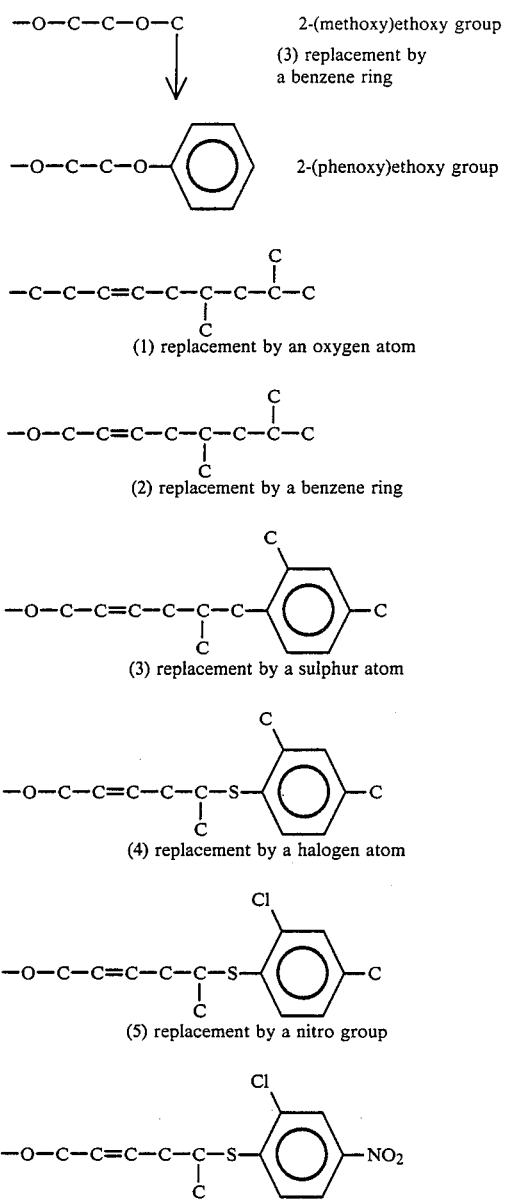

(3) replacement by a benzene ring 2-(phenoxy)ethoxy group (1) replacement by an oxygen atom (2) replacement by a benzene ring (3) replacement by a sulphur atom (4) replacement by a halogen atom (5) replacement by a nitro group And examples of carbocyclic rings of from 4 to 8 members being unreplaced or replaced one, two or three of optional carbon atom by oxygen, nitrogen and/or sulphur atom(s) (the ring may optionally be substituted by group(s) of oxo, thioxo and/or hydroxy group(s)) represented by B in the general formula (I) are the following:

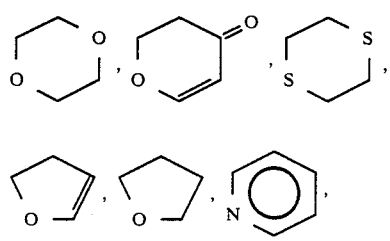

-continued

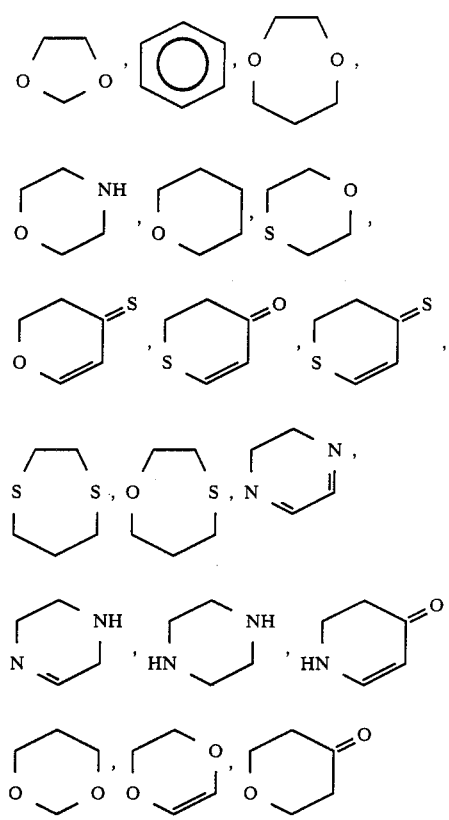

(The rings above described may optionally be substituted by hydroxy group(s))

The carbocyclic rings depicted above may be saturated rings or unsaturated ones, or aromatic rings or non-aromatic ones.

Any rings depicted above are preferable. And, when the rings are fused with benzene rings, the following fused benzene rings are especially preferable, i.e. the rings of the general formula

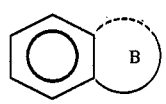

are the following rings:

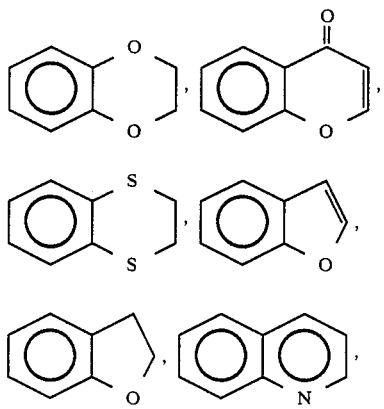

-continued

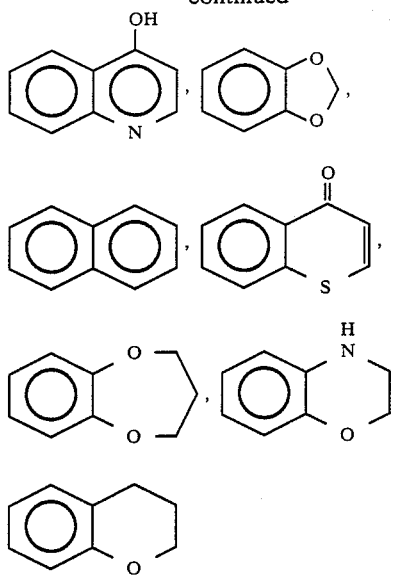

And compounds wherein B is a opened group of the formula:

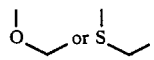

are also preferable.

Process for the Preparation (1)

The present invention includes not only the compounds per se, non-toxic salts thereof, use or method, but also process for the preparation.

According to the present invention, the compounds of the present invention of the general formula (I) may be prepared by reacting a compound of general formula:

$$R^1-A-COOH \quad (II)$$

(wherein $R^1$ and A have the same meaning as described hereinbefore)
or a corresponding dithioic acid and a compound of general formula:

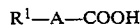

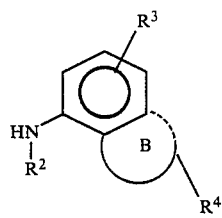

(wherein B, $R^2$, $R^3$ and $R^4$ have the same meaning as described hereinbefore)
to form amide-bond, and further subjecting the product thereof to saponification or and/or esterification, if desired.

Reactions to form amide-bond are well known, it may be carried out, for example;
(A) by the method with using mixed acid anhydride
(B) by the method with using acid halide
(C) by the method with using DCC (Dicyclohexylcarbodiimide)

Concrete description of the methods described above are as follows:

(A) method with using mixed acid anhydride may be carried out, for example; an acid of the general formula (II) is reacted with an acid halide (pivaloyl chloride, thionyl chloride, tosyl chloride, mesyl chloride, oxalyl chloride etc.) or an acid derivative (ethyl chloroformate, isobutyl chloroformate etc.) in an inert organic solvent (chloroform, methylene chloride, diethyl ether, THF etc.) or without solvents, in the presence of tertiary amine (pyridine, triethylamine, picoline etc.), at from 0° C. to 40° C. to give a mixed acid anhydride. The obtained acid mixed anhydride and an amine of the general formula (III) are reacted in an inert organic solvent (described above), at from 0° C. to 40° C.

(B) method with using acid halide may be carried out, for example; an acid of the general formula (II) is reacted with an acid halide (described above) in an inert organic solvent (described above) or without solvents at from −20° C. to a refluxing temperature of the solvent used to give an acid halide. The obtained acid halide and an amine of the general formula (III) are reacted in an inert organic solvent (described above) in the presence or absence of tertiary amine (described above) at from 0° C. to 40° C.

(C) method with using DCC may be carried out, for example; an acid of the general formula (II) and an amine of the general formula (III) are reacted in an inert organic solvent (described above) or without solvents in the presence or absence of tertiary amine (described above) using with DCC at from 0° C. to 40° C.

Preferably, the reactions (A), (B) and (C) described above are carried out in an atmosphere of inert gas (argon, nitrogen, etc.) under anhydrous conditions.

Process for the Preparation (2)

Among the compounds of the present invention, compounds of the general formula:

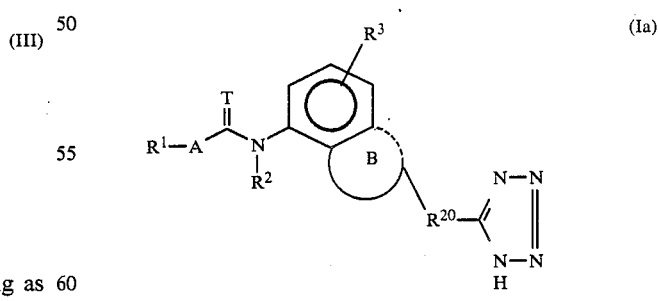

(wherein $R^{20}$ represents methylene group or a single bond, and A, B, $R^1$, $R^2$, $R^3$ and T have the same meaning as described hereinbefore)

may be prepared by reacting a compound of the general formula:

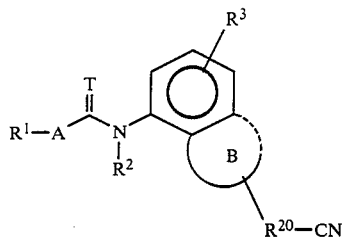 (IV)

(wherein A, B, $R^1$, $R^2$, $R^3$ and T have the same meaning as described hereinbefore)

with an azide.

Reactions to induce a 2-tetrazolyl group from a cyano group with an azide are known, it may be carried out, for example, under anhydrous conditions, using with azide (sodium azide, lithium azide, potassium azide etc.), in the presence of weak acid (pyridium chloride, ammonium chloride, dimethylaniline hydrochloride etc.) in an inert organic solvent (dimethylformamide, N-methylpyrrolidone etc.) with heating.

Process for the Preparation (3)

Among the compounds of the present invention, compounds of the general formula:

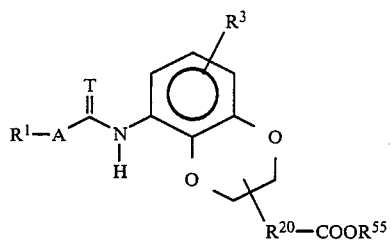 (Ib)

(wherein $R^{55}$ represents a hydrogen atom or a straight or branched alkyl group of from 1 to 6 carbon atom(s), and the A, $R^1$, $R^3$, $R^{20}$ and T have the same maning as described hereinbefore)

may be prepared by reacting a compound of general formula:

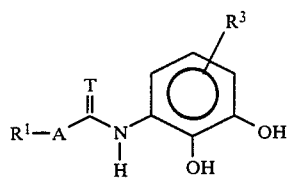 (V)

(wherein $R^1$, $R^3$, A and T have the same meaning as described hereinbefore)

and a compound of general formula:

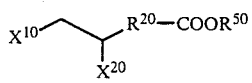 (VI)

or

 (VII)

(wherein $X^{10}$ and $X^{20}$ represent halogen atoms respectively, and $R^{50}$ represents a straight or branched alkyl group of from 1 to 6 carbon atom(s), and $R^{20}$ has the same meaning as described hereinbefore)

and further, subjecting the product thereof to esterification and/or saponification, if desired.

Reactions to form a benzodioxane ring from the catechol are known, and it may be carried out, for example, under on anhydrous conditions, in the presence of a condensing agent (potassium carbonate, sodium carbonate etc.) in an inert organic solvent (acetoine, methyl ethyl ketone, dioxane etc), with heating.

Process for the preparation (4)

Among the compounds of the present invention, compounds of the general formula:

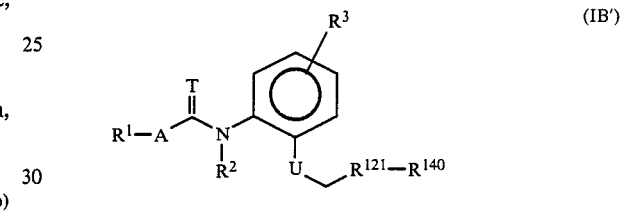 (IB')

(wherein $R^{121}$ represents a group of general formula: —$(CH_2)_r$— (wherein r represents zero or an integer of from 1 to 9); $R^{140}$ represents a group of general formula: —$COOR^8$ (wherein $R^8$ has the same meaning as described hereinbefore) or a group of formula:

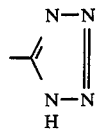

and A, $R^1$, $R^2$, $R^3$, T and U have the same meaning as described hereinbefore)

may be prepared by reacting a compound of general formula:

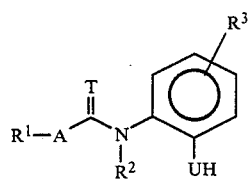 (XXXXV)

(wherein A, $R^1$, $R^2$, $R^3$, T and U have the same meaning as described hereinbefore)

and a compound of general formula:

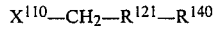 (XXXXVI)

(wherein $X^{110}$ represents a halogen atom, and $R^{121}$ and $R^{140}$ have the same meaning as described hereinbefore)

and further subjecting the product thereof to saponification and/or esterification, if desired.

Reactions of O-alkylation are known, and it may be carrie out, for example, under anhydrous conditions, in the presence of a base (sodium hydride, potassium carbonate, sodium carbonate etc), in a polar aprotic solvent (diethyl ether, tetrahydropyran, acetone etc) at from 0° C. to 100° C.

Process for the Preparation (5)

Among the compounds of the present invention of the general formula (I), certain compounds may be prepared from the corresponding compounds of the present invention.

For example, it may be carried out in the following reaction formula and reaction scheme [A].

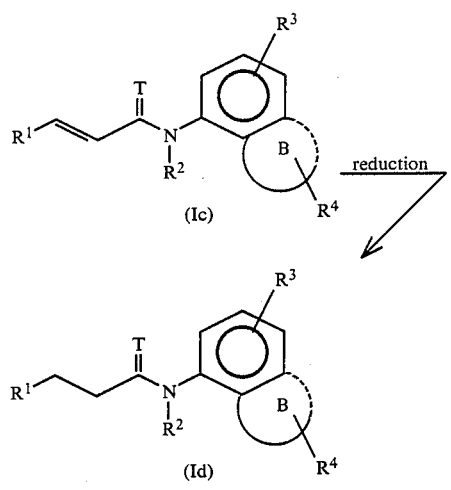

(in the above case, a reaction starting with a compound of formula (Ic) which substitutes a butadienylene and butenylene group, or group substituted by an alkyl or phenyl group for the vinylene group may also be carried out similarly)

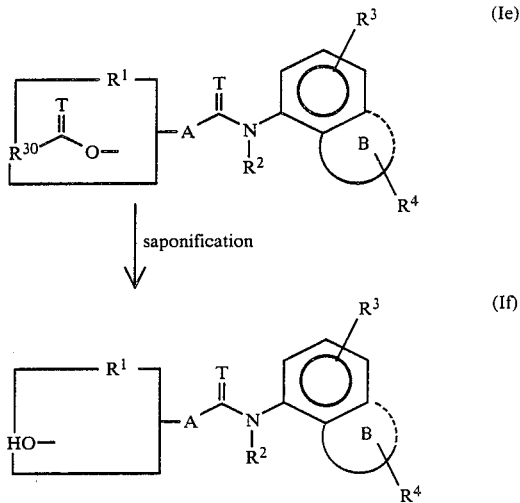

(wherein the symbol ▭ represents whole group of the substituent $R^1$ and symbols therein are included in $R^1$ respectively. $R^1$ and groups in $R^1$ have the same meaning as described above in the following schemes. $R^{30}$ represents an alkyl, alkenyl or alkynyl group of up to 18 carbon atoms(s))

Scheme [A]

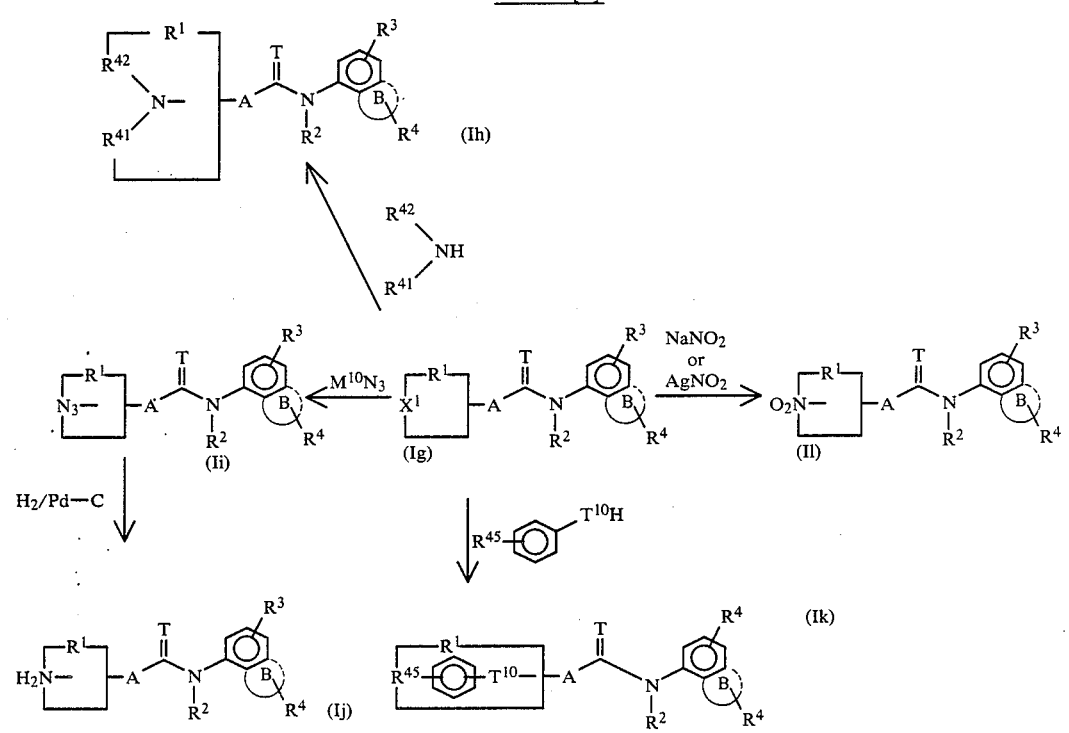

Each symbol in the scheme [A] represents the following meanings or as defined hereinbefore respectively.

$R^{40}, R^{41}$—an alkyl, alkenyl or alkynyl group of up to 18 carbon atom(s)

$R^{45}$—a hydrogen atom or an alkyl, alkenyl or alkynyl group of up to 18 carbon atom(s)

$T^{10}$—an oxygen atom or a sulphur atom, or an imido group $M^{10}$—a lithium, potassium or sodium atom $X^1$—a halogen atom Processes for the Preparation of Intermediates Intermediates described hereinbefore of the general (III), (IV), (V) and (XXXXV) may be prepared by the processes described in the following reaction schemes, respectively.

Each symbol in the schemes represent the following meanings or as described hereinbefore, respectively.

$R^{21}$—a straight or branched alkyl group of from 1 to 6 carbon atom(s)

$R^{51}, R^{52}, R^{53}, R^{56}$—a straight or branched alkyl group of from 1 to 6 carbon atom(s)

$R^{54}$—a hydrogen atom or a straight or branched alkyl group of from 1 to 6 carbon atom(s)

$R^{70}, R^{71}$—a trifluoroacetyl group $X^{30}, X^{40}, X^{50}$—a halogen atom $R^{122}, R^{180}$—a straight or branched alkyl group of from 1 to 6 carbon atom(s)

$R^{125}$—a group of formula: $-U-(CH_2)_n-$ or $-(CH_2)_p-$ (wherein u, n and p have the same meaning as described hereinbefore)

$R^{150}$—a trifluoroacetyl group $X^{120}, X^{130}, X^{140}, X^{150}$—a halogen atom When B contains an imino group, it is preferable to protect by trifluoro group(s) etc., and to remove the protecting group(s) in a suitable step.

And compounds of the general formula (IIIj) may be prepared by the same procedure as the method to obtain compounds of general formula (IIIh) from compounds of general formula (IIIg).

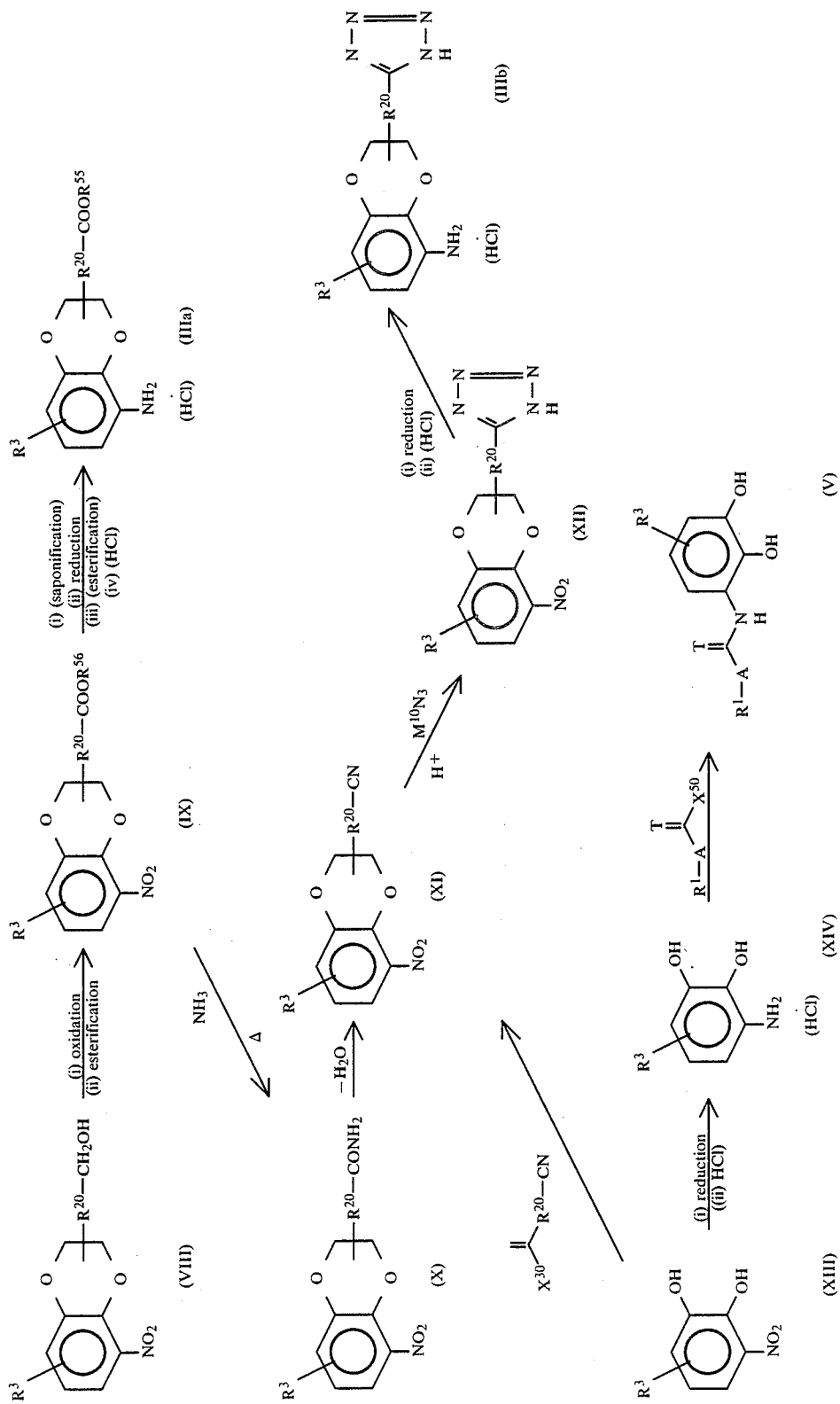

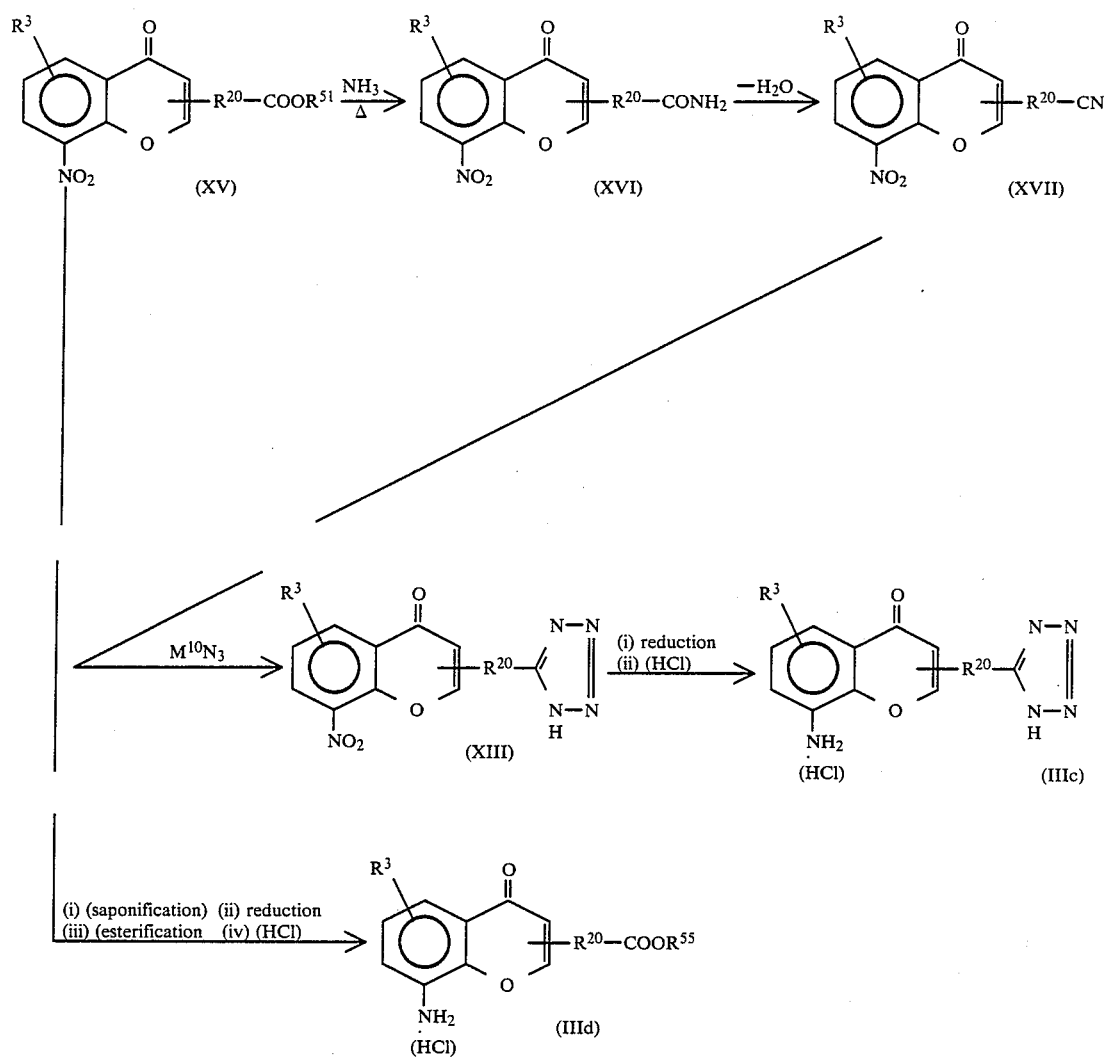
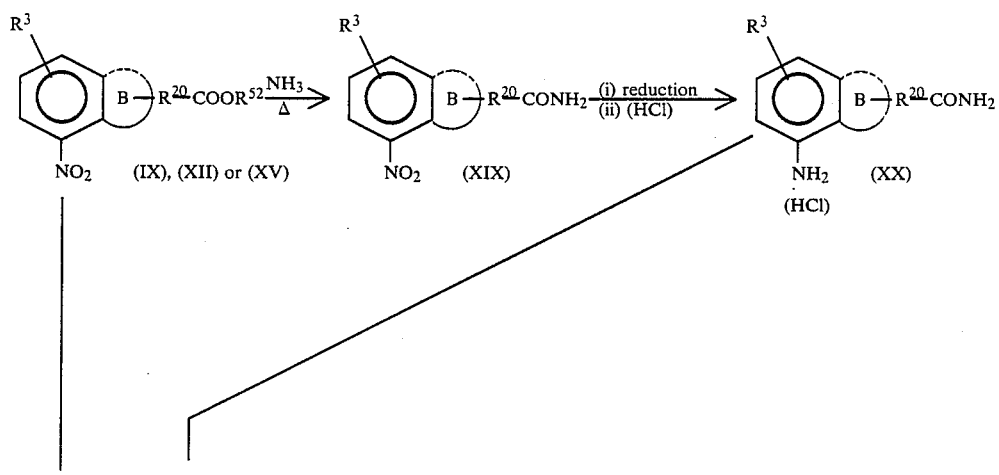

-continued
Scheme [D]
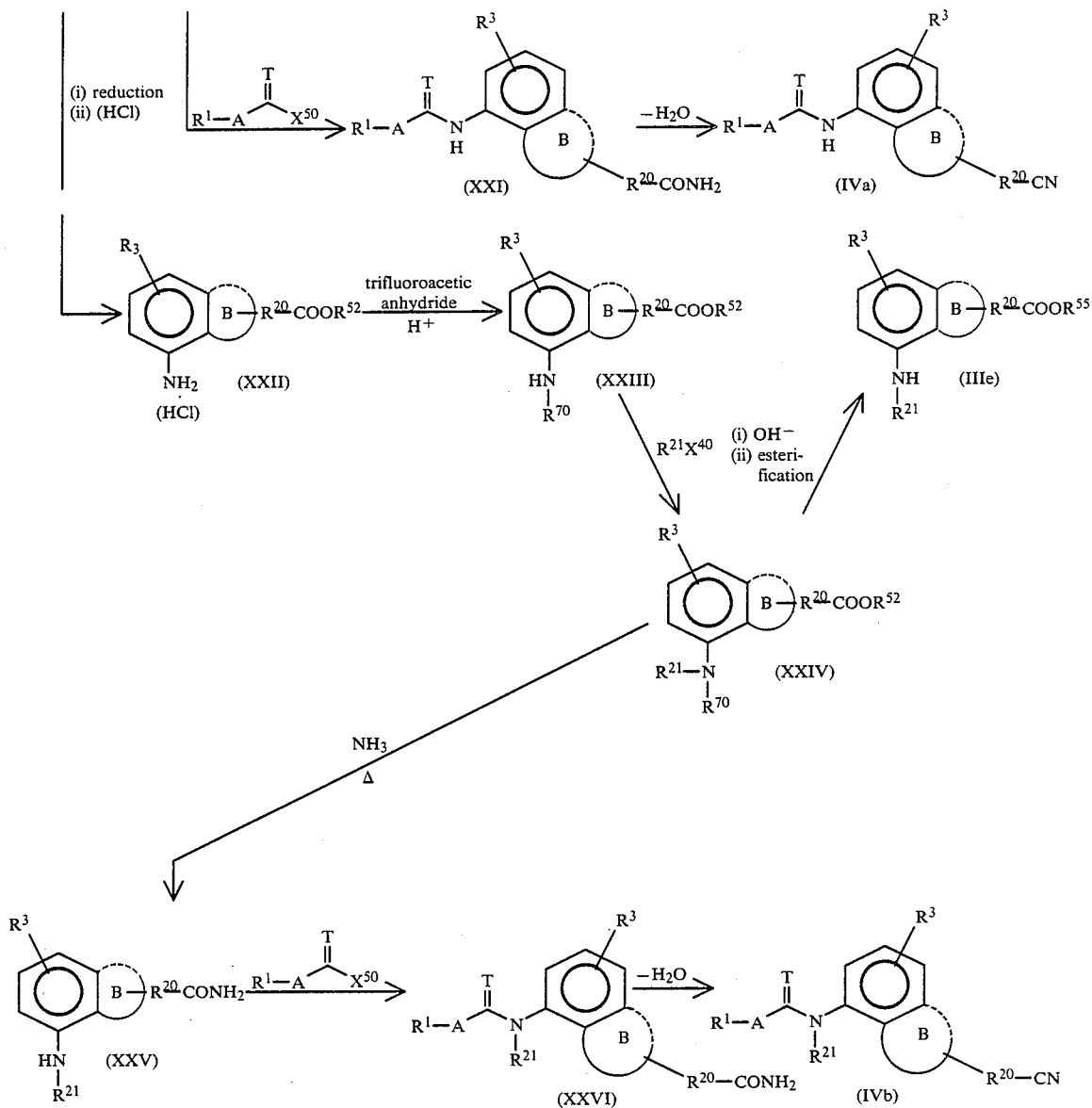

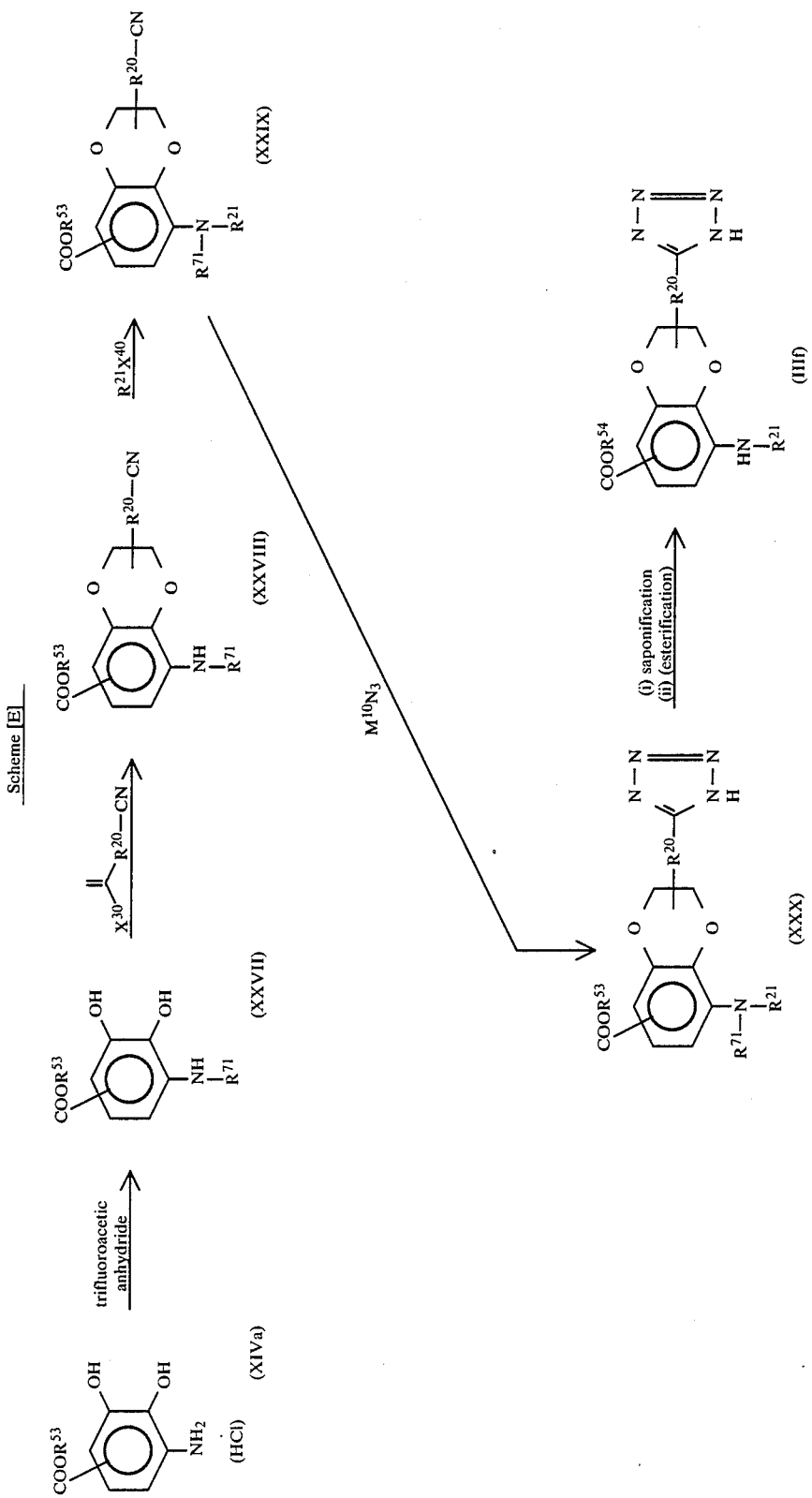

Scheme [F]
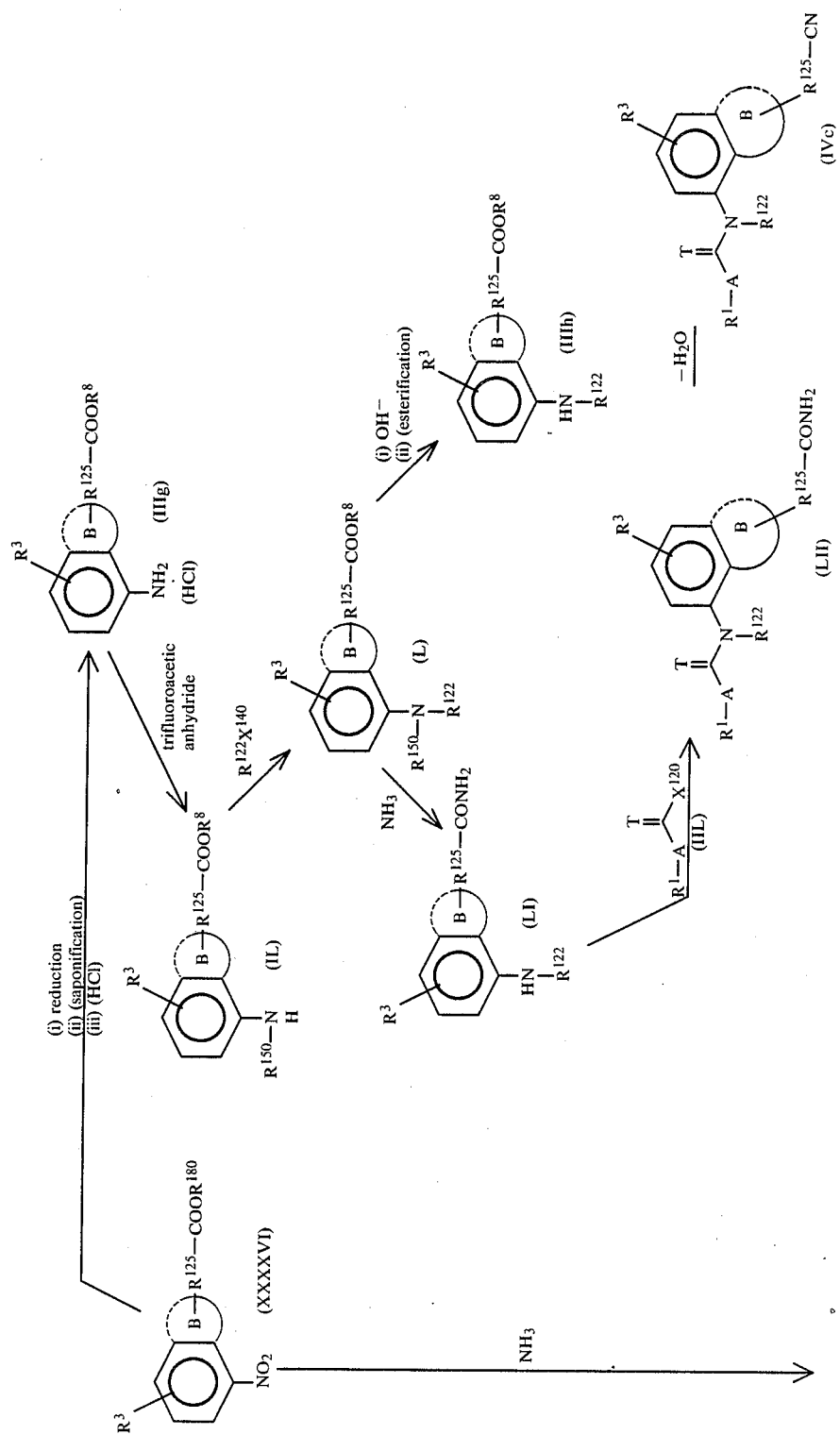

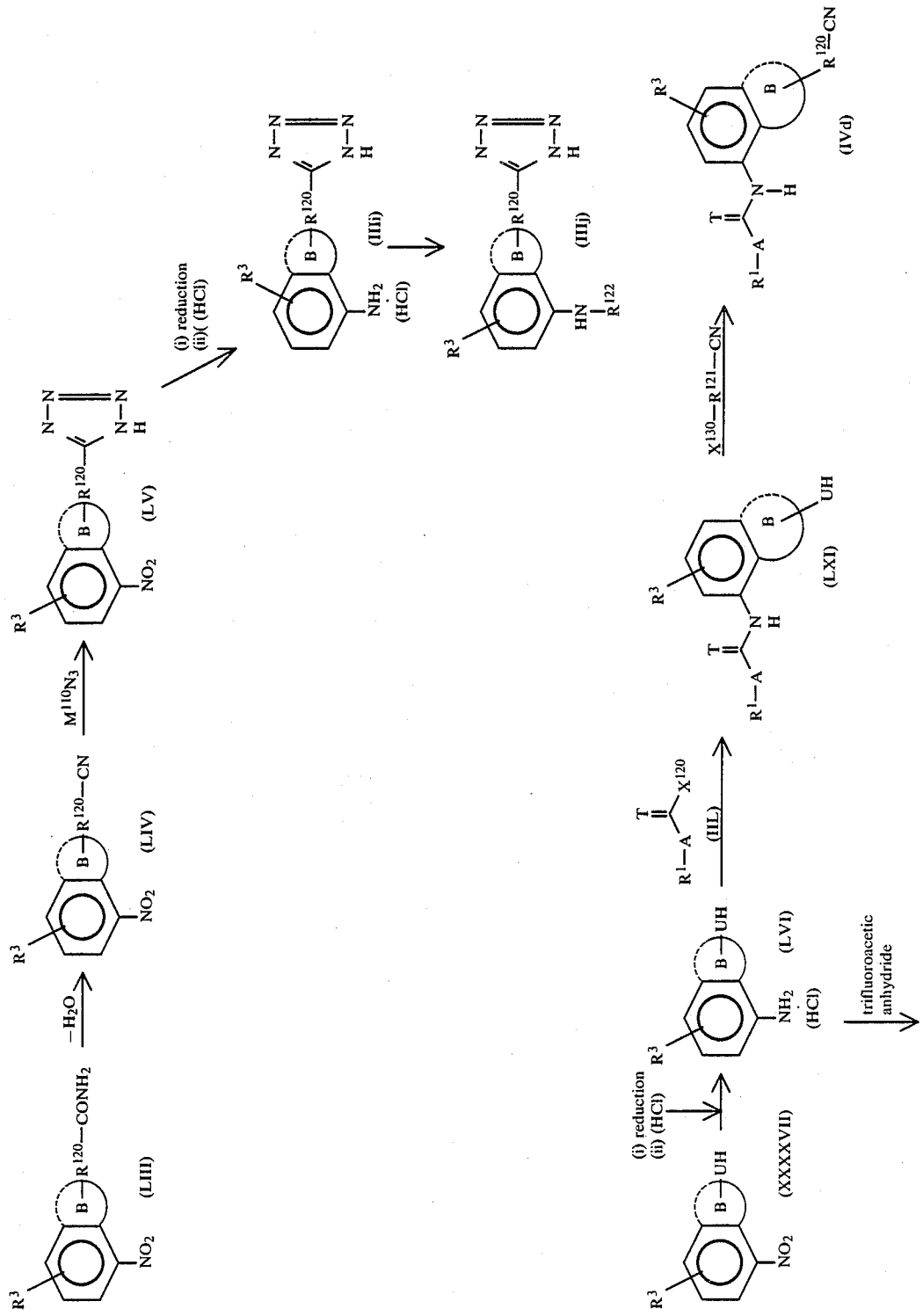

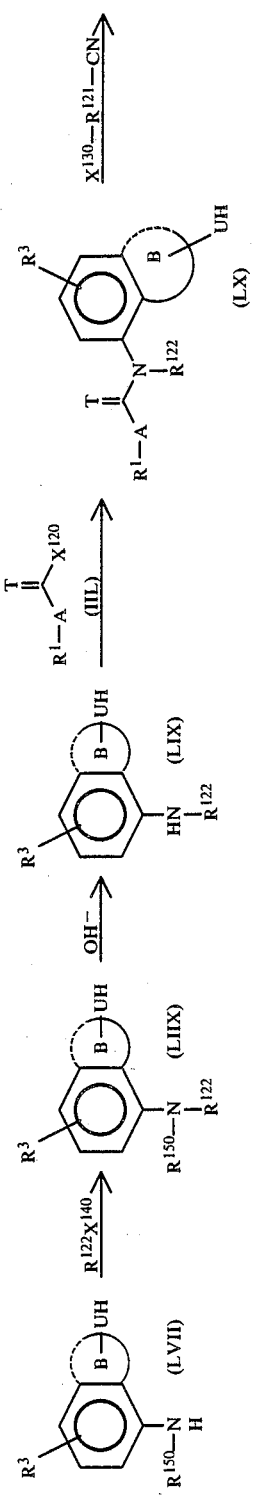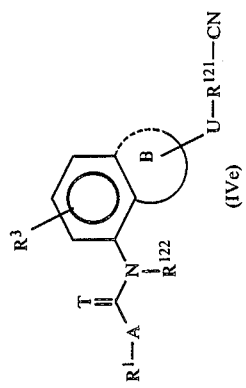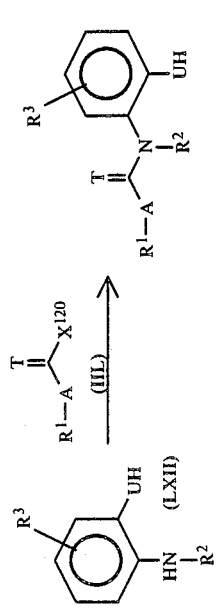

Intermediates having 1,4-dithianaphthalene skeleton also may be prepared using with a compound of general formula:

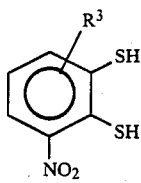

(XXXII)

(wherein R³ has the same meaning as described hereinbefore)

which may be obtained by hydrolyzing a compound of general formula:

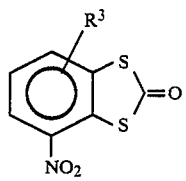

(XXXI)

(wherein R³ has the same meaning as described hereinbefore)

instead of the compound of the general formula (XIII).

In the processes for the preparation of the compounds of the present invention, esterification and saponification may be carried out as follows.

Conversion of a certain acid into a corresponding ester (i.e. esterification) is a known reaction per se, and it may be carried out, for example;
(1) by the method using a diazoalkane
(2) by the method using an alkyl halide
(3) by the method using DMF-alkylacetal and
(4) by the method reacting with a corresponding alkanol Concrete descriptions of the reactions above mentioned are as follows:

(1) the method using a diazoalkane may be carried out, for example, in an inert organic solvent (diethyl ether, ethyl acetate, methylene chloride, acetone, methanol, ethanol etc) using with corresponding diazoalkane.

(2) the method using an alkyl halide may be carried out, for example, in an organic solvent (acetone, N,N-dimethylformamide, DMSO etc.), in the presence of a base (potassium carbonate, sodium carbonate, sodium bicarbonate, potassium bicarbonate, calcium okide etc.) using with a corresponding alkyl halide.

(3) the method using DMF-dialkylacetal may be carried out, for example, in an inert organic solvent (benzene, toluene etc) using with a corresponding DMF-dialkylacetal.

(4) the method reacting with a corresponding alkanol may be carried out, for example, in a corresponding alkanol, using with an acid (hydrochloric acid, sulphuric acid, p-toluenesulphonic acid, hydrochloride gas etc) or condensing agent (DCC, pivaloyl chloride, arylsulphonyl halide, alkylsulphonyl halide etc.).

Reactions mentioned above are carried out generally at from −10° C. to 100° C.; and they may be carried out with a further addition of inert organic solvent(s) (THF, methylene chloride etc.) not related to the reactions.

Conversion of a certain ester into corresponding acid (i.e. saponification) is a known reaction per se, and it may be carried out, for example;

(1) using with an aqueous solution of an alkali (potassium hydroxide, sodium hydroxide, lithium hydroxide, potassium carbonate, sodium carbonate etc.) in a water-miscible organic solvent (THF, dioxane, ethanol, methanol etc.).

(2) using an alkali mehtioned above, in an alkanol (methanol, ethanol etc) in anhydrous condition.

The reactions above are carried out generally at from −10° C. to 100° C.

In each reaction in the present inventian, products may be purified by conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

Starting Materials

Starting materials and reagents in the present invention are known compounds per se or may be prepared by known methods per se.

For example, acids of the general formula (II) may be prepared by the methods described in the specification of Japanese Patent Application Kokai Nos. 60-97946, 60-116657, 60-142941, 60-142936 or 60-146855.

A certain compound of the general formula (VIII) wherein R³ is a hydrogen atom is described in J. Med. Chem., 8, 446 (1965).

A certain compound of the general formula (XIII) wherein R³ is a hydrogen atom is described in J. Am. Chem. Soc., 75, 3277 (1953).

The compounds of the general formula (XV) may be prepared by the method described in J. Med. Chem., 20, 371 (1977).

A certain compound of the general formula (XXXI) wherein R³ is a hydrogen atom is described in J. Org. Chem., 42, 1925 (1977).

The compounds of the general formula (XXXXVIII) may be prepared from the compounds of the general formula (II).

Compounds of the general formula (XXXXVI), (XXXXVII) and (XXXXVIII) are known compounds per se, or may be prepared by known methods per se.

For example, compounds wherein 3,4,5,6-tetrahydro-2H-pyran ring may be prepared by the methods described in J. O. Chem., 32, 4155 (1967), Chem. Abst. 98, 179352q (1983), J. O. Chem., 32, 4155 (1967), and Chem. Abst., 84, 58747z, respectively or similar methods thereof.

Salts

The compounds of the present invention of the genberal formula (I) may form salts at the carboxy or tetrazolyl moiety.

By converting into salts, solubility of the compounds of the present invention in water can be increased, and therefore may be more readily administered as pharmaceuticals.

The compounds of the present invention may easily be converted into corresponding salts by the methods known per se, e.g. methods described hereafter.

The salts in the present invention are preferably non-toxic ones. The non-toxic salts mean salts of cations that are relatively innocuous to living body (animals including human beings) tissues and that the effective pharmacological properties of the compounds of the general formula (I) are not impaired by side effect(s) resulting from the cations when used in an amount required for the prevention and/or treatment. And water-soluble salts are preferable.

Suitable salts include, for example, a salt of an alkali metal such as sodium, potassium, a salt of an alkaline metal such as calcium, magnesium, an ammonium salt and a pharmaceutically acceptable (non-toxic) amine salt.

Amines suitable for forming such salts with carboxylic acid or tetrazolyl group are well known and include, for example, those amines which are theoretically obtained by substituting one or more of hydrogen atom(s) of ammonia by other group(s). These groups, which may be the same or different when one or more hydrogen atom(s) are substituted, are selected from, for example, alkyl group(s) of from 1 to 6 carbon atom(s) and hydroxyalkyl group(s) of from 1 to 3 carbon atom(s). Suitable non-toxic amine salts include salts of a tetraalkylammonium group, such as tetramethylammonium salt and salts of an organic amine, such as methylamine, dimethylamine, cyclopentylamine, benzylamine, phenethylamine, piperidine, monoethanolamine, diethanolamine, lysine and alginine.

Salts can be obtained from the compounds of the present invention of the general formula (I), by methods known per se, for example, by reacting the compound of the general formula (I) and a suitable base such as a hydroxide or carbonate of an alkali metal or alkaline earth metal, ammonium hydroxide, ammonia or an organic amine in theoretical amounts in an appropriate solvent The salts can be isolated by freeze-drying the solution, or by filtration if the salts are sufficiently insoluble to the reaction solution, or if necessary, by removing part of the solvent followed by filtration.

Pharmaceutical Activities

The compounds of the present invention possess an antagonistic activity on leukotrienes, inhibitory activity on phospholipase, on 5α-reductase and on aldose reductase.

In a standard laboratory test, for example, the compounds of the present invention showed the pharmaceutical activity in the following tables.

The compounds of the present invention showed an antagonistic activity on $LTD_4$ in vitro (method is described hereafter), shown in the following tables.

TABLE I

Antagonistic activity of compounds of following general formula on $LTD_4$ (IA')

| R | $IC_{50}$ (μM) |
|---|---|
| alkyl | 0.07–40 |
| alkoxy | 0.009–0.9 |
| alkenyloxy | 0.0005–1.4 |
| alkynyloxy | 0.0002–0.013 |
| alkylthio | 0.17–17.5 |
| alkoxy substituted by halogen atom | 0.0004–0.007 |
| cycloalkylalkoxy | 0.08–0.2 |
| (alkyl)phenylalkoxy | 0.0004–0.7 |
| naphthylalkyl | 0.008 |

TABLE II

Antagonistic activity of compounds of following general formula on $LTD_4$ (IA")

| R | $IC_{50}$ (μM) |
|---|---|
| alkyl | 0.1–16 |
| alkoxy | 0.004–2.3 |
| alkenyloxy | 0.02–1.8 |
| alkynyloxy | 0.4–0.5 |
| alkylthio | 0.3–1.1 |
| alkoxy substituted by halogen atom | 0.003–0.08 |
| cycloalkyl | 0.5 |
| cycloalkylalkoxy | 0.09–1.5 |
| phenylalkoxy | 0.009–0.7 |

TABLE III

Comparison of activity by alkylene chain change

| Formula | $IC_{50}$ (μM) |
|---|---|
| 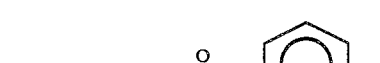 | 2.6 |

TABLE III-continued

Comparison of activity by alkylene chain change

| Formula | IC$_{50}$ (μM) |
|---|---|
| C$_5$H$_{11}$-C$_6$H$_4$-CH$_2$-C(=O)-NH-[benzodioxane-CH$_2$-tetrazole] | 8.3 |
| C$_5$H$_{11}$-C$_6$H$_4$-(CH$_2$)$_2$-C(=O)-NH-[benzodioxane-CH$_2$-tetrazole] | 0.66 |
| C$_3$H$_7$-C$_6$H$_4$-CH=CH-CH=CH-C(=O)-NH-[benzodioxane-CH$_2$-tetrazole] | 0.074 |
| C$_6$H$_{11}$-C$_6$H$_4$-C≡C-C(=O)-NH-[benzodioxane-CH$_2$-tetrazole] | 15.5 |
| C$_{13}$H$_{27}$-CH=CH-C(=O)-NH-[benzodioxane-CH$_2$-tetrazole] | 20.0 |

As is obvious from the Tables I and II, compounds of 1,4-benzodioxane skelton having any substituent R, represented by the general formula (IA') or (IA") among the compounds of the present invention (i.e. the case when B and R$^4$ are fixed and R$^1$ and A are changed in the general formula (I)) have enough activity for pharmaceutical use.

And from the Table III, it is confirmed if alkylene moiety (corresponding to A in the general formula (I)) would be converted, compounds having the enough pharmaceutical activity are given.

In the following tables, the comparision of activity by skeleton structure changes are shown.

TABLE IV

Comparison of activity by skeleton structure change (1)

| Formula | IC$_{50}$ (μM) |
|---|---|

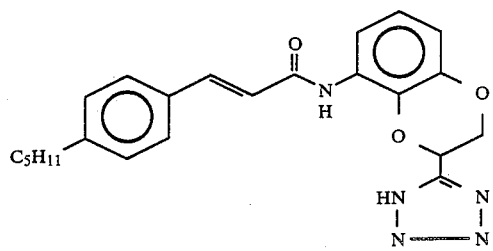

0.37

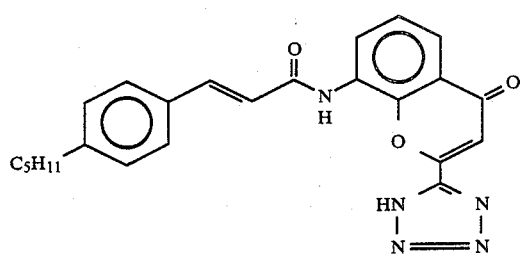

0.03

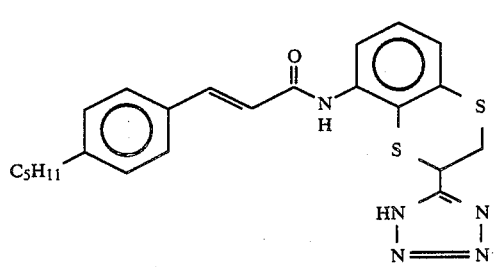

0.69

TABLE V

Comparison of activity by skeleton structure change (2)

| Formula | IC$_{50}$ (μM) |
|---|---|
| (structure) | 2.6 |
| (structure) | 0.18 |
| (structure) | 1.2 |

TABLE VI

Comparison of activity by skeleton structure change (3)

| Example No. | Symbol B | IC$_{50}$ (μM) |
|---|---|---|
| 1(501) | 2,5-dihydrofuran | 0.076 |
| 1(505) | tetrahydrofuran | 0.205 |
| 1(514) | benzene | 0.0046 |
| 1(516) | pyridine | 0.0026 |
| 1(518) | 1,3-dioxane | 0.033 |
| 1(521) | tetrahydropyran | 0.0013 |

And further, from the Table IV, V and VI, it can be clear that compounds in which the basic structural skeleton contains various rings also possess enough activity compared with the compounds having 1,4-benzodioxan skelton (i.e. the case that R$^1$ and the symbol A are fixed and the symbol B and R$^4$ are changed.).

According to the points above described, it is estimated fairly that replacement of an essential skelton of a certain compound from 1,4-benzodioxan to various rings and/or change of the groups of general formula: R$^1$—A— in the general formula (I) also lead a compound having enough activity for pharmaceutical use.

From the arguments above described, it is fully expected that all extent of the present invention have effective activity and therefore are useful as a pharmaceutical agent.

Antagonistic activity of the compounds of the present invention on LTD$_4$ were measured by the following method.

A segment of ilem (2.5 cm) was removed from guinea pig 300–400 g and suspended in a Magnus tube containing Tyrodes solution. The tube was maintained at 37° C. and aerated with 95% O$_2$–5% CO$_2$. After stabilizing from 30 mins, $5 \times 10^{-9}$ g/ml of LTD$_4$ was added to the Magnus tube. Contraction length at the time and contraction lengths when the compounds of the present invention were challenged at some concentrations were measured, and the IC$_{50}$ value were calculated.

(2) Inhibitory activity on 5α-reductase in vitro

The compounds of the present invention showed an inhibitory activity on 5α-reductase in vitro (method is described hereafter), shown in the following table.

TABLE VII

| Inhibitory activity on 5α-reductase | |
|---|---|
| Example No. | IC$_{50}$ (μM) |
| 4(205) | 2 |
| 4(206) | 4 |
| 6(1) | 5 |

Inhibitory activity of the compounds of the present invention on 5α-reductase was measured by the following method.

Inhibitory activity of the compounds of the present invention on 5α-reductase (IC$_{50}$) in vitro was measured by the following method.

Compounds tested were incubated with radioactive [4-$^{14}$C]testosterone (5 μM) and NADPH (5×10$^{-3}$M) in the medium containing 5α-reductase, 0.09M Hepes (pH 7.4) and 0.22M sucrose at 37° C. for 60 mins. The reaction was stopped by adding solution of chloroform-methanol (1:2). The reaction mixture was centrifuged and the supernatant was separated by thin layer chromatography on silica gel using chloroform-methanol-acetic acid (99.2:0.6:0.2) as a developing solvent. Radioactivity of formed 5α-dihydrotestosterone was measured by TLC scanner. The values of IC$_{50}$ were determined by the inhibition percents of 5α-reductase activity measured by the above procedure (see Endocrinal, Japon., 18, 179 (1971).).

Toxicity

On the other hand, it was confirmed that the acute toxicity (LD$_{50}$) over the full scope of the present invention was more than 500 mg/kg animal body weight by intravenous administration. Therefore, the compounds of the present invention may be considered to be sufficiently safe and suitable for pharmaceutical use.

For example, the values of LD$_{50}$ of the compounds prepared in Examples 1(76), 1(212), 1(230) and 1(247) were more than 1000 mg/kg animal body weight by intravenous administration in male mice weighing 170-180 g, respectively.

Application for Pharmaceuticals

The present invention is also related to methods of use as a leukotriene antagonist, phospholipase inhibitor, 5α-reductase inhibitor and/or aldose reductase inhibitor.

Surpressing leukotrienes is useful for the prevention and/or treatment of tracheal, bronchial or lung diseases such as asthma, allergic lung diseases, allergic shock or various allergic diseases in mammals including human beings, especially human beings.

Inhibiting phospholipases (phospholipase A$_2$ and/or phospholipase C) is useful for the prevention and/or treatment of diseases induced by the metabolites of arachidonic acid including leukotrienes described above, e.g. thrombosis such as thrombosis induced by damage of cerebral or coronary, endothelium or intina and inflammations such as arthritis, rheumatism in mammals including human beings, especially human beings.

Inhibiting 5α-reductase is useful for the prevention and/or treatment of prostatic hypertrophy, male pattern baldness or acne in mammals including human beings, especially human beings.

Inhibiting aldose reductases is useful for the prevention and/or treatment of diabetic complications e.g. retinopathy, diabetic cataract, nerve disturbances or renal disorders.

For the purposes hereinbefore described, the compounds of the present invention of the general formula or non-toxic salts thereof may normally be administered systemically or partially; usually by oral or parenteral administration.

The doses to be administered is determined depending upon age, body weight, symptom, the desired therapeutic effect, the route of administration, and the duration of the treatment etc. In the human adult, the doses per person per dose are generally between 0.1 mg and 100mg, preferably between 2 mg and 20 mg, by oral administration, up to several times per day, and between 10 ug and 10 mg, preferably between 0.1 mg and 1 mg, by parenteral administration up to several times per day.

As mentioned above, the doses to be used depend upon various conditions. Therefore, there are cases in which doses lower than or greater than the ranges specified above may be used.

Solid compositions according to the present invention for oral administration include compressed tablets, dispersible powders and granules. In such solid compositions, one or more of the active compound(s) is or are, admixed with at least one inert diluent such as lactose, mannitol, glucose, hydroxypropylcellulose, microcrystalline cellulose, starch, polyvinylpyrrolidone or magnesium metasilicate aluminate. The compositions may also comprise, as is normal practice, additional substances other than inert diluents e.g. lubricating agents such as magnesium stearate, disintegrating agents such as cellulose calcium gluconate, and assistant for dissolving e.g. arginine, glutamic acid or amino-acid such as aspartic acid. The tablets or pills may, if desired, be made into gastric film-coated or enteric film-coated tablets or pills, such as sugar-coated, gelatin-coated, hydroxypropyl cellulose-coated or hydroxypropylmethyl cellulose phthalate-coated tablets or pills; two or more of layers may be used. The compositions for oral administration also include capsules of absorbable material such as gelatin.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavoring, perfuming and preserving agents.

Other compositions for oral administration include spray compositions which may be prepared by known methods and which comprise one or more of the active compound(s).

Preparations for injection according to the present invention for parenteral administration include sterile aqueous or non-aqueous solutions, suspensions or emulsions. Examples of aqueous solvents or suspending media are distilled water for injection and physiological salt solution. Examples of non-aqueous solvents or suspending media are propylene glycol, polyethylene glycol, vegetable oils such as olive oil, alcohols such as ethanol, POLYSORBATE 80 (registered Trade Mark). These compositions may also include adjuvants such as preserving, wetting, emulsifying, despersing agents and assistant agent for dissolving (e.g. arginine, glutamic acid or amino-acid such as aspartic acid). They may be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

Other compositions for parenteral administration include liquids for external use, and endermic liniments such as ointments, suppositories and pessaries which comprise one or more of the active compound(s) and may be prepared by known methods.

Nomenclature and Excluding Compounds

Throughout the specification including claims, the compounds of the present invention are named as derivatives having the following fused benzene rings or benzene ring.

o 1,4-benzodioxane 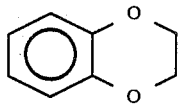

o 4H—1-benzopyran 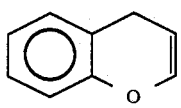

o 2,3-dihydro-1,4-dithianaphthalene 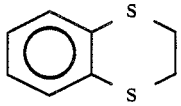

o benzofuran 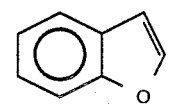

o 2,3-dihydro-1-benzofuran 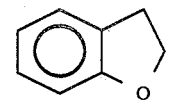

o quinoline 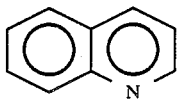

o 1,3-benzodioxole 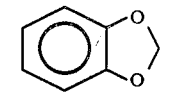

o naphthalene 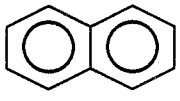

o 3,4-dihydro-2H—1,5-benzodioxepin 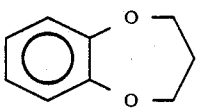

o 2,3-dihydro-1,4-benzoxazin 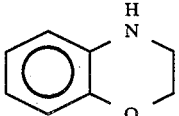

o 3,4-dihydro-2H—1-benzopyran 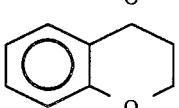

o 4H—1-benzothiopyran 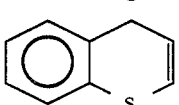

And throughout the specification including claims, isomers generated by the existence of stereo configuration unlimited (e.g. asymmetric carbon, double bond) are included in the corresponding formula, respectively.

With proviso that compounds which do not normally exist as judged from general chemical knowledge per se in for chemical or physical reasons (e.g., certain compounds having multiple bond which neighboured with an oxygen, nitrogen or sulphur atom.) are excluded from the present invention.

REFERENCE EXAMPLES AND EXAMPLES

The following reference examples and examples illustrate the present invention, but should not be constructed as limiting the present invention.

In the reference examples and examples, "TLC", "NMR", "IR" and "Mass" represent "Thin layer chromatography", "Nuclear magnetic resonance spectrum", "Infrared absorption spectrum" and "Mass spectrum", respectively.

The solvents in the parentheses show the developing or eluting solvents and the ratios of the solvents used are by volume in chromatographic separations.

Unless otherwise specified, "IR" was measured by the KBr tablet method and "NMR" was measured in a mixture of chloroform-d and ethanol-$d_4$ respectively.

REFERENCE EXAMPLE 1

Synthesis of 3-(m-methoxy-p-pentyloxycinnamoyl)aminopyrocatechol

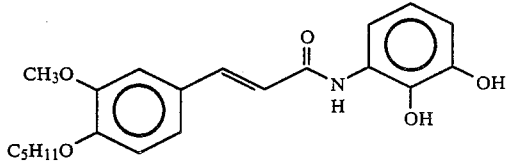

Oxyalyl chloride (4.5 ml) was added to m-methoxy-p-pentyloxybenzoic acid (528 mg). In an atmosphere of argon, the solution was stirred for 30 min at room temperature and then concentrated under reduced pressure. The residue was dissolved into methylene chloride (10 ml). In an atmosphere of argon, the solution was dropped to a solution of 3-aminopyrocatechol (275 mg) in a mixture of methylene chloride (10 ml) and pyridine (3 ml) cooling with ice, and the solution was stirred for 1 hr at the same temperature. After stirring for 2 hrs at room temperature, the solution was poured into 1N hydrochloric acid. The mixture was extracted with ethyl acetate. The extract was washed with water and a saturated aqueous solution of sodium chloride, successively, dried and concentrated under reduced pressure. Solids obtained was washed with hexane, and dried to give the title compound (700 mg) having the following physical data:

TLC: Rf 0.20 (ethyl acetate: hexane=1:2);

NMR (CDCl$_3$): δ10.00(1H, s), 7.75(1H d), 7.60(1H, s), 6.30–7.25(7H, m), 6.10(1H, s), 4.10(2H, t), 1.90(3H, s);

Mass: m/e 371(M+), 247, 177, 145, 125, 117, 89.

REFERENCE EXAMPLE 2

Synthesis of 8-(m-methoxy-p-pentyloxycinnamoyl)-amino-1,4-dioxane-2-carbonitrile

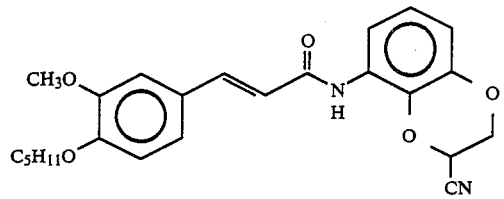

Dry potassium carbonate (770 mg) and 2-chloroacrylnitrile (0.30 ml) were added to a solution of 3-(m-methoxy-p-pentyloxycinnamoyl)aminopyrocatechol (690 ml; synthesized in reference example 1) in acetone (10 ml). In an atmosphere of argon, the mixture was refluxed for 3 hrs. The reaction mixture cooled to room temperature was poured into ice-water (50 ml). The mixture was extracted with ethyl acetate. The extract was dried, and concentrated under reduced pressure. The residue was purified by column chromatography on silica gel (methylene chloride: ethyl acetate=10:1) to give the title compound (565 mg) having the following physical data:

TLC: Rf 0.15 (ethyl acetate: hexane=1:2);

NMR (CDCl$_3$): $\delta$8.25(1H, dd), 7.70(1H, d), 7.55(1H, s), 7.00–7.25(2H, m), 6.90(1H, d), 6.85(1H, d), 6.70(1H, dd), 6.45(1H, d), 5.20(1H, dd), 4.30–4.55(2H, m), 4.05(2H, t), 3.93(3H, s);

Mass: m/e 422(M+), 247, 177, 145, 117.

REFERENCE EXAMPLE 3 (EXAMPLE A)

Synthesis of 8-(p-pentylcinnamoyl)amino-1,4-benzodioxane-2-acetic acid methyl ester

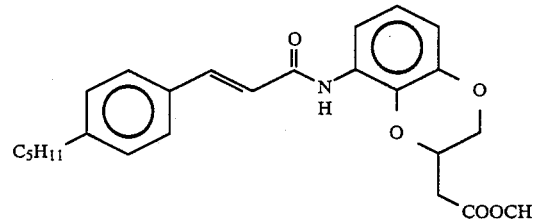

Potassium carbonate (509 mg) was added to a solution of 3-(p-pentylcinnamoyl)aminopyrocatechol (300 mg; synthesized by the same procedure as reference example 1) and 4-bromo-2-butenoic acid methyl ester in acetone (10 ml), and the mixture was refluxed for 10 min. The reaction mixture was poured into water. The mixture was extracted with ethyl acetate. The extract was purified by column chromatography on silica gel (hexane: ethyl acetate=5:1) to give the title compound (341 mg).

REFERENCE EXAMPLE 4

Synthesis of 8-(p-pentylcinnamoyl)amino-1,4-benzodioxane-2-acetamide

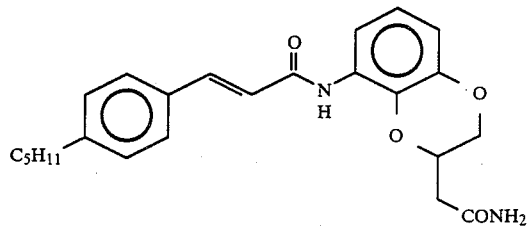

8-(p-pentylcinnamoyl)amino-1,4-benzodioxane-2-acetic acid methyl ester (341 mg; synthesized in reference example 3) was dissolved into ethanol which was saturated with ammonia (20 ml). The solution was allowed to stand for 3 days at 100° C. The reaction mixture was concentrated under reduced pressure. The residue was purified by column chromatography on silica gel (hexane: ethyl acetate=2:1) to give the title compound (191 mg).

REFERENCE EXAMPLE 5

Synthesis of 8-(p-pentylcinnamoyl)amino-1,4-benzodioxane-2-acetonitrile

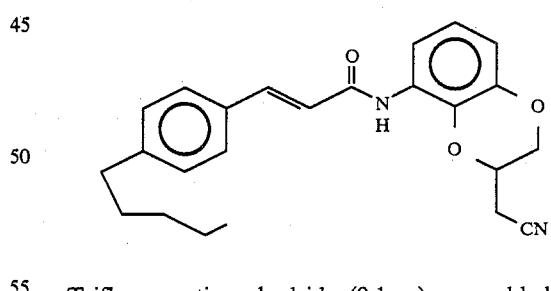

Trifluoroacetic anhydride (0.1 m) was added to a solution of 8-(p-pentylcinnamoyl)amino-1,4-benzodioxane-2-acetamide (191 mg; synthesized in reference example 4) in THF (10 ml) cooling with ice. And pyridine (0.02 ml) was added to the mixture. After stirring for 10 min, the mixture was poured into water. The mixture was extracted with ethyl acetate. The extract was dried, concentrated under reduced pressure to give the title compound.

EXAMPLE 1

Synthesis of 8-[p-(3Z-hexenyloxy)benzoyl/amino-2-(5-tetrazolyl)-1,4-benzodioxane

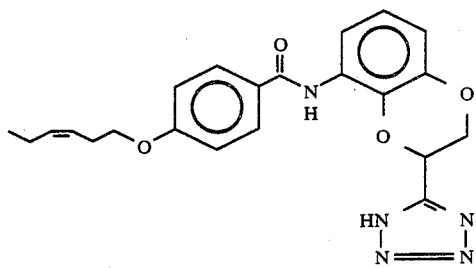

A mixture of p-(3Z-hexenyloxy)benzoic acid (110 mg) and oxalyl chloride (1 ml) was stirred for 1 hr at room temperature. From the mixture, excess oxalyl chloride was removed under reduced pressure. The residue was dried in vacuo, and then dissolved into methylene chloride (2 ml). In an atmosphere of argon, the solution was dropped into a solution of 8-amino-2-(5-tetrazolyl)-1,4-benzodioxane hydrochloride (128 mg) in a mixture of methylene chloride (2 ml) and pyridine (0.7 ml). The solution was stirred for 5 hrs at room temperature. The solution was diluted with ethyl acetate. The diluted solution was poured into 1N hydrochloric acid (1 ml). The mixture was extracted with ethyl acetate. The extract was washed with water, dried, and concentrated under reduced pressure. The residue was recrystallized from benzene to give the title compound (112 mg) having the following physical data:

TLC: Rf 0.57 (chloroform: methanol=3:1);

NMR: δ7.90(2H, d), 7.88(1H, m), 7.46(1H, dd), 6.96(2H, d), 6.92(1H, t), 6.78(1H, dd), 5.77(1H, dd), 5.70(2H, m), 4.61(2H, m), 4.04(2H, t), 2.57(2H, dt), 2.12(2H, m), 1.01(3H, t);

IR: ν3600–2300, 1650, 1610, 1540, 1505, 1460, 1250, 1175, 1090, 840, 770 cm$^{-1}$;

Mass: m/e 421(M+), 203;

Appearance: white powder.

EXAMPLE 1(1)–1(121)

By the same procedure as example 1, using with a corresponding carboxylic acid and 8-amino-2-(5-tetrazolyl)-1,4-benzodioxane hydrochloride, following compounds having the following physical data, shown in table [VIII] were given

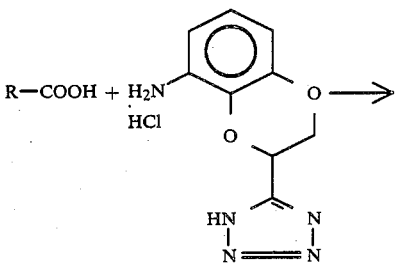

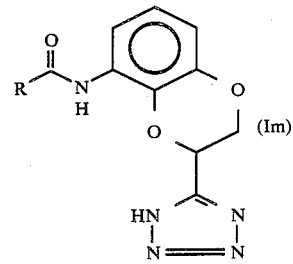

(Im)

TABLE VIII

| Example No. | Substituent R in the general formula (Im) | Rf value in TLC (developing solvent) | NMR (δppm) | IR (νcm$^{-1}$) | Mass | Appearance |
|---|---|---|---|---|---|---|
| 1(1) |  C$_5$H$_{11}$ | 0.51 (methylene chloride: methanol = 3:1) | 7.87(2H, d), 7.50(1H, dd), 6.92(1H, t), 6.77(1H, dd), 5.80(1H, dd), 4.68-4.54 (2H, m), 2.68(2H, t), 1.74-1.54(2H, m), 1.50-1.20(4H, m), 0.99(3H, t) | 3400-2400, 1640, 1610, 1540, 1460 | 393(M$^+$), 243, 175 | white powder |
| 1(2) |  C$_5$H$_{11}$S | 0.52 (methylene chloride: methanol = 4:1) | 7.83(2H, d), 7.49(1H, dd), 7.33(2H, d), 6.91(1H, t), 6.75(1H, dd), 5.76(1H, dd), 4.60(2H, m), 2.98(2H, t), 1.70(2H, m), 1.39(4H, m), 0.90(3H, t) | 3600-2300, 1635, 1620, 1595, 1545, 1460, 1340, 1280, 1265, 1100, 780 | 425, 207 | white powder |
| 1(3) |  C$_5$H$_{11}$S | 0.47 (methylene chloride: methanol = 4:1) | 7.68(1H, d), 7.46(2H, d), 7.26(2H, d), 6.89(1H, t), 6.73(1H, dd), 6.72(1H, d), 5.71(1H, dd), 4.68(1H, dd), 4.49(1H, dd), 2.96(2H, t), 1.68(2H, m), 1.39(4H, m), 0.90(3H, t) | 3600-2300, 1660, 1620, 1595, 1545, 1460, 1265, 1200, 1090, 970, 820 | 451(M$^+$) 233 | pale yellow crystal |
| 1(4) |  | 0.51 (methylene chloride: methanol = 17:3) | 7.69(2H, m), 7.53(2H, d), 6.98(2H, d), 6.90(1H, t), 6.73(1H, d), 6.58(1H, d), 5.71(1H, dd), 4.70(3H, m), 4.48(1H, dd), 2.24(2H, m), 1.14(3H, t) | 3600-2200, 1640, 1605, 1530, 1510, 1450, 1260, 1170, 995, 820 | 431(M$^+$) 219, 213 | yellow powder |
| 1(5) |  C$_6$H$_{13}$O | 0.40 (methylene chloride: methanol = 17:3) | 7.69(2H, m), 7.50(2H, d), 6.90(1H, t), 6.89(2H, d), 6.72(1H, dd), 6.62(1H, d), 5.72(1H, dd), 4.67(1H, dd), 4.49(1H, dd), 3.98(2H, t), 1.79(2H, m), 1.36(6H, m), 0.90(3H, t) | 3600-2100, 1640, 1600, 1530, 1500, 1440, 1255, 1190, 1160, 1090, 960, 815, 760, 700 | 449(M$^+$) 231, 219 | white powder |
| 1(6) |  C$_9$H$_{19}$ | 0.26 (chloroform: methanol = 3:1) | (CDCl$_3$) 8.23(1H, s), 7.79(2H, d), 7.22(2H, d), 7.05 (1H, t), 6.84(1H, t), 6.72(1H, d), 5.69(1H, m), 4.74(1H, dd), 4.46(1H, dd), 2.64(2H, t), 1.60 (2H, m), 1.15-1.45(12H, m), 0.87(3H, t) | 2930, 2860, 2740, 1635, 1610, 1540, 1450, 1325, 1275, 1090, 1040, 900, 850, 770, 715, 595 | 449(M$^+$), 299, 231, 145, 131, 118, 91 | white powder |

TABLE VIII-continued

| Example No. | Substituent R in the general formula (Im) | Rf value in TLC (developing solvent) | NMR (δppm) | IR (νcm$^{-1}$) | Mass | Appearance |
|---|---|---|---|---|---|---|
| 1(7) | ⟨4-C$_{10}$H$_{21}$-phenyl⟩ | 0.26 (chloroform:methanol = 3:1) | (CDCl$_3$) 8.12(1H, m), 7.81(2H, d), 7.25(2H, d), 7.02 (1H, d), 6.85(1H, t), 6.75(1H, d), 5.72(1H, m), 4.80(1H, dd), 4.47(1H, dd), 2.66(2H, t), 1.60 (2H, m), 1.15–1.45(14H, m), 0.87(3H, t) | 2930, 2860, 1640, 1620, 1605, 1540, 1470, 1335, 1285, 1270, 1100, 1050, 920, 780 | 463(M$^+$) 313, 245, 131, 118, 91, 69 | white powder |
| 1(8) | ⟨4-C$_{11}$H$_{23}$-phenyl⟩ | 0.26 (chloroform:methanol = 4:1) | (CDCl$_3$) 7.94(1H, s), 7.84(2H, d), 7.30(2H, d), 6.70–7.00(3H, m), 5.76(1H, m), 4.92(1H, dd), 4.50 (1H, dd), 2.68(2H, t), 1.63(2H, m), 1.15–1.45 (16H, m), 0.88(3H, t) | 2930, 2850, 1640, 1615, 1545, 1460, 1330, 1280, 1265, 1095, 775 | 477(M$^+$) 327, 259, 131, 118, 91 | white powder |
| 1(9) | ⟨4-C$_{12}$H$_{25}$-phenyl⟩ | 0.26 (chloroform:methanol = 4:1) | (CDCl$_3$) 7.97(1H, s), 7.84(2H, d), 7.28(2H, d), 6.70–7.00(3H, m), 5.74(1H, m), 4.90(1H, dd), 4.49(1H, dd), 2.68(2H, t), 1.63(2H, m), 1.15–1.45(18H, m) | 2930, 2850, 1640, 1615, 1545, 1460, 1335, 1280, 1265, 1090, 775 | 491(M$^+$) 341, 273, 131, 118, 91 | white powder |
| 1(10) | ⟨4-(C$_7$H$_{15}$O)-phenyl with allyl ether⟩ | 0.46 (chloroform:methanol = 3:1) | 7.70(2H, m), 7.54(2H, d), 6.94(2H, d), 6.91(1H, t), 6.74(1H, dd), 6.68(1H, d), 6.05(1H, m), 5.74(1H, dd), 5.38(2H, m), 4.70(1H, dd), 4.59(2H, d), 4.51(1H, dd) | 3600–2200, 1650, 1605, 1540, 1510, 1455, 1260, 1200, 1170, 1100, 1020, 980, 960, 820, 780, 715 | 405(M$^+$) 219, 187 | yellow powder |
| 1(11) | ⟨4-(C$_7$H$_{15}$O)-phenyl⟩ | 0.45 (chloroform:methanol = 3:1) | 7.71(2H, m), 7.56(2H, d), 6.94(3H, m), 6.77(1H, m), 6.72(1H, d), 5.79(1H, m), 4.72(1H, dd), 4.03(2H, m), 1.82(2H, m), 1.35(8H, m), 0.92(3H, m) | 3600–2200, 1650, 1595, 1440, 1260, 1170, 1090, 960, 820 | 463(M$^+$) 245, 231, 219 | yellow powder |
| 1(12) | ⟨4-(C$_4$H$_9$O)-phenyl⟩ | 0.39 (chloroform:methanol = 3:1) | 7.89(2H, d), 7.46(1H, dd), 6.88(2H, d), 6.81(1H, t), 6.75(5H, dd), 5.77(1H, dd), 4.62(2H, m), 4.04(2H, t), 1.80(2H, m), 1.51(2H, m), 0.90(3H, t) | 3600–2300, 1630, 1600, 1540, 1500, 1450, 1250, 1170, 1085, 840, 770 | 395(M$^+$) 177 | white powder |
| 1(13) | ⟨4-(C$_9$H$_{19}$O)-phenyl⟩ | 0.46 (chloroform:methanol = 3:1) | 7.89(2H, m), 7.46(1H, dd), 6.96(2H, d), 6.92(1H, t), 6.76(1H, dd), 5.76(1H, m), 4.62(2H, m), 4.02(2H, t), 1.81(2H, m), 1.26(10H, m), 0.88(3H, t) | 3600–2300, 1630, 1605, 1540, 1505, 1460, 1260, 1180, 1090, 840, 770 | 465(M$^+$) 247 | white powder |

TABLE VIII-continued

| Example No. | Substituent R in the general formula (Im) | Rf value in TLC (developing solvent) | NMR (δppm) | IR (νcm⁻¹) | Mass | Appearance |
|---|---|---|---|---|---|---|
| 1(14) | [4-(benzyl)phenyl with propenyl group] | 0.42 (chloroform: methanol = 3:1) | 7.72(1H, d), 7.64(1H, m), 7.48(2H, d), 7.36(2H, s), 7.22(6H, m), 6.90(1H, t), 6.73(1H, dd), 6.72(1H, d), 5.70(1H, dd), 4.67(1H, dd), 4.49(1H, dd), 3.99(2H, m) | 3600–2300, 1640, 1600, 1540, 1450, 1255, 1200, 1090, 970, 960, 730, 690 | 439(M⁺) 259, 221 | white powder |
| 1(15) | [4-(cyclohexyl)phenyl with propenyl group] | 0.44 (chloroform: methanol = 3:1) | 7.72(1H, d), 7.66(1H, m), 7.49(2H, d), 7.23(2H, d), 6.90(1H, t), 6.75(1H, d), 6.74(1H, dd), 5.72(1H, d), 4.68(1H, dd), 4.49(1H, dd), 2.53(1H, m), 1.86(5H, m), 1.40(5H, m) | 3600–2300, 1650, 1600, 1540, 1480, 1455, 1260, 1210, 1090, 980, 960, 820, 690 | 431(M⁺) 259, 221 | white powder |
| 1(16) | [4-(isobutyloxy)phenyl with propenyl group] | 0.30 (chloroform: methanol = 5:1) | 7.74(1H, d), 7.48(2H, d), 6.88(2H, d), 6.88(1H, t), 6.74(1H, dd), 7.44(1H, s), 5.72(1H, t), 4.62(2H, d), 4.01(2H, t) | 1660, 1610, 1580, 1540, 1515, 1460 | 435(M⁺) 217 | white powder |
| 1(17) | [4-(pentyl)phenyl with 2-methylpropenyl group, CH₃, C₅H₁₁] | 0.30 (methylene chloride: methanol = 5:1) | 7.40(2H, d), 7.36(1H, d), 7.18(2H, d), 6.89(1H, t), 6.74(1H, dd), 6.27(1H, d), 5.74(1H, t), 4.72–4.50(2H, m) | 3300, 3200–2300, 1660, 1610, 1540, 1460 | 433(M⁺) 215 | white powder |
| 1(18) | [4-(3-butenyloxy)phenyl with propenyl group] | 0.48 (chloroform: methanol = 3:1) | 7.69(1H, d), 7.63(1H, m), 7.51(2H, d), 6.90(2H, d), 5.90(1H, m), 5.72(1H, dd), 5.16(2H, m), 4.68(1H, dd), 4.49(1H, dd), 4.04(2H, t), 2.56(2H, dt) | 3600–2300, 1650, 1600, 1540, 1505, 1450, 1255, 1200, 1170, 1095, 1020, 960, 820 | 449(M⁺) 219, 201 | pale yellow powder |

TABLE VIII-continued

| Example No. | Substituent R in the general formula (Im) | Rf value in TLC (developing solvent) | NMR (δbpm) | IR (νcm$^{-1}$) | Mass | Appearance |
|---|---|---|---|---|---|---|
| 1(19) | (4-(3-methylbut-1-enyl)phenyl group) | 0.51 (chloroform:methanol = 3:1) | 7.69(1H, d), 7.64(1H, m), 7.51(2H, d), 6.90(1H, t), 6.89(2H, d), 6.73(1H, dd), 6.63(1H, d), 5.72(1H, dd), 4.68(1H, dd), 4.50(1H, dd), 3.98(2H, t), 1.80(2H, m), 1.62(1H, m), 1.36(2H, m), 0.92(6H, d) | 3600–2200, 1650, 1600, 1540, 1505, 1450, 1260, 1165, 1095, 960, 820 | 449(M$^+$), 231, 219 | white powder |
| 1(20) | C$_3$H$_7$O—phenyl | 0.26 (chloroform:methanol = 3:1) | (CDCl$_3$) 7.75–7.95(3H, m), 6.70–7.05(5H, m), 5.76(1H, m), 4.98(1H, dd), 4.50(1H, dd), 3.99(2H, t), 1.85(2H, t), 1.06(3H, t) | 2970, 2870, 2730, 1630, 1600, 1540, 1505, 1460, 1330, 1280, 1255, 1175, 1100, 840, 780 | 381(M$^+$), 231, 163, 121, 93, 65 | white powder |
| 1(21) | C$_6$H$_{13}$O—phenyl | 0.26 (chloroform:methanol = 3:1) | (CDCl$_3$) 7.94(1H, s), 7.87(2H, d), 6.70–7.10(5H, m), 5.75(1H, m), 4.88(1H, dd), 4.50(1H, dd), 4.01(2H, t), 1.82(2H, m), 1.20–1.60 (6H, m), 0.92(3H, t) | 3420, 2860, 1635, 1605, 1540, 1505, 1460, 1255, 1175, 1090, 840, 775 | 423(M$^+$), 395, 273, 205, 177, 121 | white powder |
| 1(22) | C$_7$H$_{15}$O—phenyl | 0.26 (chloroform:methanol = 3:1) | (CDCl$_3$) 7.80–8.00(2H, m), 6.70–7.05(5H, m), 5.74(1H, m), 4.90(1H, dd), 4.49(1H, dd), 4.00(2H, t), 1.80(2H, m), 1.15–1.70(8H, m), 0.89(3H, t) | 3420, 2930, 2860, 1640, 1605, 1550, 1510, 1460, 1260, 1180, 1100, 845, 775 | 437(M$^+$), 287, 219, 121, 93 | white powder |
| 1(23) | C$_8$H$_{17}$O—phenyl | 0.26 (chloroform:methanol = 3:1) | (CDCl$_3$) 7.75–8.00(3H, m), 6.70–7.05(5H, m), 5.74(1H, m), 4.90(1H, m), 4.48(1H, dd), 4.00(2H, t), 1.80(2H, m), 1.10–1.60 (14H, m), 0.88(3H, t) | 3430, 3320, 2930, 2850, 2730, 1635, 1605, 1545, 1505, 1460, 1320, 1255, 1180, 1090, 840, 770 | 451(M$^+$), 396, 301, 233, 121, 93 | white powder |
| 1(24) | C$_{10}$H$_{21}$O—phenyl | 0.26 (chloroform:methanol = 3:1) | (CDCl$_3$) 7.75–8.00(3H, m), 6.70–7.05(5H, m), 5.76(1H, m), 4.94(1H, dd), 4.50(1H, dd), 4.02(2H, t), 1.80(2H, m), 1.10–1.70 (14H, m), 0.88(3H, t) | 3420, 2930, 2850, 1640, 1610, 1545, 1510, 1460, 1260, 1180, 1100, 845 | 479(M$^+$), 261, 121, 93 | white powder |
| 1(25) | (isobutoxy)phenyl | 0.26 (chloroform:methanol = 3:1) | (CDCl$_3$) 7.94(1H, s), 7.86(2H, d), 6.70–7.10 (5H, m), 5.74(1H, m), 4.87(1H, dd), 4.48(1H, dd), 4.04(2H, t), 1.60–1.95 (3H, m), 0.98(6H, d) | 3420, 2960, 2870, 1635, 1605, 1540, 1505, 1460, 1260, 1180, 1100, 840, 775 | 409(M$^+$), 191, 121, 93 | white powder |

TABLE VIII-continued

| Example No. | Substituent R in the general formula (Im) | Rf value in TLC (developing solvent) | NMR (δppm) | IR (νcm$^{-1}$) | Mass | Appearance |
|---|---|---|---|---|---|---|
| 1(26) | 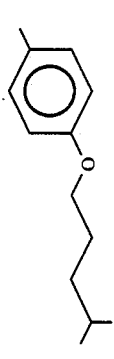 | 0.26 (chloroform: methanol = 3:1) | (CDCl$_3$) 7.88(2H, d), 7.83(1H, s), 6.75–7.10(5H, m), 5.76(1H, m), 4.96(1H, dd), 4.50(1H, dd), 4.01(2H, t), 1.20–1.95(5H, m), 0.93(6H, d) | 3420–2960, 2870, 1640, 1610, 1545, 1510, 1460, 1260, 1180, 1100, 845, 775 | 423(M$^+$), 381, 205, 161, 121, 93 | white powder |
| 1(27) |  | 0.53 (chloroform: methanol = 3:1) | 7.48(2H, d), 7.32(2H, d), 6.82(4H, m), 6.75(1H, t), 6.65(1H, dd), 6.14(1H, d), 5.63(1H, dd), 4.59(1H, dd), 4.42(1H, dd), 3.86(2H, t), 1.74(2H, m), 0.97(3H, t) | 3600–2300, 1650, 1600, 1440, 1250, 1160, 1120, 1090, 980, 830, 760 | 433(M$^+$) 215 | yellow powder |
| 1(28) |  | 0.49 (chloroform: methanol = 3:1) | 7.58(2H, m), 7.39(2H, d), 7.27(2H, d), 6.92(3H, m), 6.74(1H, dd), 6.28(1H, d), 5.72(1H, dd), 4.68(1H, dd), 4.51(1H, dd), 2.62(2H, t), 1.60(2H, m), 1.36(2H, m), 0.94(3H, t) | 3600–2200, 1650, 1600, 1530, 1440, 1260, 1095, 990, 835 | 431(M$^+$) 191, 213 | yellow powder |
| 1(29) |  | 0.30 (methylene chloride: methanol = 5:1) | 7.89(2H, d), 7.23(1H, d), 6.96(2H, d), 6.90(1H, m), 6.77(1H, dd), 6.02–5.80, (1H, m), 5.80–5.74(1H, m), 5.26–5.08, (2H, m), 4.84–4.50(2H, m) | 3500–2300, 1605, 1540, 1505, 835 | 393(M$^+$) 191, 175 | white powder |
| 1(30) |  | 0.65 (chloroform: methanol = 3:1) | 7.70(1H, d), 7.61(2H, d), 7.51(2H, d), 6.90(1H, t), 6.89(2H, d), 6.73(1H, dd), 6.64(1H, dd), 5.72(1H, dd), 5.50(2H, m), 4.68(1H, dd), 4.50(1H, dd), 4.00(2H, t), 2.55(2H, m), 2.10(2H, m), 1.00(3H, t) | 3600–2100, 1650, 1600, 1500, 1440, 1250, 1160, 1090, 1010, 960, 820 | 447(M$^+$) 229, 219 | yellow powder |
| 1(31) |  | 0.40 (methylene chloride: methanol = 4:1) | 7.31(1H, d), 7.48(2H, d), 6.89(1H, t), 6.87(2H, d), 6.74(1H, dd), 6.56(1H, d), 5.80–5.68(1H, m), 4.70–4.30(3H, m), 1.30(3H, d) | 3500–2300, 1660, 1605, 1540, 1515, 1460, 1260 | 435(M$^+$) 217 | pale yellow powder |
| 1(32) |  | 0.61 (chloroform: methanol = 3:1) | 7.72(1H, d), 7.62(1H, m), 7.51(2H, d), 6.92(2H, d), 6.91(1H, t), 6.74(1H, dd), 6.62(1H, d), 5.68(3H, m), 4.60(4H, m), 2.18(4H, m), 1.04(3H, t) | 3600–2200, 1645, 1600, 1540, 1505, 1450, 1260, 1165, 1100, 820 | 501, 433(M$^+$) 287, 219, 215 | yellow powder |

TABLE VIII-continued

| Example No. | Substituent R in the general formula (Im) | Rf value in TLC (developing solvent) | NMR (δppm) | IR (νcm⁻¹) | Mass | Appearance |
|---|---|---|---|---|---|---|
| I(33) | (4-methylphenyl-O-CH(CH₃)-C₃H₇ type structure) | 0.42 (chloroform: methanol = 3:1) | 7.87(2H, d), 7.38(1H, dd), 6.93(2H, d), 6.90(1H, t), 5.75(1H, dd), 4.68(1H, d), 4.55(1H, dd), 4.46(1H, m), 1.72(2H, m), 1.46(2H, m), 1.31(3H, d), 0.94(3H, t) | 3600–2300, 1630, 1600, 1540, 1500, 1455, 1250, 1180, 1100, 840, 770 | 409(M⁺) 219, 191 | white powder |
| I(34) | (4-methylphenyl)-O-CH₂-CH=CH-C₅H₁₁ | 0.44 (chloroform: methanol = 3:1) | 7.92(2H, d), 7.45(1H, dd), 7.05(2H, d), 6.92(1H, t), 6.77(1H, dd), 5.76(1H, m), 4.75(2H, t), 4.64(2H, m), 2.22(2H, m), 1.50(2H, m), 1.32(4H, m), 0.88(3H, t) | 3600–2200, 1635, 1600, 1540, 1500, 1450, 1260, 1220, 1170, 1080, 990, 835, 760 | 447(M⁺) 229, 219 | pale yellow powder |
| I(35) | (4-methylphenyl)-O-CH₂-CH=CH-C₅H₁₁ | 0.46 (chloroform: methanol = 3:1) | 7.90(2H, d), 7.45(1H, dd), 6.98(2H, d), 6.92(1H, t), 6.76(1H, dd), 5.76(1H, dd), 5.69(2H, m), 1.32(4H, m), 0.89(3H, t) | 3600–2300, 1630, 1600, 1500, 1450, 1240, 1165, 1080, 830, 760 | 449(M⁺) 329, 231, 219 | pale yellow solid |
| I(36) | (4-methylphenyl)-O-CH₂-(4-C₄H₉-phenyl) | 0.10 (chloroform: methanol = 4:1) | (CDCl₃) 7.80–8.00(3H, m), 7.32(2H, d), 7.19 (2H, d), 6.70–7.10(5H, m), 5.74(1H, m), 5.08(2H, s), 4.89(1H, dd) | 3420, 2930, 2850, 1630, 1605, 1540, 1500, 1455, 1245, 1170, 1090, 840, 770 | 485(M⁺) 399, 365, 339, 267, 253, 219, 147, 131 | white powder |
| I(37) | (4-methylphenyl)-O-CH₂-CH=CH-C₆H₁₃ | 0.35 (methylene chloride: methanol = 5:1) | 7.90(2H, d), 7.34(1H, dd), 6.98(2H, d), 6.92(1H, t), 6.78(1H, dd), 6.00–5.60 (3H, m), 4.80–4.50(4H, m) | 3400, 3200–2300, 1630, 1595, 1540, 1500, 1450, 1240 | 463(M⁺) 343, 245, 219, 121 | pale brown powder |
| I(38) | (4-propenylphenyl)-O-CH₂-CH=CH-C₆H₁₃ | 0.30 (methylene chloride: methanol = 5:1) | 7.73(1H, d), 7.49(2H, d), 6.90(2H, d), 6.90(1H, t), 6.78(1H, dd), 6.00–5.60 (3H, m), 4.80–4.50(4H, m) | 3350, 3100–2300, 1650, 1595, 1530, 1500, 1450, 1260 | 489(M⁺) 379, 343, 271 | white powder |

TABLE VIII-continued

| Example No. | Substituent R in the general formula (Im) | Rf value in TLC (developing solvent) | NMR (δppm) | IR (νcm⁻¹) | Mass | Appearance |
|---|---|---|---|---|---|---|
| I(39) | 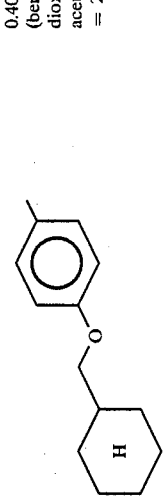 | 0.40 (benzene: dioxan: acetic acid = 20:10:1) | 7.9(2H, d), 7.5-7.3(1H, m), 7.0-6.7(4H, m), 5.78(1H, m), 4.7-4.5(2H, m), 3.8(2H, m), 2.0-1.6(6H, m), 1.4-1.0(5H, m) | 2920, 2850, 1620, 1600 | 435(M⁺) 217 | white powder |
| I(40) | 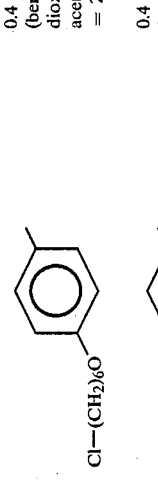 | 0.4 (benzene: dioxan: acetic acid = 20:10:1) | 7.9(2H, d), 7.5-7.3(1H, m), 7.0-6.7(4H, m), 5.75(1H, m), 4.8-4.5(2H, m), 4.0(2H, t), 3.55(2H, t), 1.8(4H, s), 1.5(4H, s) | 2950, 2850, 1630, 1600, 1460, 1250 | 457(M⁺) 239 | white powder |
| I(41) | 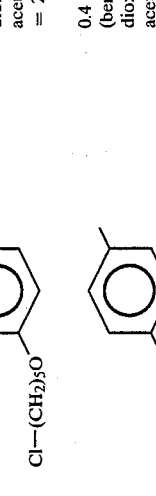 | 0.4 (benzene: dioxan: acetic acid = 20:10:1) | 7.9(2H, d), 7.5-7.3(1H, m), 7.0-6.7(4H, m), 5.78(1H, m), 4.8-4.5(2H, m), 4.05(2H, t), 3.65(2H, t), 1.85(4H, s), 1.7(2H, s) | 2950, 2850, 1630, 1600, 1460, 1250 | 443(M⁺) 225 | white powder |
| I(42) | 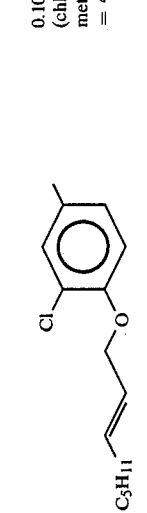 | 0.4 (benzene: dioxan: acetic acid = 20:10:1) | 7.9(2H, d), 7.5-7.3(1H, m), 7.0-6.7(4H, m), 5.78(1H, m), 4.8-4.5(2H, m), 4.1(2H, s), 3.65(2H, s), 2.6(4H, s) | 1670, 1640, 1490, 1290 | — | white powder |
| I(43) | 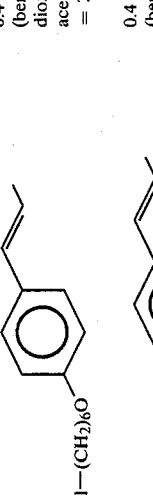 | 0.10 (chloroform: methanol = 4:1) | 7.98(1H, d), 7.82(1H, dd), 7.28(1H, m), 7.00(1H, d), 6.90(1H, t), 6.78(1H, dd), 5.60-6.00(3H, m), 4.45-4.85(4H, m), 2.10(2H, m), 1.20-1.50(6H, m), 0.88(3H, t) | 2930, 2860, 1640, 1615, 1600, 1545, 1500, 1460, 1270, 1100, 1060, 980, 780 | 483(M⁺) 373, 329, 265, 219, 155, 149 | white powder |
| I(44) |  | 0.4 (benzene: dioxan: acetic acid = 20:10:1) | 7.7(1H, d), 7.6-7.4(3H, m), 7.0-6.8(3H, m), 6.75(1H, d), 6.6(1H, d), 5.7(1H, s), 4.8-4.4(2H, m), 4.0(2H, t), 3.55(2H, t) | 2900, 1640, 1600, 1530, 1500, 1480, 1450 | 265 | pale brown powder |
| I(45) |  | 0.4 (benzene: dioxan: acetic acid = 20:10:1) | 7.7(1H, d), 7.6-7.4(3H, m), 7.0-6.8(3H, m), 6.75(1H, s), 5.7(1H, s), 4.8-4.4(2H, m), 4.0(2H, t), 2.0-1.6(6H, m), 1.5-0.9(5H, m) | 3300, 2920, 1650, 1600, 1510, 1450, 1250 | 461(M⁺) 243 | pale brown powder |

TABLE VIII-continued

| Example No. | Substituent R in the general formula (Im) | Rf value in TLC (developing solvent) | NMR (δppm) | IR (νcm$^{-1}$) | Mass | Appearance |
|---|---|---|---|---|---|---|
| 1(46) | Cl—(CH$_2$)$_4$O—[C$_6$H$_4$]—CH=CH—CH$_3$ | 0.4 (benzene:dioxan: acetic acid = 20:10:1) | 7.75(1H, d), 7.6-7.4(3H, m), 7.0-6.8(3H, m), 6.75(1H, d), 6.6(1H, d), 5.75(1H, s), 4.8-4.5(2H, m), 4.05(2H, s), 3.7(2H, s) | 2950, 1650, 1600, 1540, 1500, 1450, 1250 | 237 | pale brown powder |
| 1(47) | Cl—(CH$_2$)$_5$O—[C$_6$H$_4$]—CH=CH—CH$_3$ | 0.4 (benzene:dioxan: acetic acid = 20:10:1) | 7.7(1H, d), 7.6-7.4(3H, m), 7.0-6.8 (3H, m), 6.8-6.7(1H, m), 6.6(1H, d), 6.7(1H, m), 4.8-4.4(2H, m), 4.0(2H, t), 3.6(2H, t) | 2950, 1650, 1600, 1540, 1500, 1450, 1250 | 252 | white powder |
| 1(48) | [4-methylphenyl]—O—CH$_2$—CH=CH—CH$_2$— | 0.30 (methylene chloride: methanol = 5:1) | 7.88(2H, d), 7.26(1H, dd), 6.97(2H, d), 6.90(1H, t), 6.77(1H, dd), 6.00-5.60 (3H, m), 4.80-4.50(4H, m) | 3300, 3300-2300, 1640, 1610, 1550, 1510, 1460, 1260 | 421(M$^+$) 301, 219, 203 | pale yellow powder |
| 1(49) | [4-methylphenyl]—O—CH$_2$—CH=CH—CH$_2$—CH$_2$— | 0.38 (methylene chloride: methanol = 5:1) | 7.85(2H, d), 7.29(1H, dd), 6.92(2H, d), 6.87(1H, t), 6.73(1H, dd), 5.80-568 (1H, m), 5.65-533(2H, m), 4.66(1H, dd), 4.52(1H, dd) | 3420, 3300, 3300-2200, 1630, 1600, 1540, 1500, 1460, 1250, 840, 770 | 435(M$^+$) 409, 217, 191 | white powder |
| 1(50) | [Cl, C$_5$H$_{11}$O-substituted phenyl]—CH=CH—CH$_2$— | 0.25 (chloroform: methanol = 4:1) | 7.45-7.80(3H, m), 7.36(1H, dd), 6.80-7.00(2H, m), 6.72(1H, dd), 6.60(1H, d), 5.70(1H, m), 4.66(1H, dd), 4.51(1H, dd), 4.04(2H, t), 1.85(2H, m), 1.30-1.60 (4H, m), 0.95(3H, t) | 3350, 2940, 2860, 1660, 1610, 1600, 1530, 1495, 1455, 1265, 1200, 1100, 1060, 970, 915, 850, 810 | 469(M$^+$) 251, 219, 181, 153, 69 | pale brown powder |
| 1(51) | [2-C$_5$H$_{11}$-phenyl]—O—CH$_2$—[phenyl-4-CH$_3$] | 0.25 (chloroform: methanol = 4:1) | (CDCl$_3$) 7.80-8.05(3H, m), 7.15-7.45(4H, m), 6.70-7.15(5H, m), 5.76(1H, m), 5.13(2H, s), 4.93(1H, dd), 4.50(1H, dd), 2.67(2H, t), 1.90 (1H, s), 1.64(2H, m), 1.34(4H, m), 0.88(3H, t) | 3400, 2940, 2860, 1640, 1610, 1540, 1500, 1460, 1380, 1320, 1255, 1180, 1100, 1005, 900, 845, 780 | 499(M$^+$) 379, 281, 219, 181, 169, 161, 121, 105, 69 | white powder |
| 1(52) | [3-C$_4$H$_9$-phenyl]—O—CH$_2$—[phenyl-4-CH$_3$] | 0.25 (chloroform: methanol = 3:1) | (CDCl$_3$) 7.75-8.15(3H, m), 7.10-7.40(4H, m), 6.70-7.10(5H, m), 5.73(1H, m), 5.09(2H, s), 4.87(1H, dd), 4.47(1H, dd), 2.62(2H, t), 1.60(2H, m), 1.35(2H, m), 0.92(3H, t) | 3410, 2930, 2860, 1635, 1605, 1540, 1500, 1455, 1380, 1320, 1260, 1180, 1100, 900, 840, 780 | 485(M$^+$) 421, 365, 301, 267, 219, 147, 121, 105 | white powder |

TABLE VIII-continued

| Example No. | Substituent R in the general formula (Im) | Rf value in TLC (developing solvent) | NMR (δppm) | IR (νcm⁻¹) | Mass | Appearance |
|---|---|---|---|---|---|---|
| 1(53) | 4-(but-2-enyloxy)phenyl (allyl variant) | 0.50 (methylene chloride: methanol = 5:1) | 7.72(1H, d), 7.55(1H, d), 7.50(2H, d), 6.90(1H, t), 6.89(2H, d), 6.73(1H, dd), 6.59(1H, d), 5.80–5.68(1H, m), 5.38–5.68 (2H, m), 4.66(1H, dd), 4.54(1H, dd) | 3700–2200, 1650, 1600, 1540, 1510, 1450, 1260, 1180, 1100, 1030, 970, 830, 780 | 461(M⁺), 436, 315, 243, 219, 217, 181, 147 | pale green powder |
| 1(54) | 4-(pentyloxy)phenyl | 0.50 (methylene chloride: methanol = 5:1) | 7.89(2H, d), 7.30(1H, dd), 6.97(2H, d), 6.90(1H, t), 6.77(1H, dd), 6.00–5.60 (3H, m), 4.72(1H, dd), 4.60–4.50(3H, m) | 3400, 3200–2300, 1630, 1600, 1540, 1500, 1450, 1250 | 435(M⁺), 410, 315 | white powder |
| 1(55) | 4-(hex-2-enyloxy)phenyl | 0.44 (methylene chloride: methanol = 5:1) | 7.89(2H, dd), 7.31(1H, dd), 6.96(2H, dd), 6.90(1H, t), 6.76(1H, dd), 5.98–5.78 (1H, m), 5.78–5.72(1H, m), 5.14–4.94 (2H, m), 4.72(1H, dd), 4.55(1H, dd) | 3700–2200, 1640, 1610, 1550, 1510, 1460, 1280, 1180, 1100, 1050, 920, 840, 780 | 407(M⁺), 189, 147, 121, 93 | pale grey powder |
| 1(56) | 4-(hept-2-enyloxy)phenyl | 0.30 (methylene chloride: methanol = 5:1) | 7.73(1H, d), 7.50(2H, d), 7.50(1H, d), 6.91(2H, d), 6.90(1H, t), 6.75(1H, dd), 6.58(1H, d), 5.95–5.60(3H, m), 4.72–4.56 (2H, m), 4.50(2H, d) | 3350, 3100–2300, 1660, 1600, 1540, 1510, 1460, 1260 | 461(M⁺), 315, 243, 219, 147 | white powder |
| 1(57) | 4-alkoxyphenyl (C₇H₁₅) | 0.51 (methylene chloride: methanol = 5:1) | 7.99(2H, dd), 7.31(1H, dd), 6.98(2H, dd), 6.91(1H, t), 6.78(1H, dd), 5.98–5.60 (3H, m), 4.74(1H, dd), 4.57(1H, dd) | 3420, 2930, 3700–2200, 1640, 1610, 1550, 1510, 1460, 1320, 1260, 1180, 1100, 1050, 970, 910, 840, 780 | 477(M⁺), 259, 219, 121, 69 | pale brown powder |
| 1(58) | Cl(CH₂)₇O-phenyl | 0.51 (methylene chloride: methanol = 3:1) | (CDCl₃) 7.87(3H, m), 6.89(5H, m), 5.37(1H, m), 4.94(1H, m), 4.51(1H, m), 4.01(2H, t), 3.97(2H, t) | 3400, 1630, 1600, 1530, 500, 1450, 1310, 1250, 1170, 1090, 1040, 840, 770 | 471(M⁺), 435, 253 | white powder |
| 1(59) | Cl(CH₂)₈O-phenyl | 0.5 (methylene chloride: methanol = 3:1) | (CDCl₃) 7.86(3H, m), 6.86(5H, m), 5.76(1H, m), 4.99(1H, m), 4.52(1H, m), 4.01(2H, t), 3.53(2H, t) | 3400, 1630, 1600, 1520, 1490, 1450, 1250, 1170, 1100, 1000, 840, 770 | 485(M⁺), 449, 267 | white powder |
| 1(60) | Cl(CH₂)₉O-phenyl | 0.51 (methylene chloride: methanol = 3:1) | (CDCl₃) 7.86(3H, m), 6.89(5H, m), 5.76(1H, m), 4.98(1H, m), 4.52(1H, m), 4.02(2H, t), 3.53(2H, t) | 3400, 1630, 1600, 1540, 1500, 1450, 1320, 1260, 1170, 1090, 1040, 840, 770 | 499(M⁺), 463, 281 | white powder |

TABLE VIII-continued

| Example No. | Substituent R in the general formula (Im) | Rf value in TLC (developing solvent) | NMR (δppm) | IR (νcm⁻¹) | Mass | Appearance |
|---|---|---|---|---|---|---|
| 1(61) | 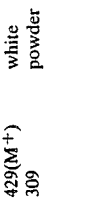 | 0.45 (chloroform:methanol = 3:1) | (CDCl$_3$) 7.88(3H, m) 7.40(5H, m), 7.04–6.74 (5H, m), 5.76(1H, m), 5.16(2H, s), 5.00(1H, m), 4.52(1H, m) | 3400, 1620, 1600, 1530, 1490, 1450, 1320, 1250, 1170, 1090, 1000 | 429(M$^+$) 309 | white powder |
| 1(62) |  | 0.5 (chloroform:methanol = 3:1) | 7.56(4H, m), 7.01–6.70(5H, m), 5.85 (1H, m), 4.60(2H, m), 4.01(2H, t), 3.55(2H, t) | 3400, 1650, 1590, 1530, 1500, 1450, 1250, 1170, 1090, 960, 820 | — | pale brown powder |
| 1(63) | 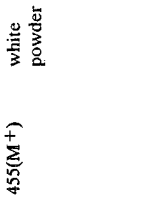 | 0.46 (chloroform:methanol = 3:1) | (CD$_3$OD) 7.72–7.30(1OH, m), 7.04–6.66(5H, m), 5.80(1H, m), 5.23(2H, s), 4.56(2H, m) | 3400, 1640, 1590, 1490, 1440, 1240, 1160, 1090, 990, 810, 730 | 455(M$^+$) | white powder |
| 1(64) | 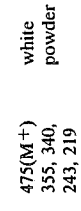 | 0.30 (methylene chloride:methanol = 3:1) | 7.90(2H, d), 7.30(1H, d), 6.98(2H, d), 6.92(1H, t), 6.78(1H, dd), 5.82–5.74 (1H, m), 5.56–5.42(1H, m), 5.14–5.04 (1H, m) | 3400, 2900, 3200–2300, 1635, 1605, 1545, 1505, 1460, 1260 | 475(M$^+$) 355, 340, 243, 219 | white powder |
| 1(65) | 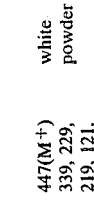 | 0.58 (methylene chloride:methanol = 5:1) | 7.90(2H, dd), 7.32(1H, dd), 6.97(2H, dd), 6.91(1H, t), 6.77(1H, dd), 5.96–5.60 (4H, m), 5.10–4.86(2H, m), 4.72(1H, dd), 4.65–4.40(3H, m) | 3600–2200, 1640, 1600, 1550, 1510, 1460, 1380, 1320, 1260, 1180, 1100, 1050, 1000, 910, 840, 780 | 447(M$^+$) 339, 229, 219, 121, 109, 93, 69 | white powder |
| 1(66) | 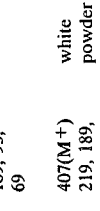 | 0.30 (methylene chloride:methanol = 5:1) | 7.89(2H, dd), 7.30(1H, dd), 6.98(2H, dd), 6.91(1H, t), 6.77(1H, dd), 6.04–5.60 (3H, m), 4.73(1H, dd), 4.65–4.46 (3H, m) | 3700–2100, 1640, 1600, 1550, 1510, 1460, 1380, 1320, 1260, 1180, 1100, 1050, 1000, 970, 900, 840, 780 | 407(M$^+$) 219, 189, 149, 121, 93, 69 | white powder |
| 1(67) | 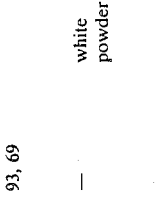 | 0.33 (methylene chloride:methanol = 5:1) | 7.73(1H, d), 7.48(2H, d), 6.88(2H, d), 6.89(1H, t), 6.74(2H, dd), 6.57(1H, d) | — | — | white powder |

TABLE VIII-continued

| Example No. | Substituent R in the general formula (Im) | Rf value in TLC (developing solvent) | NMR (δppm) | IR (νcm⁻¹) | Mass | Appearance |
|---|---|---|---|---|---|---|
| I(68) |  | 0.47 (methylene chloride: methanol = 5:1) | 7.89(2H, dd), 7.30(1H, dd), 6.96(2H, dd), 6.91(1H, t), 6.77(1H, dd), 5.77(1H, s), 4.74(1H, dd), 4.55(1H, dd), 4.02(2H, t) | 3700–2200, 2960, 1640, 1610, 1540, 1510, 1460, 1390, 1320, 1260, 1180, 1100, 1040, 900, 840, 780, 720 | 437(M⁺), 219, 149, 121, 93, 69 | white powder |
| I(69) |  | 0.37 (chloroform: methanol = 4:1) | 7.67(1H, d), 7.49(2H, d), 7.28(2H, d), 6.90(1H, t), 6.74(1H, d), 5.72(1H, dd), 4.67(1H, dd), 4.46(1H, dd), 2.62(2H, t), 1.59(2H, m), 1.28(6H, m), 0.86(3H, t) | 3600–2400, 2210, 1610, 1590, 1540, 1460, 1330, 1260, 1090, 1040, 940, 820, 770 | 431(M⁺), 219, 213 | yellow powder |
| I(70) | 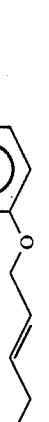 | 0.31 (methylene chloride: methanol = 5:1) | 7.93(1H, d), 7.58(2H, d), 7.58(1H, d), 6.90(2H, d), 6.89(1H, t), 6.74(1H, dd), 6.54(1H, d) | 3300, 3200–2300, 1650, 1595, 1540, 1505 | 447(M⁺), 301, 245 | white powder |
| I(71) | 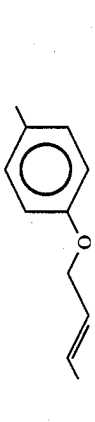 | 0.37 (methylene chloride: methanol = 5:1) | 7.89(2H, dd), 7.30(1H, dd), 6.97(2H, dd), 6.91(1H, t), 6.77(1H, dd), 6.00–5.60 (3H, m), 4.73(1H, dd), 4.56(1H, dd), 4.52(2H, d) | 3700–2200, 1640, 1600, 1550, 1510, 1460, 1380, 1320, 1260, 1180, 1100, 1050, 1000, 970, 910, 840, 780, 720 | 393(M⁺), 339, 219, 179, 149, 121, 93 | white powder |
| I(72) | 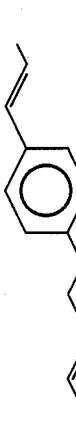 | 0.35 (methylene chloride: methanol = 5:1) | 7.69(1H, d), 7.50(1H, d), 7.40(2H, d), 6.88(2H, d), 6.86(1H, t), 6.70(1H, dd), 6.55(1H, d) | 3350, 3200–2300, 1650, 1600, 1530, 1500, 1450, 1255 | 433(M⁺), 287, 215 | pale yellow powder |
| I(73) |  | 0.30 (methylene chloride: methanol = 5:1) | 7.73(2H, d), 7.50(1H, d), 7.48(2H, d), 6.88(2H, d), 6.89(1H, t), 6.74(1H, dd), 6.58(1H, d) | 3350, 3200–2300, 1650, 1595, 1530, 1505, 1450, 1270 | 433(M⁺), 215 | pale yellow powder |
| I(74) |  | 0.20 (chloroform: methanol = 4:1) | 7.85(2H, d), 7.10–7.40(6H, m), 6.92(2H, d), 6.84(1H, d), 6.73(1H, d), 5.72(1H, m), 4.75(1H, dd), 4.50(1H, dd), 4.21(2H, t), 3.11(2H, t) | 3420, 3240, 3030, 2950, 2870, 2740, 1605, 1535, 1500, 1460, 1250, 1170, 1095, 1040, 1020, 910, 840, 765 | 443(M⁺), 408, 225, 201, 131, 121, 105, 84 | white powder |
| I(75) |  | 0.20 (chloroform: methanol = 4:1) | 7.70(1H, d), 7.40(2H, d), 7.15–7.40 (6H, m), 6.75–6.90(3H, m), 6.68(1H, d), 6.50(1H, d), 5.68(1H, m), 4.45–4.80 (2H, m), 4.15(2H, t), 3.08(2H, t) | 3400, 3040, 2870, 1660, 1605, 1540, 1510, 1450, 1260, 1200, 1175, 1100, 1020, 965, 830, 700 | 469(M⁺), 433, 251, 215, 147, 105 | pale yellow powder |

TABLE VIII-continued

| Example No. | Substituent R in the general formula (Im) | Rf value in TLC (developing solvent) | NMR (δppm) | IR (νcm⁻¹) | Mass | Appearance |
|---|---|---|---|---|---|---|
| 1(76) |  | 0.20 (chloroform:methanol = 4:1) | (CDCl$_3$) 8.00(1H, s), 7.86(2H, d), 7.10-7.40 (5H, m), 6.70-7.00(5H, m), 5.74(1H, m), 4.88(1H, dd), 4.50(1H, dd), 4.02(2H, m), 2.70(2H, m), 1.85(4H, m) | 3400, 3030, 2950, 1635, 1605, 1540, 1505, 1460, 1260, 1175, 1095, 840, 770, 700 | 471(M$^+$), 253, 121, 91 | white powder |
| 1(77) | 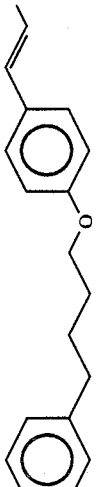 | 0.20 (chloroform:methanol = 4:1) | 7.70(1H, d), 7.45(2H, d), 7.10-7.55 (6H, m), 6.80-6.95(3H, m), 6.71(1H, d), 6.56(1H, d), 5.70(1H, m), 4.45-4.80 (2H, m), 3.97(2H, m), 2.70(2H, m), 1.80(4H, m) | 3350, 3030, 2950, 2870, 1660, 1600, 1540, 1510, 1450, 1260, 1200, 1175, 1105, 970, 830, 780 | 497(M$^+$), 279, 219, 147, 91 | pale yellow powder |
| 1(78) |  | 0.20 (chloroform:methanol = 4:1) | (CDCl$_3$) 7.97(1H, s), 7.89(2H, d), 7.03(2H, d), 6.70-7.00(3H, m), 5.75(1H, m), 4.90(1H, dd), 4.73(2H, m), 4.49(1H, dd), 2.22(2H, t), 1.62(1H, m), 1.40(2H, m), 0.87(6H, d) | 3400, 2960, 1635, 1605, 1540, 1500, 1460, 1260, 1230, 1175, 1095, 1000, 840, 775 | 447(M$^+$), 279, 229, 147, 121, 91 | white powder |
| 1(79) | 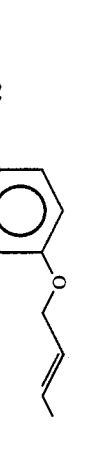 | 0.45 (methylene chloride:methanol = 5:1) | 7.75(1H, d), 7.51(2H, d), 7.51(1H, d), 6.92(2H, d), 6.91(1H, t), 6.76(1H, dd), 6.60(1H, d), 6.00-5.62(3H, m), 4.74-4.44 (4H, m) | 3700-2200, 1660, 1600, 1550, 1520, 1490, 1460, 1260, 1180, 1100, 1050, 970, 920, 830, 780, 720 | 419(M$^+$), 219, 201, 147, 105 | pale yellow powder |
| 1(80) |  | 0.33 (methylene chloride:methanol = 5:1) | 7.72(1H, d), 7.48(2H, d), 7.44(1H, d), 6.89(2H, d), 6.88(1H, t), 6.73(1H, dd), 6.55(1H, d), 6.00-5.60(3H, m), 4.70-4.56 (2H, m), 4.48(2H, d) | 3350, 3200-2300, 1650, 1590, 1530, 1500, 1440, 1250 | 503(M$^+$), 357 | white powder |
| 1(81) | 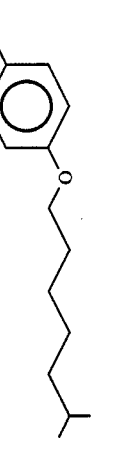 | 0.34 (methylene chloride:methanol = 5:1) | 7.88(2H, d), 7.32(2H, d), 6.95(2H, d), 6.90(1H, t), 6.76(1H, dd), 5.80-5.72 (1H, m), 4.70(1H, dd), 4.55(1H, dd), 4.01(2H, t) | 3400, 3200-2300, 1630, 1600, 1540, 1500, 1460, 1250 | 451(M$^+$), 233, 121 | white powder |
| 1(82) | 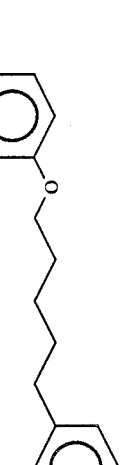 | 0.30 (methylene chloride:methanol = 5:1) | 7.75(1H, d), 7.50(2H, d), 7.45(1H, d), 7.36-7.15(5H, m), 6.91(1H, t), 6.89(2H, d), 6.76(1H, dd), 6.66(1H, d), 5.75(1H, t), 4.63(2H, d), 3.98(2H, t) | 3350, 3100-2250, 1660, 1600, 1540, 1510, 1450, 1260 | 511(M$^+$), 293, 251, 219 | white powder |

TABLE VIII-continued

| Example No. | Substituent R in the general formula (Im) | Rf value in TLC (developing solvent) | NMR (δppm) | IR (νcm⁻¹) | Mass | Appearance |
|---|---|---|---|---|---|---|
| 1(83) | 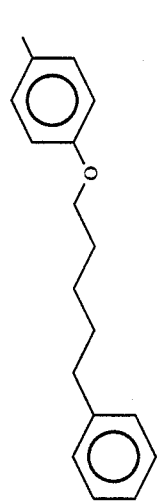 | 0.35 (methylene chloride methanol = 5:1) | 7.87(2H, d), 7.36-7.11(6H, m), 6.94(2H, d), 6.80(1H, t), 6.76(1H, dd), 5.76(1H, dd), 4.72(1H, dd), 4.55(1H, dd), 4.00(2H, t) | 3400, 3100-2250, 1630, 1600, 1540, 1505, 1450, 1300, 1260 | 485(M⁺) 267 | white powder |
| 1(84) | 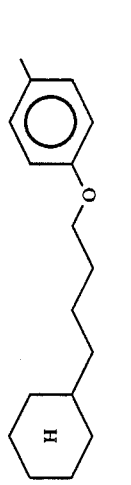 | 0.45 (methylene chloride methanol = 5:1) | 7.88(2H, d), 7.32(1H, dd), 6.95(2H, d), 6.90(1H, t), 6.76(1H, dd), 5.76(1H, t), 4.75-4.50(2H, m), 4.01(2H, t) | 3440, 2930, 2850, 1640, 1610, 1550, 1510, 1460, 1260 | 477(M⁺) 259 231 | white powder |
| 1(85) |  | 0.32 (methylene chloride methanol = 5:1) | 7.72(1H, d), 7.48(2H, d), 7.44(1H, d), 6.88(1H, t), 6.87(2H, d), 6.73(1H, dd), 6.57(1H, m), 5.71(1H, m), 4.68-4.51 (2H, m), 3.97(2H, d) | 3430, 2930, 2850, 1660, 1600, 1540, 1510, 1450, 1260 | 503(M⁺) 285 | yellow powder |
| 1(86) |  | 0.30 (methylene chloride methanol = 5:1) | 7.72(1H, d), 7.48(2H, d), 6.88(1H, t), 6.87(2H, d), 6.73(1H, dd), 6.56(1H, d), 0.87(6H, d) | 3350, 3200-2300, 1655, 1600, 1540, 1510, 1450, 1260 | 477(M⁺) 259 | pale yellow powder |
| 1(87) | 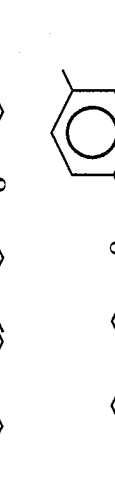 | 0.32 (methylene chloride methanol = 5:1) | 7.89(2H, d), 7.27(1H, dd), 6.96(2H, d), 6.90(1H, t), 6.77(1H, dd), 5.70-5.30 (2H, m) | 3400, 3200-2300, 1640, 1605, 1545, 1500, 1450, 1260 | 449(M⁺) 369 231 | white powder |
| 1(88) |  | 0.32 (methylene chloride methanol = 5:1) | 7.89(2H, d), 7.44(2H, d), 7.38(1H, dd), 6.91(1H, t), 6.77(1H, dd), 4.55(2H, s) | 3350, 3200-2300, 1630, 1605, 1535, 1450, 1090 | 437(M⁺) 287 219 | white powder |
| 1(89) |  | 0.45 (methylene chloride methanol = 5:1) | 7.89(2H, d), 7.36(1H, d), 6.94(2H, d), 6.91(1H, t), 6.76(1H, d), 3.68(3H, s) | 3325, 3200-2300, 1730, 1640, 1610, 1460, 1260 | 467(M⁺) 391, 322 | white powder |

TABLE VIII-continued

| Example No. | Substituent R in the general formula (Im) | Rf value in TLC (developing solvent) | NMR (δppm) | IR (νcm⁻¹) | Mass | Appearance |
|---|---|---|---|---|---|---|
| I(90) | 4-methylphenyl-S-pentyl | 0.45 (methylene chloride: methanol = 5:1) | 7.82(2H, d), 7.41(1H, dd), 7.32(2H, d), 6.91(1H, t), 6.76(1H, d), 2.97(2H, t) | 3400, 3200–2300, 1645, 1620, 1605, 1550, 1460, 1100 | 453(M⁺) 302, 235 | white powder |
| I(91) | 4-(isobutoxymethyl)phenyl-propenyl | 0.38 (methylene chloride: methanol = 5:1) | 7.76(1H, d), 7.52(2H, d), 7.34(2H, d), 6.88(1H, b), 6.73(1H, dd), 6.70(1H, d), 4.50(2H, s), 3.50(2H, t), 0.90(6H, d) | 3370, 3200–2300, 1660, 1610, 1545, 1460, 1260, 1100 | 449(M⁺) 245, 231, 219 | white powder |
| I(92) | 4-(isopentyloxy)phenyl-propenyl | 0.34 (methylene chloride: methanol = 5:1) | 7.72(1H, d), 6.49(2H, d), 7.17(1H, dd), 6.00–6.80(6H, m), 6.74(1H, dd), 6.57(1H, d), 4.21(2H, t), 3.32(2H, t) | 3350, 3200–2300, 1660, 1610, 1540, 1510, 1460, 1260, 1180, 830 | 475(M⁺) 365, 257, 219 | white powder |
| I(93) | 2-thienyl-CH=C(CH₃)- pentyloxy | 0.33 (methylene chloride: methanol = 5:1) | 7.50(1H, s), 7.58(1H, d), 7.37(2H, d), 6.93(2H, d), 6.84(1H, t), 6.84–6.74(2H, m), 5.80(1H, m), 2.38(3H, d), 0.92(6H, d) | 3400, 3200–2300, 1635, 1600, 1505, 1260 | 463(M⁺) 245, 161 | white powder |
| I(94) | 4-methylphenyl-cyclohexyl | 0.33 (methylene chloride: methanol = 5:1) | 7.87(2H, d), 7.41(1H, dd), 6.94(2H, dd), 6.90(1H, t), 6.74(1H, dd), 4.04(2H, t) | 3350, 3200–2300, 1630, 1600, 1540, 1500, 1450, 1245 | 449(M⁺) 406, 393, 355, 231 | white powder |
| I(95) | 4-methylphenyl-O-(thien-2-yl)ethyl | 0.34 (methylene chloride: methanol = 5:1) | 7.88(2H, dd), 7.35(1H, dd), 7.17(1H, dd), 7.01–6.84(5H, m), 6.75(1H, dd), 5.80–5.72(1H, m), 4.68(1H, dd), 4.55(1H, dd) | 3700–2200, 1640, 1610, 1540, 1500, 1470, 1260, 1180, 1100, 900, 840, 700 | 449(M⁺) 355, 231, 219, 149, 121, 111 | white powder |
| I(96) | 4-methylphenyl-O-(acetyloxyhexyl) | 0.35 (methylene chloride: methanol = 5:1) | 7.88(2H, dd), 7.34(2H, dd), 6.94(2H, dd), 6.90(1H, t), 6.76(1H, dd), 5.80–5.72(1H, m), 4.96(1H, dd), 4.55(1H, dd) | 3600–2200, 1740, 1640, 1600, 1550, 1510, 1460, 1260, 1180, 1100, 1040, 850, 780 | 481(M⁺) 263, 219, 149, 121 | white powder |
| I(97) | 4-(propenyl)phenyl-O-(acetyloxyhexyl) | 0.41 (methylene chloride: methanol = 5:1) | 7.73(1H, d), 7.47(2H, d), 7.38(1H, dd), 6.87(1H, t), 6.86(2H, d), 6.73(1H, dd), 4.06(2H, t) | 3600–2200, 1740, 1660, 1600, 1540, 1520, 1460, 1260, 1180, 1100, 1040, 970, 830 | 507(M⁺) 464, 289, 219, 121 | pale yellow powder |

TABLE VIII-continued

| Example No. | Substituent R in the general formula (Im) | Rf value in TLC (developing solvent) | NMR (δppm) | IR (νcm⁻¹) | Mass | Appearance |
|---|---|---|---|---|---|---|
| I(98) | (cyclohexyl-CH-CH₂-CH₂-O-C₆H₄-CH=CH-CH₃) | 0.30 (methylene chloride: methanol = 5:1) | 7.72(2H, d), 7.46(1H, d), 6.84(2H, d), 6.87(1H, t), 6.72(1H, dd), 6.55(1H, d), 5.80–5.66(1H, m), 4.80–4.50(2H, m) | 3400, 3200–2300, 1655, 1600, 1530, 1510, 1450, 1260 | 475(M⁺), 381, 223, 257, 147 | pale yellow powder |
| I(99) | (CH₃-C₆H₄-O-(CH₂)₅-CH=CH₂) | 0.41 (methylene chloride: methanol = 5:1) | 7.89(2H, d), 7.34(1H, dd), 6.96(2H, d), 6.91(1H, t), 6.77(1H, dd), 4.02(2H, t) | 3410, 3150–2250, 1640, 1610, 1540, 1510, 1460, 1260 | 449(M⁺), 231 | white powder |
| I(100) | (C₆H₅-(CH₂)₃-O-CH₂-CH=CH₂) | 0.33 (methylene chloride: methanol = 5:1) | 7.79(2H, dd), 7.37(1H, dd), 7.35–7.15 (5H, m), 6.95(2H, dd), 6.92(1H, t), 6.78(1H, dd), 5.82–5.73(1H, m) | 3600–2200, 1630, 1600, 1550, 1520, 1470, 1330, 1270, 1190, 1100, 1040, 850, 780, 710 | 457(M⁺), 239, 219, 121 | white powder |
| I(101) | (CH₂=CH-(CH₂)₄-CH=CH-C(=O)-O-C₆H₄-CH₃) | 0.33 (methylene chloride methanol = 5:1) | 7.96(2H, d), 7.52(1H, dd), 7.22(2H, d), 7.25–7.14(1H, m), 6.93(1H, t), 6.78 (1H, dd), 6.03(1H, d), 5.90–5.70(1H, m), 4.80–4.50(2H, m) | 3400, 3200–2300, 1730, 1630, 1595, 1530, 1200 | 463(M⁺), 339, 245, 121, 125 | white powder |
| I(102) | (CH₃)₂CH-(CH₂)₂-CH(CH₃)-(CH₂)₂-O-C₆H₄-CH₃ | 0.48 (methylene chloride methanol = 5:1) | 7.89(2H, dd), 7.38(1H, dd), 6.96(2H, dd), 6.91(1H, t), 6.76(1H, dd), 5.81–5.73 (1H, m), 4.69(1H, dd), 4.56(1H, dd) | 3600–2100, 2950, 1640, 1600, 1550, 1510, 1460, 1320, 1260, 1180, 1100, 1050, 850 | 479(M⁺), 261, 219, 121, 93 | white powder |
| I(103) | (C₆H₅-(CH₂)₃-O-C₆H₄-CH₃) | 0.27 (methylene chloride methanol = 5:1) | 7.72(1H, d), 7.50(2H, d), 7.30–7.14(5H, m), 6.90(1H, t), 6.88(2H, d), 6.74(1H, dd), 6.59(1H, d), 5.78–5.68(1H, m), 4.68(1H, dd), 4.53(1H, dd) | 3700–2100, 1660, 1600, 1540, 1510, 1450, 1270, 1180, 1100, 1030, 980, 830, 700 | 483(M⁺), 265, 219, 147, 119, 91 | pale yellow powder |

TABLE VIII-continued

| Example No. | Substituent R in the general formula (Im) | Rf value in TLC (developing solvent) | NMR (δppm) | IR (νcm⁻¹) | Mass | Appearance |
|---|---|---|---|---|---|---|
| 1(104) | 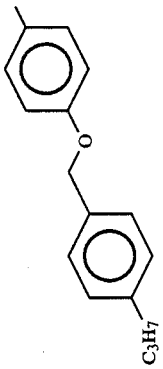 | 0.25 (methylene chloride methanol = 4:1) | (CDCl₃) 8.00(1H, s), 7.87(2H, d), 7.33(2H, d), 7.20(2H, d), 7.02(2H, d), 6.98(1H, d), 6.86(1H, t), 6.75(1H, d), 5.74(1H, m), 5.10(2H, s), 4.86(1H, dd), 4.48(1H, dd) | 3300, 2960, 2870, 1620, 1605, 1500, 1465, 1250, 1175, 110 | 471(M⁺), 428 415, 377, 351 339, 253, 223 219, 205, 149 133, 121, 91 | white powder |
| 1(105) | 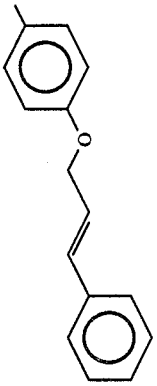 | 0.35 (methylene chloride methanol = 5:1) | 7.91(1H, d), 7.45-7.20(6H, m), 7.02(2H, d), 6.91(1H, t), 6.76(1H, dd), 6.74(1H, d), 6.39(1H, dt) | 3400, 3200-2300, 1630, 1600, 1540, 1495, 1450, 1250 | 455(M⁺), 335, 281 | pale yellow powder |
| 1(106) | 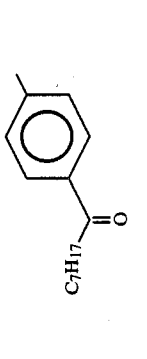 | 0.32 (methylene chloride: methanol = 5:1) | 8.06(4H, s), 7.72(1H, dd), 6.97(1H, t), 6.80(1H, dd), 5.76(1H, m), 4.65(2H, m), 3.00(2H, t) | 3300, 3200-2300, 1680, 1630, 1530, 1460, 1275 | 449(M⁺), 299, 231 | white powder |
| 1(107) | 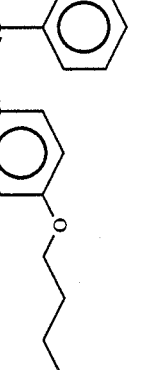 | 0.20 (chloroform: methanol = 5:1) | 8.06(4H, s), 7.35-7.60(5H, m), 7.15(1H, s), 6.96(2H, d), 6.60-6.70(5H, m), 5.80 3.89(2H, t) | 3390, 2950, 1655, 1605, 1540, 1510, 1450, 1260, 1175 | 525(M⁺), 307, 279, 195, 165, 121 | yellow powder |
| 1(108) | 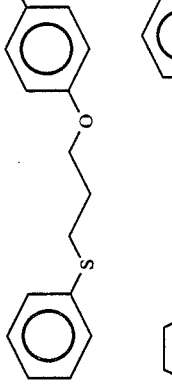 | 0.25 (methylene chloride: methanol = 5:1) | 7.88(2H, dd), 7.33(1H, dd), 7.34-7.10 (5H, m), 6.94(2H, d), 6.90(1H, t), 6.75(1H, dd), 4.12(2H, t) | 3460-2210, 1640, 1610, 1540, 1510, 1460, 1260 | 489(M⁺), 271 | white powder |
| 1(109) |  | 0.02 (chloroform: methanol = 5:1) | (CDCl₃) 8.05(1H, s), 7.86(2H, d), 7.13(1H, dd), 6.65-7.05(7H, m), 5.74(1H, m), 4.85(1H, dd), 4.49(1H, dd), 4.03(2H, m), 2.93 (2H, m), 1.90(4H, m) | 2950, 1630, 1605 1540, 1500, 1455 1255, 1175, 1090 840, 770, 690 | 477(M⁺), 307, 259 139, 121 97 | pale yellow powder |

TABLE VIII-continued

| Example No. | Substituent R in the general formula (Im) | Rf value in TLC (developing solvent) | NMR (δppm) | IR (νcm⁻¹) | Mass | Appearance |
|---|---|---|---|---|---|---|
| 1(110) | 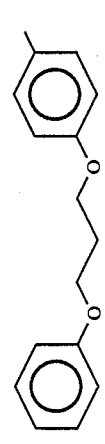 | 0.20 (chloroform: methanol = 4:1) | (CDCl₃) 7.96(1H, s), 7.85(2H, d), 7.10-7.35(3H, m), 6.70-7.00(7H, m), 5.72(1H, m), 4.86 (1H, dd), 4.47(1H, dd), 4.20(2H, t), 4.14(2H, t), 2.28(2H, m) | 3400, 2940, 2870, 2730, 1630, 1600, 1540, 1490, 1460, 1250, 1175, 1095, 1050, 760, 690 | 473(M⁺), 255, 135, 121, 107 | white powder |
| 1(111) |  | 0.30 (methylene chloride: methanol = 5:1) | 7.88(2H, d), 6.97((3H, d), 6.88(1H, t), 6.77(1H, dd), 6.35(1H, dd), 6.07(1H dd), 5.86-5.65(3H, m), 4.85(1H, dd), 4.60(2H, d), 4.52(1H, dd) | 3400, 2960, 2930, 2860, 1600, 1530, 1500, 1450, 1380, 1250 | 447(M⁺), 327, 229, 219 | white powder |
| 1(112) | 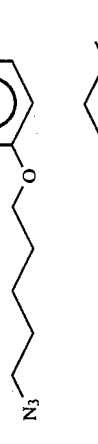 | 0.20 (chloroform: methanol = 4:1) | (CDCl₃) 7.94(1H, s), 7.87(2H, d), 6.70-7.00(5H, m), 5.74(1H, m), 4.90(1H, dd), 4.48(1H, dd), 4.02(2H, t), 3.30(2H, t), 1.10-2.20 (7H, m) | 3410, 2940, 2870, 2730, 2090, 1635, 1600, 1540, 1505, 1460, 1260, 1180, 1095, 845, 770 | 450(M⁺), 232, 121, 84 | white powder |
| 1(113) | 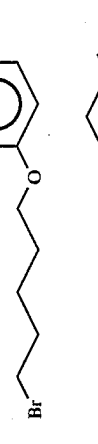 | 0.43 (methylene chloride: methanol = 5:1) | 7.89(2H, d), 7.39(1H, dd), 6.96(2H, d), 6.91(1H, t), 6.76(1H, dd), 4.04(2H, t) | 3650-3150, 2940, 1630, 1605, 1545, 1505, 1460, 1260 | (M⁺)487 269 | white powder |
| 1(114) | 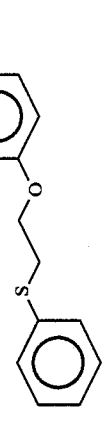 | 0.22 (methylene chloride: methanol = 5:1) | 7.87(2H, d), 7.42(1H, dd), 7.36-7.20 (5H, m), 6.90(2H, d), 6.90(1H, t), 6.76(1H, dd), 4.19(2H, t), 3.30(2H, t) | 3400, 3100-2200, 1600, 1540, 1500, 1460, 1250 | 475(M⁺) 257 | white powder |
| 1(115) | 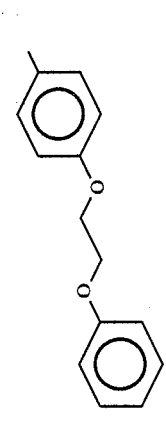 | 0.30 (methylene chloride: methanol = 5:1) | 7.92(2H, d), 7.38(1H, d), 7.30(2H, t), 5.77 7.10-6.87(6H, m), 6.77(1H, dd), 4.70(1H, dd), 4.56(1H, dd), 4.37(4H, ) | 3600-2500, 1730 1630, 1605, 1570, 1530, 1485, 1460, 1380, 1285, 1245, 1200 | 459(M⁺) 241, 218 | yellow powder |
| 1(116) |  | 0.31 (methylene chloride: methanol = 5:1) | 7.89(2H, d), 7.41(1H, dd), 6.95(2H, d), 6.91(1H, t), 6.75(1H, dd), 4.50(2H, t), 4.07(2H, t) | 3350, 2900, 1630, 1605, 1540, 1505, 1460, 1260 | decomposed | white powder |

TABLE VIII-continued

| Example No. | Substituent R in the general formula (Im) | Rf value in TLC (developing solvent) | NMR (δppm) | IR (νcm$^{-1}$) | Mass | Appearance |
|---|---|---|---|---|---|---|
| 1(117) | 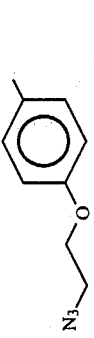 | 0.30 (methylene chloride: methanol = 5:1) | 7.92(2H, d), 7.46(1H, dd), 7.00(2H, d), 6.92(1H, t), 6.76(1H, dd), 5.76(1H, dd), 4.64(1H, dd), 4.56(1H, dd), 4.21(2H, t) | 3650–3150, 3020–2250, 2100, 1635, 1605, 1540, 1510, 1480, 1460, 1340, 1320, 1310, 1280, 1260 | 408(M$^+$) 339, 190 | white powder |
| 1(118) | 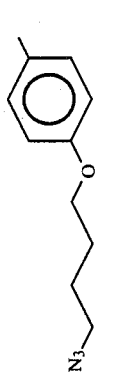 | 0.30 (methylene chloride: methanol = 5:1) | 7.90(2H, d), 7.34(1H, dd), 6.95(2H, d), 6.92(1H, t), 6.77(1H, dd), 5.77(1H, dd), 4.70(1H, dd), 4.56(1H, dd), 4.06(2H, t), 3.39(2H, t) | 3620–3150, 2920, 2100, 1605, 1540, 1505, 1460, 1260 | 436(M$^+$) 218 | white powder |
| 1(119) | 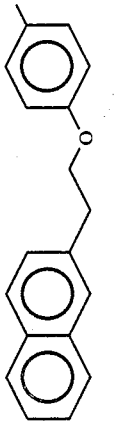 | 0.30 (methylene chloride: methanol = 5:1) | 7.86(2H, d), 7.80(3H, m), 7.72(1H, s), 7.58(1H, dd), 7.44(3H, m), 6.95(2H, d), 6.90(1H, t), 6.73(1H, dd), 5.68(1H, t), 4.55(2H, d) | 3700–2300, 1650, 1610, 1520, 1510, 1455, 1260 | 493(M$^+$), 450, 437, 399, 275 | white powder |
| 1(120) |  | 0.30 (methylene chloride: methanol = 5:1) | | | 491(M$^+$) 273, 115, 111 | white powder |
| 1(121) |  | 0.30 (methylene chloride: methanol = 5:1) | | | 505, 411, 287, 253, 121 | white powder |

EXAMPLE 1(201)–1(260)
By the same procedure as example 1, using with a corresponding carboxylic acid and a corresponding 8-amino-2-(5-tetraxzolyl)-4-oxo-4H-1-benzopyran hydrochloride which have corresponding substituent $R^3$, following compounds having the following physical data, shown in table [IX] were given.
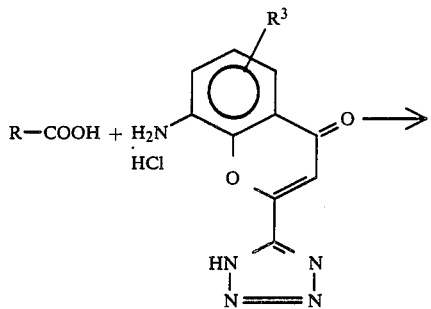
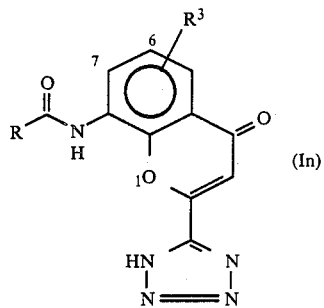
(In)

TABLE IX

| Example No. | Substituent R, R³ in the general formula (In) | Rf value in TLC (developing solvent) | NMR (δppm) | Ir (νcm⁻¹) | Mass | Appearance |
|---|---|---|---|---|---|---|
| 1(201) |  C₅H₁₁<br>R³ = H | 0.26 (chloroform: methanol = 3:1) | 8.81(1H, dd), 7.95(1H, dd), 7.76(1H, d), 7.57(2H, d), 7.52(1H, t), 7.28(1H, s), 7.25(2H, d), 7.10(1H, d), 2.66(2H, t), 1.66(2H, m), 1.20–1.50(4H, m), 0.91(8H, t) | 3310, 8060, 2980, 2850, 1620–1650, 1585, 1520, 1420, 1850, 1280, 1205, 1180, 1085, 1005, 970, 880, 810, 750 | 429(M⁺) 401, 891, 886, 875, 296, 229, 201, 181, 115 | pale brown powder |
| 1(202) |  C₅H₁₁<br>R³ = 6-Me | 0.16 (chloroform: methanol = 4:1) | 8.72(1H, d), 7.76(1H,d, 7.72(1H, m), 7.56(2H, d), 7.24(2H, d), 7.24(1H, s), 7.10(1H, d), 2.65(2H, t), 2.52(8H, s), 1.65(2H, m), 1.20–1.45(4H, m), 0.90(8H,t) | 3400, 2980, 2860, 1650, 1625, 1600, 1585, 1470, 1420, 1870, 1880, 1265, 1215, 1180, 1080, 980, 895, 860 | 448(M⁺) 415, 400, 248, 201, 181 | yellow powder |
| 1(203) |  C₅H₁₁<br>R³ = 6-F | 0.20 (chloroform: methanol = 4:1) | 8.80(1H, dd), 7.80(1H, d), 7.50–7.65 (8H, m), 7.26(1H, s), 7.24(2H, d), 7.14 (1H, d), 2.65(2H, t), 1.65(2H, m), 1.20–1.45(4H, m), 0.90(8H, t) | 3400, 2980, 2850, 1650 1620, 1500, 1520, 1470, 1420, 1875, 1825, 1175 | 419, 404, 296, 247, 201, 161, 181, 115 | yellow brown powder |
| 1(204) | <br>R³ = H | 0.15 (chloroform: methanol = 4:1) | 8.80(1H, dd), 7.90(1H, dd), 7.76(1H, d), 7.55–7.70(2H, m), 7.50(1H,t), 7.35–7.50(8H, m), 7.27(1H, s), 7.12(1H, d) | 3400, 3020, 1695, 1635, 1610, 1585, 1520, 1420, 1355, 1280, 1185, 1160, 880, 760, 550 | 359(M⁺) 381, 316, 296, 268, 229, 201, 181, 103 | yellow powder |
| 1(205) |  C₅H₁₁<br>R³ = H | 0.46 (methylene chloride: methanol = 4:1) | 8.74(1H, dd), 7.99(1H,dd), 7.97(2H, d), 7.54(1H, t), 7.88(2H, d), 7.26(1H, s), 2.78(2H, t), 0.92(3H, t) | 3500–2800, 1670, 1620 1590, 1535, 1435 | 408(M⁺), 349, 175 | white powder |
| 1(206) |  C₄H₉O<br>R³ = H | 0.46 (chloroform: methanol = 3:1) | 8.66(1H, dd), 8.02(2H, d), 7.98(1H, dd), 7.53(1H, t), 7.27(1H, s), 7.05 (2H, d), 4.08(2H, t), 1.90–1.78(2H, m), 1.64–1.44(2H, m), 1.02(3H, t) | 3600, 2300, 1645, 1600, 1585, 1580, 1505, 1425, 1385, 1290, 1255, 1180, 1070, 1030, 970, 890, 840, 810, 765 | 405(M⁺) 225, 177 | pale yellow powder |

TABLE IX-continued

| Example No. | Substituent R, $R^3$ in the general formula (In) | Rf value in TLC (developing solvent) | NMR (δppm) | Ir (νcm$^{-1}$) | Mass | Appearance |
|---|---|---|---|---|---|---|
| I(207) | 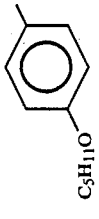 $C_5H_{11}O$  $R^3 = H$ | 0.46 (chloroform:methanol = 3:1) | 8.60(1H, dd), 8.02(2H, d), 7.98(1H, dd), 7.54(1H, t), 7.27(1H, s), 705 (2H, d), 4.08(2H, t), 1.94–1.78(2H, m), 1.60–1.25(4H, m), 0.96(3H, t) | 3600–2300, 1645, 1600, 1585, 1530, 1505, 1425, 1385, 1290, 1255, 1180, 1070, 1030, 970, 890, 840, 810, 765 | 419(M$^+$) 239, 191 | pale yellow powder |
| I(208) | 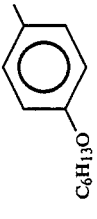 $C_6H_{13}O$  $R^3 = H$ | 0.48 (chloroform:methanol = 3:1) | 8.45(1H, dd), 8.02(2H, d), 7.98(1H, dd), 7.53(1H, t), 7.22(1H, s), 7.05 (2H, d), 4.07(2H, t), 1.90–1.75(2H, m), 1.60–1.30(6H,m), 1.00–0.90(3H, t) | 3600–2300, 1645, 1600, 1585, 1530, 1505, 1425, 1385, 1290, 1255, 1180, 1070, 1030, 970, 890, 840, 810, 765 | 433(M$^+$) 379, 205 | white powder |
| I(209) | 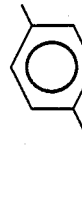 $C_7H_{15}O$  $R^3 = H$ | 0.48 (chloroform:methanol = 3:1) | 8.48(1H, dd), 8.02(2H, d), 7.98(1H, dd), 7.54(1H, t), 7.24(1H, s), 7.04 (2H, d), 4.07(2H, t), 1.90–1.75(2H, m), 1.60–1.25(8H, m), 1.00–0.75(3H, t) | 3600–2300, 1645, 1600, 1585, 1530, 1505, 1425, 1385, 1290, 1255, 1180, 1070, 1030, 970, 890, 840, 810, 765 | 447(M$^+$) 394, 219 | pale yellow powder |
| I(210) | 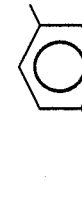 $C_9H_{19}O$  $R^3 = H$ | 0.48 (chloroform:methanol = 3:1) | 8.70(1H, dd), 8.01(2H, d), 7.97(1H, dd), 7.52(1H, t), 7.26(1H, s), 7.03 (2H, d), 4.06(2H, t), 1.90–1.76(2H, m), 1.60–1.20(12H, m), 0.96–0.84(3H, t) | 3600–2300, 1645, 1600, 1585, 1530, 1505, 1425, 1385, 1290, 1255, 1180, 1070, 1030, 970, 890, 840, 810, 765 | 475(M$^+$) 421, 247 | pale yellow powder |
| I(211) |  $C_8H_{17}O$  $R^3 = H$ | 0.48 (chloroform:methanol = 5:1) | 8.48(1H, dd), 8.02(2H, d), 7.98(1H, d), 7.53(1H, s), 7.27(1H, s), 7.04(2H, d), 4.06(2H, t), 1.90–1.75(2H, m), 1.60–1.20(10H, m), 1.00–0.75(3H, t) | 3600–2300, 1645, 1600, 1585, 1530, 1505, 1425, 1385, 1290, 1255, 1180, 1070, 1030, 970, 890, 840, 810, 765 | 461(M$^+$) 407, 233 | pale yellow powder |
| I(212) |   $R^3 = H$ | 0.30 (methylene chloride:methanol = 4:1) | 8.74(1H, dd), 8.01(2H, d), 7.96(1H, dd), 7.52(1H, t), 7.24(1H, s), 7.05 (2H, d), 6.00–5.64(3H, m), 5.10–4.90 (2H, m), 4.58(2H, brd) | 3275, 3075, 3500–2300, 1650, 1630, 1600, 1570, 1510, 1495, 1420, 1250 | 457(M$^+$) 337, 229 121 | pale brown powder |

TABLE IX-continued

| Example No. | Substituent R, R³ in the general formula (In) | Rf value in TLC (developing solvent) | NMR (δppm) | Ir (νcm⁻¹) | Mass | Appearance |
|---|---|---|---|---|---|---|
| 1(213) | (geranyloxy-phenyl structure); R³ = H | 0.30 (methylene chloride:methanol = 4:1) | 8.66(1H, dd), 8.02(2H, d), 7.96(1H, dd), 7.53(1H, t), 7.26(1H, s), 7.06(2H, d), 5.60–5.44(1H, m), 5.20–5.00(1H, m) | 3275, 3050, 3500–2300, 1640, 1590, 1570, 1510, 1490, 1415, 1240 | 485(M⁺), 365,350 231 | pale brown powder |
| 1(214) | (2-butenyl-phenoxy-hexyl structure); R³ = H | 0.44 (chloroform:methanol = 4:1) | (1H, dd), 7.94(1H, dd), 7.76(1H, d), 7.58(2H, d), 7.50(1H, t), 7.24(1H, s), 6.99(1H, d), 6.94(2H, d), 4.01(2H, t), 1.90–1.74(2H, m), 1.60–1.30(6H, m), 0.92(3H, t) | 3600–2300, 1640, 1600, 1535, 1430, 1390, 1355, 1190, 1170, 1110, 825, 755 | 495(M⁺) 231 | pale yellow powder |
| 1(215) | (2-butenyl-phenoxy-pentyl structure); R³ = H | 0.44 (chloroform:methanol = 4:1) | 8.82(1H, dd), 7.94(1H, dd), 7.74(1H, d), 7.61(2H, d), 7.52(1H, t), 7.28(1H, s), 7.04(1H, d), 6.96(2H, d), 4.04(2H, t), 1.90–1.76(2H, m), 1.60–1.26(8H, m), 0.92(3H, t) | 3600–2300, 1640, 1600, 1535, 1430, 1390, 1355, 1335, 1260, 1190, 1170, 1110, 1070, 1040, 1010, 975, 825, 755 | 473(M⁺) 245 | pale yellow powder |
| 1(216) | (2-butenyl-phenoxy-isobutyl structure); R³ = H | 0.42 (chloroform:methanol = 4:1) | 8.84(1H, dd), 7.95(1H, dd), 7.75(1H, d), 7.60(2H, d), 7.52(1H, t), 7.29(1H, s), 7.04(1H, d), 6.96(2H, d), 4.02(2H, t), 1.90–1.76(2H, m), 1.72–1.56(1H, m), 1.46–1.24(4H, m), 0.06(6H, d) | 3600–2300, 1640, 1600, 1535, 1430, 1360, 1260, 1170, 1040, 1010, 825, 755 | 459(M⁺) 261, 231 | pale yellow powder |
| 1(217) | Cl—(CH₂)₅—O—(2-butenyl-phenyl); R³ = H | 0.43 (chloroform:methanol = 4:1) | 8.88(1H, dd), 7.94(1H, dd), 7.75(1H, d), 7.49(2H, d), 7.50(1H, t), 7.26(1H, s), 7.02(1H, d), 6.93(2H, d), 4.04(2H, t), 3.59(2H, t), 1.96–1.89(4H, m), 1.86–1.60(2H, m) | 3600–2300, 1645, 1600, 1530, 1430, 1395, 1260, 1170, 1110, 1070, 1040, 1010, 975, 825, 755 | 443 425, 251 | yellow powder |

TABLE IX-continued

| Example No. | Substituent R, R³ in the general formula (In) | Rf value in TLC (developing solvent) | NMR (δppm) | Ir (νcm⁻¹) | Mass | Appearance |
|---|---|---|---|---|---|---|
| 1(218) | Cl—(CH₂)₆—O—C₆H₄—CH=CH—CH₃ ; R³ = H | 0.43 (chloroform: methanol = 4:1) | 8.86(1H, dd), 7.94(1H, dd), 7.74(1H, d), 7.59(2H, d), 7.51(1H, t), 7.26(1H, s), 7.03(1H, d), 6.96(2H, d), 4.04(2H, t), 3.58(2H, t), 1.94–1.86(4H, m), 1.60–1.50(4H, m) | 3600–2300, 1645, 1600, 1530, 1430, 1370, 1360, 1260, 1170, 1110, 1070, 1040, 1010, 975, 825, 755 | 493(M⁺) 457, 439 265 | yellow powder |
| 1(219) | (p-pentyl-styryl phenyl); R³ = H | 0.43 (chloroform: methanol = 4:1) | 8.86(1H, dd), 7.96(1H, dd), 7.78(1H, d), 7.56(2H, d), 7.52(1H, t), 7.28(1H, s), 7.25(2H, d), 7.14(1H, d), 2.68(2H, t), 1.72–1.56(2H, m), 1.48–1.26(2H, m), 0.96(3H, t) | 3600–2300, 1640, 1585, 1520, 1430, 1380, 1350, 1280, 1180, 1110, 1070, 1040, 1010, 975, 890, 820, 755 | 415 (M⁺) 231, 187 | pale brown powder |
| 1(220) | C₆H₁₃—C₆H₄—CH=CH—; R³ = H | 0.43 (chloroform: methanol = 4:1) | 8.86(1H, dd), 7.95(1H, dd), 7.78(1H, d), 7.57(2H, d), 7.2 7.28(1H, s), 7.24(2H, d), 7.11(1H, d), 2.66(2H, t), 1.74–1.56(2H, m), 1.44–1.24(6H, m), 0.89(3H, t) | 3600–2300, 1640, 1590, 1520, 1425, 1385, 1350, 1280, 1080, 1110, 1065, 1040, 1005, 975, 890, 890, 755 | 443(M⁺) 215 | white powder |
| 1(221) | C₇H₁₅—C₆H₄—CH=CH—; R³ = H | 0.43 (chloroform: methanol = 4:1) | 8.84(1H, dd), 7.95(1H, dd), 7.76(1H, d), 7.58(2H, d), 7.52(1H, t), 7.28(1H, s), 7.20(2H, dd), 7.14(1H, d), 2.65 (2H, t), 1.74–1.58(2H, m), 1.40–1.20 (8H, m), 0.88(3H, t) | 3500–2300, 1640, 1584, 1520, 1430, 1350, 1180, 1110, 1040, 1005, 975, 885 | 457(M⁺) 229 | white powder |
| 1(222) | C₆H₁₃—CH=CH—CH₂—O—C₆H₄(p-CH₃); R³ = H | 0.30 (methylene chloride: methanol = 4:1) | 8.72(1H, dd), 8.00(2H, d), 7.95(1H, dd), 7.50(1H, t), 7.23(1H, s), 7.04 (2H, d), 6.00–5.60(2H, m), 4.56(2H, brd) | 3300, 3500–2300, 1640, 1595, 1570, 1515, 1490, 1415, 1240 | 473(M⁺) 353, 245 121 | brown powder |
| 1(223) | C₅H₁₁—C≡C—CH₂—O—C₆H₄(p-CH₃); R³ = H | 0.30 (methylene chloride: methanol = 4:1) | 8.74(1H, dd), 8.02(2H, d), 7.96(1H, dd), 7.50(1H, t), 7.23(1H, s), 7.10 (2H, d), 4.77(2H, t) | 3375, 3050, 3500–2300, 1640, 1590, 1570, 1510, 1490, 1415, 1240 | 457(M⁺) 429, 229 175, 121 | pale brown powder |

TABLE IX-continued

| Example No. | Substituent R, R³ in the general formula (In) | Rf value in TLC (developing solvent) | NMR (δppm) | Ir (νcm⁻¹) | Mass | Appearance |
|---|---|---|---|---|---|---|
| 1(224) | 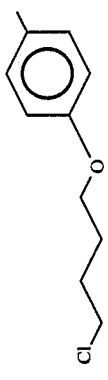 R³ = H | 0.41 (methylene chloride: methanol = 4:1) | 8.65(1H, dd), 8.01(2H, d), 7.96(1H, dd), 7.52(1H, t), 7.25(1H, s), 7.04 (2H, d), 4.16–4.06(2H, m), 3.70–3.60 (2H, m), 2.10–1.96(4H, m) | 3600–2300, 1650, 1600, 1585, 1530, 1505, 1430, 1380, 1295, 1255, 1180, 1115, 1070, 1035, 890, 845, 815, 765, 750 | 211 | white powder |
| 1(225) | 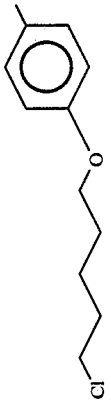 R³ = H | 0.41 (methylene chloride: methanol = 4:1) | 8.62(1H, dd), 8.02(2H, d), 7.98(1H, dd), 7.53(1H, t), 7.26(1H, s), 7.05 (2H, d), 4.10(2H, t), 3.60(2H, t), 2.00–1.80(4H, m), 1.80–1.60(2H, m) | 3600–2300, 1650, 1600, 1585, 1530, 1505, 1430, 1380, 1295, 1255, 1180, 1115, 1070, 1035, 895, 845, 815, 765, 760 | 453($M^+$) 417, 225 | white powder |
| 1(226) |  R³ = H | 0.44 (methylene chloride: methanol = 4:1) | 8.64(1H, dd), 8.02(2H, d), 7.98(1H, dd), 7.53(1H, t), 7.26(1H, s), 7.04 (2H, d), 4.08(2H, t), 3.58(2H, t), 1.96–1.78(4H, m), 1.62–1.50(4H, m) | 3600–2300, 1650, 1600, 1585, 1530, 1505, 1430, 1380, 1295, 1255, 1180, 1115, 1070, 1035, 890, 845, 815, 765, 750 | 467($M^+$) 431, 239 | white powder |
| 1(227) | 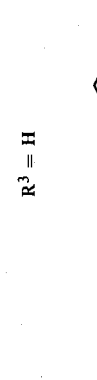 R³ = H | 0.30 (methylene chloride: methanol = 4:1) | 8.73(1H, dd), 8.01(2H, d), 7.96(1H, dd), 7.52(1H, t), 7.24(1H, s), 7.05 (2H, d), 6.00–5.60(2H, m), 4.58(2H, d) | 3500–2300, 1640, 1620, 1600, 1580, 1520, 1500, 1420, 1245 | 459($M^+$) 339, 231 | pale brown powder |
| 1(228) | 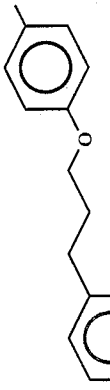 R³ = H | 0.38 (chloroform: methanol = 4:1) | 8.58(1H, dd), 8.01(2H, d), 7.98(1H, dd), 7.53(1H, t), 7.32–7.16(5H, m), 7.26(1H, s), 7.03(2H, d), 4.06(2H, t), 2.84(2H, t), 2.14–2.06(2H, m) | 3600–2300, 1645, 1600, 1580, 1525, 1505, 1425, 1380, 1290, 1255, 1180, 1060, 1030, 885, 835, 810, 760, 740 | 467($M^+$) 413, 239 | white powder |

TABLE IX-continued

| Example No. | Substituent R, R³ in the general formula (In) | Rf value in TLC (developing solvent) | NMR (δppm) | Ir (νcm⁻¹) | Mass | Appearance |
|---|---|---|---|---|---|---|
| I(229) | 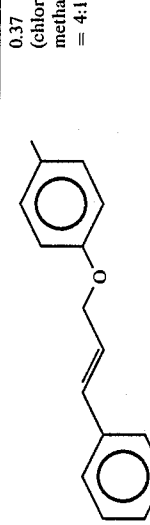<br>R³ = H | 0.37 (chloroform: methanol = 4:1) | 8.64(1H, dd), 8.04(2H, d), 7.98(1H, dd), 7.54(1H, t), 7.48–7.26(5H, m), 7.27(1H, s), 7.12(2H, d), 6.80(1H, d), 6.44(1H, d), 4.83(2H, dd) | 3600–2300, 1645, 1600, 1580, 1520, 1500, 1425, 1375, 1290, 1250, 1175, 970, 885, 840, 810, 765, 745 | 465(M⁺) 345, 237 | pale brown powder |
| I(230) | 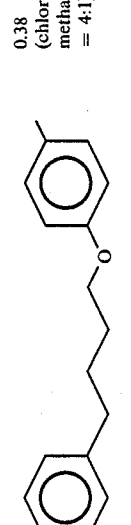<br>R³ = H | 0.38 (chloroform: methanol = 4:1) | 8.57(1H, dd), 8.02(2H, d), 7.98(1H, dd), 7.54(1H, t), 7.30–7.15(5H, m), 7.26(1H, s), 7.04(2H, d), 4.14–4.04 (2H, m), 2.76–2.68(2H, m), 1.90–1.80 (4H, m) | 3600–2300, 1645, 1600, 1580, 1525, 1505, 1425, 1380, 1290, 1255, 1180, 1060, 1030, 885, 835, 810, 760, 740 | 480(M⁺) 423, 253 | pale brown powder |
| I(231) | 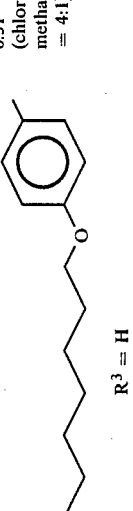<br>R³ = H | 0.31 (chloroform: methanol = 4:1) | 8.74(1H, dd), 8.01(2H, d), 7.96(1H, dd), 7.52(1H, t), 7.24(1H, s), 7.03 (2H, d), 5.95–5.72(1H, m), 5.10–4.90 (2H, m), 4.06(2H, t) | 3100–2300, 1640, 1610, 1595, 1575, 1515, 1495, 1420, 1245 | 459(M⁺) 231, 121 | pale brown powder |
| I(232) | 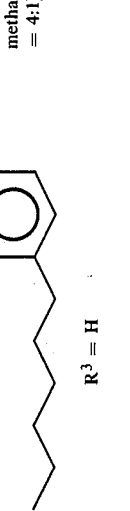<br>R³ = H | 0.43 (chloroform: methanol = 4:1) | 8.60(1H, dd), 8.00(1H, dd), 7.97(2H, d), 7.54(1H, t), 7.38(2H, d), 7.28 (1H, s), 2.73(2H, t), 1.80–1.60(2H, m), 1.42–1.22(8H, m), 0.89(3H, t) | 3600–2300, 1645, 1620, 1585, 1520, 1425, 1375, 1290, 1065, 1030, 1015, 890, 810, 765, 750 | 417(M⁺) 363, 189 | white powder |
| I(233) | <br>R³ = H | 0.43 (chloroform: methanol = 4:1) | 8.56(1H, dd), 8.00(1H, dd), 7.97(2H, d), 7.54(1H, t), 7.37(2H, d), 7.20 (1H, s), 2.13(2H, t), 1.78–1.60(2H, m), 1.44–1.26(6H, m), 0.90(3H, t) | 3600–2300, 1645, 1620, 1585, 1525, 1425, 1375, 1290, 1065, 1030, 1015, 890, 765, 750 | 431(M⁺) 377, 203 | pale brown powder |
| I(234) | <br>R³ = H | 0.43 (chloroform: methanol = 4:1) | 8.68(1H, dd), 7.99(1H, dd), 7.96(2H, d), 7.54(1H, t), 7.37(2H, d), 7.27 (1H, s), 2.72(2H, t), 1.76–1.60(2H, m), 1.42–1.32(10H, m), 0.88(3H, t) | 3600–2300, 1645, 1620, 1585, 1525, 1425, 1375, 1290, 1065, 1030, 1015, 890, 765, 750 | 445(M⁺) 391, 217 | pale yellow powder |

TABLE IX-continued

| Example No. | Substituent R, R³ in the general formula (In) | Rf value in TLC (developing solvent) | NMR (δppm) | Ir (νcm⁻¹) | Mass | Appearance |
|---|---|---|---|---|---|---|
| I(235) |  R³ = H | 0.43 (chloroform: methanol = 4:1) | 8.65(1H, dd), 8.00(1H, dd), 7.96(2H, d), 7.54(1H, t), 7.38(2H, d), 7.27 (1H, s), 2.73(2H, t), 1.76-1.60(2H, m), 1.44-1.24(12H, m), 0.88(3H, t) | 3600-2300, 1645, 1620, 1585, 1525, 1425, 1375, 1290, 1065, 1030, 1015, 890, 810, 765, 750 | 431(M⁺) 405, 231 | pale yellow powder |
| I(236) |  R³ = H | 0.29 (methylene chloride methanol = 4:1) | 8.73(1H, dd), 8.01(2H, d), 7.96(1H, dd), 7.51(1H, t), 7.23(1H, s), 7.13 (1H, dd), 7.02(2H, d), 6.92(1H, dd), 6.83(1H, brs) | 3600-2300, 1640, 1610, 1595, 1570, 1510, 1490, 415, 1250 | 487(M⁺) 433, 259 | pale brown powder |
| I(237) | 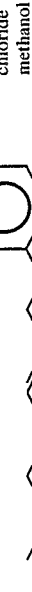 R³ = H | 0.30 (methylene chloride methanol = 4:1) | 8.64(1H, dd), 7.92(2H, d), 7.88(1H, dd), 7.18(1H, s), 6.98(2H, d), 7.44 (1H, t), 6.00-5.60(2H, m), 4.55(2H, brd) | 3600-2300, 1640, 1610, 1590, 1570, 1510, 1490, 1420, 1245 | 445(m⁺) 325, 231 217, 189 121 | white powder |
| I(238) |  R³ = H | 0.30 (methylene chloride methanol = 4:1) | 8.70(1H, dd), 8.00(2H, d), 7.95(1H, dd), 7.50(1H, t), 7.24(1H, s), 7.04 (2H, d), 6.00-5.60(2H, m), 4.57(2H, d) | 3600-2300,1645, 1620, 1595, 1575, 1520, 1495, 1420, 1240 | 431(M⁺) 331, 203 121 | pale yellow powder |
| I(239) |  R³ = 6-F | 0.45 (chloroform: methanol = 4:1) | 8.53(1H, dd), 8.00(2H, d), 7.57(1H, dd), 7.24(1H, s), 7.05(2H, d), 5.98-5.64(3H, m), 5.06-4.90(2H, m), 4.60 (2H, d), 2.20-2.00(4H, m), 1.60-1.44 (2H, m) | 3600-2300, 1650, 1600, 1510, 1480, 1435, 1390, 1260, 1180, 900, 865 | 475(M⁺) 355, 244 | yellow powder |
| I(240) |  R³ = 6-F | 0.45 (chloroform) | 8.50(1H, dd), 8.00(2H, d), 7.58(1H, dd), 7.24(1H, s), 7.04(2H, d), 4.07 (2H, t), 1.90-1.85(2H, m), 1.60-1.25 (8H, m), 0.90(3H, t) | 3600-2300, 1655, 1600, 1510, 1475, 1430, 1380, 1260, 1180, 1035, 1015, 895, 870 | 465(M⁺) 229 | yellow powder |

TABLE IX-continued

| Example No. | Substituent R, R³ in the general formula (In) | Rf value in TLC (developing solvent) | NMR (δppm) | Ir (νcm⁻¹) | Mass | Appearance |
|---|---|---|---|---|---|---|
| I(241) | [structure: 4-methylphenyl-O-(CH₂)₃-CH(phenyl)-], R³ = 6-CH₃ | 0.51 (chloroform:methanol = 4:1) | 8.52(1H, d), 7.96(2H, d), 7.70(1H, d), 7.21(5H, m), 7.16(1H, s), 6.97(2H, d), 4.04(2H, t), 2.69(2H, t), 2.48(3H, s), 1.84(4H, m) | 3600–2300, 1645, 1600, 1530, 1505, 1250, 1180, 1030, 890, 860, 840, 760 | 441, 253 | pale brown powder |
| I(242) | [structure with C₅H₁₁-CH=CH-CH₂-O-(4-methylphenyl)], R³ = 6-CH₃ | 0.32 (chloroform:methanol = 3:1) | 8.58(1H, d), 8.00(2H, d), 7.73(1H, d), 7.20(1H, s), 7.03(2H, d), 5.60–6.00 (2H, m), 4.56(2H, d), 2.52(3H, s), 2.10(2H, m) | 2930, 2860, 1650, 1605, 1600, 1535, 1510, 1460, 1260, 1180, 1040, 900, 770 | 473(M⁺) 354, 231, 121, 110, 91 | yellow powder |
| I(243) | [structure: thiophene-CH=CH-CH₂-O-(4-methylphenyl)], R³ = 6-CH₃ | 0.32 (chloroform:methanol = 3:1) | 8.56(1H, d), 7.98(2H, d), 7.71(1H, d), 7.17(1H, s), 7.12(1H, d), 6.99(2H, d), 6.91(1H, dd), 6.80(1H, d), 4.06(2H, m), 2.92(2H, m), 2.50(3H, s), 1.88(4H, m) | 2930, 1650, 1605, 1595, 1535, 1510, 1450, 1260, 1180, 1035 | 501(M⁺) 477, 259 139, 121 97 | yellow brown powder |
| I(244) | [structure: C₈H₁₇O-(phenyl)], R³ = 6-CH₃ | 0.32 (chloroform:methanol = 3:1) | 8.54(1H, d), 8.00(2H, d), 7.74(1H, d), 7.22(1H, s), 7.02(2H, d), 4.05(2H, t), 2.54(3H, s) | 2920, 2850, 1650, 1605, 1595, 1530, 1505, 1465, 1255, 1180, 1030, 840, 760 | 475(M⁺) 421, 233 121 | yellow brown powder |
| I(245) | [structure: C₇H₁₅O-(phenyl)], R³ = 6-CH₃ | 0.32 (chloroform:methanol = 3:1) | 8.53(1H, d), 7.98(2H, d), 7.73(1H, d), 7.20(1H, s), 7.02(2H, d), 4.05(2H, t), 2.51(3H, s) | 2930, 2850, 1650, 1605, 1595, 1535, 1510, 1470, 1260, 1180, 1035, 895, 765 | 461(M⁺) 407, 219 121 | yellow brown powder |
| I(246) | [structure: CH₂=CH-(CH₂)₄-O-(4-methylphenyl)], R³ = 6-CH₃ | 0.25 (methylene chloride:methanol = 5:1) | 8.62(1H, d), 7.99(2H, d), 7.73(1H, d), 7.18(1H, s), 7.01(2H, d), 5.92–5.70(1H, m), 5.04–4.92(2H, m), 4.04(2H, t) | 3460, 3070, 2930, 1650, 1610, 1530, 1510, 1260 | 473(M⁺) 231 | white powder |

TABLE IX-continued

| Example No. | Substituent R, R³ in the general formula (In) | Rf value in TLC (developing solvent) | NMR (δppm) | Ir (νcm⁻¹) | Mass | Appearance |
|---|---|---|---|---|---|---|
| I(247) | [4-methylphenyl-O-CH₂-CH=CH-CH=CH-CH=CH₂ structure]; R³ = 6-CH₃ | 0.28 (chloroform methanol = 5:1) | 8.42(1H, s), 7.85(2H, d), 7.60(1H, s), 7.06(1H, s), 6.91(2H, d), 5.90–5.50 (3H, m), 5.00–4.82(2H, m), 4.47(2H, d) | 3600–2300, 1650, 1600, 1535, 1505, 1450, 1370, 1330, 1310, 1250, 1180 | 471(M⁺) 351, 257 243, 229 | yellow powder |
| I(248) | [4-methylphenyl-O-(CH₂)₆-Cl structure]; R³ = 6-CH₃ | 0.30 (methylene chloride: methanol = 4:1) | 8.60(1H, brs), 8.03(2H, d), 7.78(1H, brs), 7.26(1H, s), 7.08(2H, d), 4.21(2H, t), 3.72(2H, t), 2.68(3H, s) | 3600–2300, 1650, 1600, 1590, 1530, 1505, 1450, 1255 | 446 243, 241 239, 121 | pale yellow powder |
| I(249) | [4-methylphenyl-O-(CH₂)₆-Cl structure]; R³ = H | 0.30 (methylene chloride: methanol = 4:1) | 8.73(1H, dd), 8.00(2H, d), 7.95(1H, dd), 7.51(1H, t), 7.24(1H, s), 7.03 (2H, d), 4.05(2H, t) | 3600–2300, 1640, 1600, 1580, 1520, 1500, 1420 | 445 427, 255 253, 121 | pale brown powder |
| I(250) | [4-methylphenyl-O-(CH₂)₇-Cl structure]; R³ = 6-CH₃ | 0.48 (methylene chloride: methanol = 5:1) | 8.52(1H, d), 8.00(2H, d), 7.75(1H, d), 7.22(1H, s), 7.04(2H, d), 3.55(2H, t) | 3600–3150, 3060, 2920, 2850, 1650, 1605, 1530, 1510, 1450, 1370, 1260 | 473 267 | yellow brown powder |
| I(251) | [4-methylphenyl-O-(CH₂)₇-Cl structure]; R³ = 6-CH₃ | 0.31 (methylene chloride: methanol = 4:1) | 8.57(1H, d), 7.98(2H, d), 7.72(1H, d), 7.19(1H, s), 7.01(2H, d), 4.04(2H, t), 3.54(2H, t) | 3600–2300, 1650, 1600, 1590, 1530, 1505, 1255 | 459 253, 181 169, 121 | pale brown powder |

TABLE IX-continued

| Example No. | Substituent R, R³ in the general formula (In) | Rf value in TLC (developing solvent) | NMR (δppm) | Ir (νcm⁻¹) | Mass | Appearance |
|---|---|---|---|---|---|---|
| 1(252) | [structure: Cl-phenyl-(CH₂)ₙ-O-phenyl-CH₃]; R³ = H | 0.30 (methylene chloride: methanol = 5:1) | 8.61(1H, d), 8.02(2H, d), 7.98(1H, d), 7.54(1H, t), 7.05(2H, d), 4.08(2H, t), 3.55(2H, t) | 3450, 2920, 2850, 1650, 1580, 1520, 1500, 1430, 1290, 1250, 1180 | 459, 267 | brown powder |
| 1(253) | [structure: dichlorophenyl-allyl-O-phenyl-CH₃]; R³ = 6-Cl | 0.45 (chloroform: methanol = 4:1) | 8.69(1H, d), 8.00(2H, d), 7.89(1H, d), 7.24(1H, s), 7.04(2H, d), 5.96-5.64 (3H, m), 5.60-4.90(2H, m), 4.60(2H, d), 2.10-2.00(4H, m), 1.60-1.42(2H, m) | 3600-2300, 1650, 1600, 1580, 1500, 1460, 1410, 1365, 1255, 1175, 1030, 1000, 890, 870, 760 | 493(M⁺), 491, 371 | pale yellow powder |
| 1(254) | [structure: dichlorophenyl-(CH₂)₂-O-phenyl-CH₃]; R³ = H | 0.20 (methylene chloride: methanol = 5:1) | 8.53(1H, dd), 7.94(2H, d), 7.90(1H, dd), 7.44(1H, t), 7.28(1H, d), 7.26(1H, s), 7.17(1H, s), 7.01(1H, dd), 6.96(2H, d), 3.99(2H, t), 2.74(2H, t), 2.05(2H, m) | 3450, 3070, 2920, 1640, 1600, 1580, 1520, 1500, 1470, 1420, 1380, 1340, 1290, 1250, 1180, 1030 | 307 | brown powder |
| 1(255) | [structure: naphthyl-(CH₂)₂-O-phenyl-CH₃]; R³ = 6-CH₃ | 0.25 (methylene chloride: methanol = 5:1) | 8.51(1H, d), 8.00(2H, dt), 7.90~7.70(5H, m), 7.54~7.35(3H, m), 7.21(1H, s), 7.05(2H, dt), 4.38(2H, t) | 3650~2200, 1640, 1610, 1510, 1470, 1260, 1180, 1020, 890, 850, 820, 760, 600 | 275, 155, 121 | pale yellow powder |
| 1(256) | [structure: dichlorophenyl-(CH₂)₂-O-phenyl-CH₃]; R³ = 6-CH₃ | 0.26 (methylene chloride: methanol = 5:1) | 8.55(1H, d), 8.00(2H, dt), 7.76~7.72(1H, m), 7.35 (1H, d), 7.32(1H, d), 7.06(1H, dd), 7.01(2H, dt), 4.04(2H, t) | 3650~2100, 1650, 1610, 1540, 1510, 1470, 1390, 1260, 1180, 1130, 1030, 940, 890, 860, 840, 770 | 307, 121 | yellow powder |
| 1(257) | [structure: naphthyl-(CH₂)₂-O-phenyl-CH₃]; R³ = H | 0.23 (methylene chloride: methanol = 5:1) | 8.76(1H, dd), 8.01(2H, d), 7.96(1H, dd), 7.80(4H, m), 7.47(4H, m), 7.23(1H, s), 7.06(2H, d), 4.38(2H, t), 3.11(2H, t) | 3400, 3050, 1650, 1600, 1580, 1500, 1430, 1370, 1340, 1250, 1160, 1060, 1020, 880, 850, 810, 750 | 275 | yellow powder |

TABLE IX-continued
| Example No. | Substituent R, R³ in the general formula (In) | Rf value in TLC (developing solvent) | NMR (δppm) | Ir (νcm⁻¹) | Mass | Appearance |
|---|---|---|---|---|---|---|
| 1(258) | <br>R³ = H— | 0.19 (methylene chloride: methanol = 5:1) | | | 287 | pale brown powder |
| 1(259) | 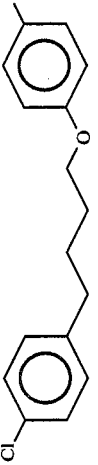<br>R³ = 6-CH₃— | 0.23 (methylene chloride: methanol = 5:1) | | | 287 | brown powder |
| 1(260) | <br>R³ = 6-CH₃— | 0.28 (methylene chloride: methanol = 5:1) | | | 273, 121 | dark yellow powder |

EXAMPLE 1(301)–1(302)

By the same procedure as example 1, using with p-pentylcinnamic acid and 8-amino-2-(5-tetrazolyl)-2,3-dihydro-1,4-dithianphthalene hydrochloride or 5-amino-2-(5-tetrazolyl)-2,3-dihydro-1,4-dithianaphthalene hydrochloride, following compounds having the following physical data, shown in table [X] were given.

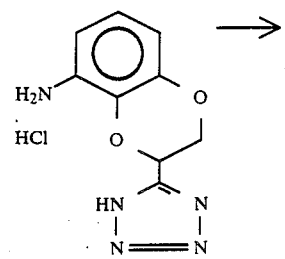

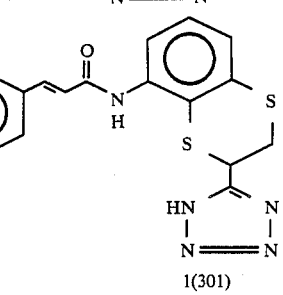

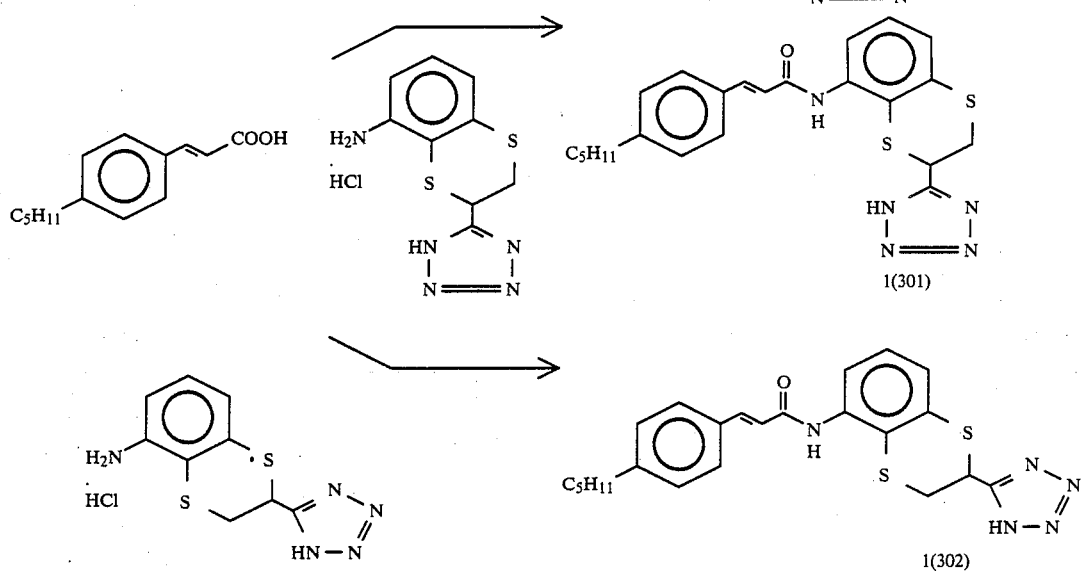

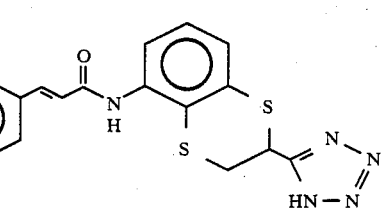

TABLE X

| Example No. | Rf value in TLC (developing solvent) | NMR (δppm) | IR (νcm⁻¹) | Mass | Appearance |
|---|---|---|---|---|---|
| 1(301) | 0.33 (chloroform: methanol = 3:1) | 7.76(1H, d), 7.55(2H, d), 7.44–7.10 (3H, m), 7.24(2H, d), 6.73(1H, d), 5.15(1H, m), 3.66(2H, m), 2.64 (2H, t), 0.90 (3H, t) | 3500–2300, 1660, 1620, 1610, 1565, 1510, 1180, 980 | 451(M⁺) 408.372 357.355 338.201 | white powder |
| 1(302) | 0.23 (chloroform: methanol = 3:1) | 7.72(1H, d), 7.51(2H, d), 7.22(2H, d) 7.60–7.10(3H, m), 6.71(2H, d), 5.40–5.26(1H, m), 3.56–3.40(2H, m), 2.68(2H, t), 1.64(2H, t), 0.90(3H, t) | 3500–2800, 1660 1620, 1610, 1560, 1510 | 201, 198 | white powder |

EXAMPLE 1(401)

By the same procedure as example 1, using with p-heptyloxybenzodithioic acid and 8-amino-2-(5-tetrazolyl)-1,4-benzodioxane hydrochloride, following compound having following phsyical data was given.

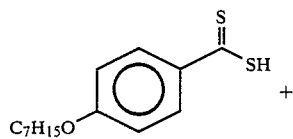

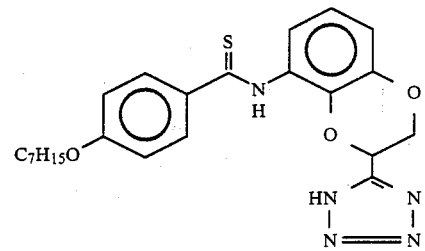

TLC : Rf 0.14 (chloroform: methanol=17:3);

NMR : δ7.87(2H, d), 7.77(1H, m), 6.90(4H, m), 5.74(1H, m), 4.58(2H, m), 3.98(2H, t), 1.78(2H, m), 1.30(8H, m), 0.88(3H, t);

IR : ν3600–2400, 1600, 1495, 1450, 1255, 1170, 1090, 1005, 960, 830 cm⁻¹;

Mass: m/e 453(M+), 420, 354, 326, 235, 219, 137, 121;

Appearance: orange powder.

EXAMPLE 1(501)–1 (526)

By the same procedure as example 1, using a corresponding carboxylic acid and a corresponding amine, following compounds having the following physical data, shown in table [XI] were given.

TABLE XI

| Example No. | Formula | Rf value in TLC (developing solvent) | NMR (δppm) | IR (νcm$^{-1}$) | Mass | Appearance |
|---|---|---|---|---|---|---|
| 1(501) | (structure with OC$_6$H$_{13}$) | 0.38 (methylene chloride:methanol = 4:1) | 8.00(2H, d), 7.98(1H, d), 7.59(1H, s), 7.50(1H, dd), 7.33(1H, t), 7.01(2H, d), 4.04(2H, t) | 3430, 2920, 2840, 1640, 1610, 1530, 1500, 1420, 1250 | 405(m$^+$), 205 | white powder |
| 1(502) | (structure with OC$_7$H$_{15}$) | 0.34 (methylene chloride:methanol = 5:1) | 8.00(2H, d), 7.97(1H, dd), 7.59 (1H, s), 7.50(1H, dd), 7.32(1H, t), 4.04(2H, t), 7.01(2H, d) | 3430, 2920, 2840, 1640, 1610, 1530, 1500, 1420, 1250 | 433(m$^+$), 233 | white powder |
| 1(503) | (structure with OC$_8$H$_{17}$) | 0.38 (methylene chloride:methanol = 4:1) | 8.00(2H, d), 8.00(1H, d), 7.58 (1H, s), 7.50(1H, dd), 7.33(1H, t), 7.01(2H, d), 4.04(2H, t) | 3430, 2920, 2840, 1640, 1610, 1530, 1500, 1420, 1250 | 419(m$^+$), 219 | yellow powder |
| 1(504) | (structure with OC$_9$H$_{19}$) | 0.35 (methylene chloride:methanol = 5:1) | 7.99(2H, d), 7.97(1H, d), 7.58 (1H, s), 7.49(1H, d), 7.31(1H, t), 7.00(2H, d), 4.04(2H, t) | 3430, 2920, 2840, 1640, 1610, 1530, 1500, 1420, 1250 | 447(m$^+$), 247 | brown powder |

TABLE XI-continued

| Example No. | Formula | Rf value in TLC (developing solvent) | NMR (δppm) | IR (νcm⁻¹) | Mass | Appearance |
|---|---|---|---|---|---|---|
| 1(505) | [structure with O-C$_6$H$_{13}$] | 0.38 (methylene chloride: methanol = 4:1) | 7.94(2H, dd), 7.40(1H, d), 7.09 (1H, dd), 6.97(2H, dd), 6.96(1H, t), 6.21(1H, dd), 4.02(2H, t), 3.88(1H, dd), 3.50(1H, dd) | 3720, 3020, 2920, 2850, 2730, 1640, 1610, 1520, 1500, 1440, 1310, 1250 | 407(m⁺), 205 | white powder |
| 1(506) | [structure with O-C$_7$H$_{15}$] | 0.38 (methylene chloride: methanol = 5:1) | 7.94(2H, dd), 7.34(1H, d), 7.11 (1H, dd), 6.98(2H, dd), 6.97(1H, t), 6.22(1H, dd), 4.03(2H, t), 6.89 (1H, dd), 6.50(1H, dd) | 3270, 3020, 2920, 2850, 2730, 1640, 1610, 1520, 1500, 1440, 1310, 1250 | 421(m⁺), 219 | white powder |
| 1(507) | [structure with O-C$_8$H$_{17}$] | 0.38 (methylene chloride: methanol = 4:1) | 7.94(2H, dd), 7.41(1H, d), 7.09 (1H, dd), 6.98(2H, dd), 6.97(1H, t), 6.21(1H, dd), 4.02(2H, t), 3.88(1H, dd), 3.51(1H, dd) | 3720, 3020, 2920, 2850, 2730, 1640, 1610, 1520, 1500, 1440, 1310, 1250 | 435(m⁺), 233 | white powder |
| 1(508) | [structure with O-C$_9$H$_{19}$] | 0.39 (methylene chloride: methanol = 4:1) | 7.95(2H, dd), 7.41(1H, dd), 7.10 (1H, dd), 6.99(2H, dd), 6.98(1H, t), 6.22(1H, dd), 4.04(2H, t), 3.89(1H, dd), 3.51(1H, dd) | 3720, 3020, 2920, 2850, 2730, 1640, 1610, 1520, 1500, 1440, 1310, 1250 | 449(m⁺), 247 | white powder |

TABLE XI-continued

| Example No. | Formula | Rf value in TLC (developing solvent) | NMR (δppm) | IR (νcm⁻¹) | Mass | Appearance |
|---|---|---|---|---|---|---|
| 1(509) | (structure with OCH₂Ph group) | 0.30 (methylene chloride:methanol = 5:1) | 7.97(2H, d), 7.88(1H, d), 7.48(1H, d), 7.38~7.14(7H, m), 6.97(2H, d) | 3700~2100, 1650, 1610, 1500, 1420, 1390, 1350, 1300, 1260, 1220, 1180, 1070, 1020, 850, 740 | 453(m⁺), 253, 121 | white powder |
| 1(510) | (structure with allyl ether) | 0.34 (methylene chloride:methanol = 5:1) | 7.97(2H, d), 7.88(1H, d), 7.47(1H, d), 7.36~7.32(2H, m), 7.00(2H, d), 5.98~5.64(3H, m), 5.10~4.92(2H, m), 4.55(2H, d) | 3600~2100, 1640, 1600, 1500, 1430, 1390, 1350, 1300, 1260, 1190, 1060, 1000, 920, 840, 750 | 429(m⁺), 229, 201, 121 | white powder |
| 1(511) | (structure with O–C₆H₁₂Cl) | 0.40 (methylene chloride:methanol = 5:1) | 8.00(2H, d), 7.95(1H, dd), 7.49(1H, dd), 7.31(1H, t), 7.29(1H, s), 7.00(2H, dt), 4.05(2H, t) | 3500~2100, 1640, 1610, 1500, 1420, 1290, 1260, 1200, 1110, 1050, 840, 740 | 439(m⁺), 239, 121 | white powder |

TABLE XI-continued

| Example No. | Formula | Rf value in TLC (developing solvent) | NMR (δppm) | IR (νcm⁻¹) | Mass | Appearance |
|---|---|---|---|---|---|---|
| 1(512) | (structure with C₇H₁₅) | 0.32 (chloroform: methanol = 5:1) | 7.87(2H, d), 7.33(2H, m), 6.92(2H, d), 6.83(1H, t), 6.66(1H, dd), 3.98(2H, t), 1.78(2H, m), 1.30(8H, m), 0.88(3H, m) | 3650~2400, 1640, 1605, 1500, 1445, 1250 | 325, 219 | pale brown powder |
| 1(513) | (structure with C₆H₁₃) | 0.09 (chloroform: methanol = 9:1) | 7.85(2H, d), 7.30(2H, m), 6.88(2H, d), 6.80(10H, t), 6.62(1H, d), 3.96(2H, d), 1.77(2H, m), 1.34(6H, m), 0.88(3H, t) | 3600~2500, 1630, 1600, 1495, 1440, 1240 | 205, 121 | pale brown powder |
| 1(514) | (naphthalene structure with OCH₂Ph) | 0.40 (chloroform: methanol = 5:1) | 8.57(1H, s), 8.07(1H, d), 8.02(2H, d), 7.93(1H, d), 7.82(1H, d), 7.75(1H, d), 7.54(1H, t), 7.30–7.18(5H, m), 6.98(2H, d), 4.04(2H, t) | 3400, 2910, 1615, 1605, 1560, 1480, 1380, 1300, 1280, 1250, 1170, 1060, 830, 750 690 | 463(m⁺), 420, 253 | yellow powder |

TABLE XI-continued

| Example No. | Formula | Rf value in TLC (developing solvent) | NMR (δppm) | IR (νcm⁻¹) | Mass | Appearance |
|---|---|---|---|---|---|---|
| 1(515) | (structure) | 0.17 (methylene chloride: ethyl acetate = 2:1) | 8.84(1H, dd), 8.40(1H, d), 8.28(1H, d) 7.96(2H, d), 7.64~7.56(2H, m), 6.99(2H, d), 5.80–5.56(3H, m), 4.98–4.88(2H, m), 4.50(2H, d), 2.12–1.94(4H, m), 1.52–1.36(2H, m) | 3600–2300, 1635, 1600, 1530, 1510, 1250, 1175, 840, 760 | 548, 440(m⁺), 412, 332, 320 | yellow powder |
| 1(516) | (structure) | 0.18 (methylene chloride: ethyl acetate = 2:1) | 8.93(1H, dd), 8.48(1H, d), 8.38(1H, d), 8.04(2H, d), 7.76–7.64(2H, m), 7.32–7.16 (5H, m), 7.04(2H, d), 4.09(2H, t), 2.72 (2H, t), 1.94–1.80(14H, m) | 3600–2300, 1635, 1605, 1530, 1505, 1250, 1170, 835, 760 | | pale yellow powder |
| 1(517) | (structure) | 0.47 (methylene chloride: methanol = 5:1) | 8.03(1H, dd), 7.93(2H, d), 7.36–7.14 (5H, m), 7.04(1H, t), 6.96(2H, d), 6.83 (1H, dd), 5.45(1H, dd), 4.60(1H, dt), 4.15(1H, dt) | 3400–2300, 1645, 1610, 1510, 1480, 1450, 1260, 1060 | 485(m⁺), 442, 439, 411, 377, 359 | white powder |

TABLE XI-continued
| Example No. | Formula | Rf value in TLC (developing solvent) | NMR (δppm) | IR (νcm$^{-1}$) | Mass | Appearance |
|---|---|---|---|---|---|---|
| 1(518) | 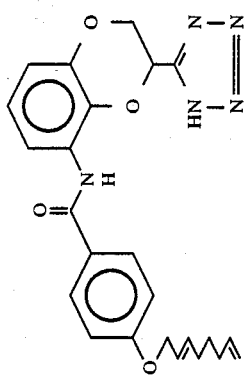 | 0.49 (methylene chloride: methanol = 5:1) | 8.01(1H, dd), 7.93(2H, d), 7.03(1H, t), 6.97(2H, d), 6.82(1H, dd), 5.96–5.60 (2H, m), 5.45(1H, dd), 5.07–6.90(2H, m), 4.62(1H, dt), 4.15(1H, dt), 4.53(2H, d) | 3260, 3200–2300, 1645 1610, 1500, 1475, 1450, 1255 | 461, 405, 353, 341 | white powder |
| 1(519) | 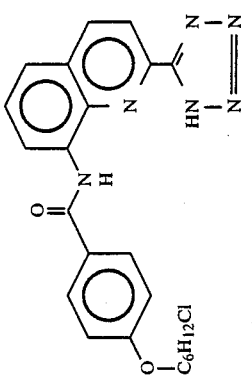 $C_6H_{12}Cl$ | 0.18 (methylene chloride: ethyl acetate = 2:1) | 8.95(1H, dd), 8.49(1H, d), 8.38(1H, d), 8.06(2H, d), 7.78–7.66(2H, m), 7.06(2H, d), 4.10(2H, t), 3.58(2H, t), 2.00–1.78 (4H, m), 1.70–1.50(4H, m) | 3600–2300, 1635, 1600 1530, 1510, 1255, 1175, 840, 765 | | yellow powder |
| 1(520) | 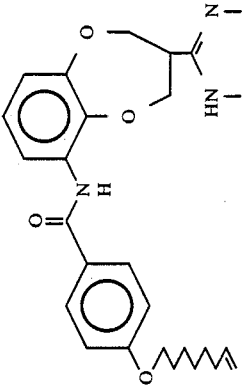 | 0.20 (chloroform: methanol = 4:1) | 8.00(1H, dd), 7.93(2H, d), 7.04(1H, t), 6.95(2H, d), 6.83(1H, dd), 5.81(1H, m), 5.45(1H, dd), 5.00(2H, m), 4.60(1H, m), 4.18(1H, m), 4.00(2H, t), 2.74(2H, m), 2.07(2H, m), 1.80(2H, m), 1.42(6H, m) | 3200, 2930, 2860, 1605, 1565, 1530, 1505, 1470, 1450, 1250, 1060 | 463(m$^+$), 407, 231, 121, 93 | yellow powder |

TABLE XI-continued

| Example No. | Formula | Rf value in TLC (developing solvent) | NMR (δppm) | IR (νcm$^{-1}$) | Mass | Appearance |
|---|---|---|---|---|---|---|
| 1(521) | | 0.55 (methylene chloride: methanol = 5:1) | 7.88(2H, d), 7.54(1H, m), 7.34–7.12 (5H, m), 7.00–6.86(4H, m), 5.73(1H, dd) 4.02(2H, t) | 3300–2200, 1610, 1530, 1510, 1460, 1260 | 468(m$^+$), 441, 426, 413, 395, 253 | white powder |
| 1(522) | | 0.42 (methylene chloride: methanol = 5:1) | 7.88(2H, d), 7.50(1H, m), 7.00–6.88 (4H, m), 5.92–5.66(2H, m), 5.06–4.90 (2H, m), 4.02(2H, t) | 3400–2300, 1610, 1570, 1530, 1505, 1460, 1260 | 447(m$^+$), 253, 231 | white powder |
| 1(523) | | 0.25 (methylene chloride: methanol = 5:1) | 7.91(2H, d), 7.35–7.10(6H, m), 6.95 (2H, d), 6.94(1H, t), 6.78(1H, dd), 4.03(2H, t) | 3400, 3100–2300, 1660, 1610, 1580, 1530, 1500, 1450, 1250 | 253, 225, 121 | pale brown powder |

| Example No. | Formula | Rf value in TLC (developing solvent) | NMR (δppm) | IR (νcm$^{-1}$) | Mass | Appearance |
|---|---|---|---|---|---|---|
| 1(524) | (structure with C$_5$H$_{11}$-phenyl-CH=CH-C(=O)-NH-benzofuran-tetrazole) | 0.25 (methylene chloride:methanol = 5:1) | 8.15(1H, d), 7.78(1H, d), 7.65–7.20 (8H, m), 6.90(1H, d), 2.66(2H, t), 0.92(3H, t) | 3300, 1630, 1530, 1200, 740 | 401(m$^+$), 373, 372, 358, 344 | pale brown powder |
| 1(525) | (structure with C$_5$H$_{11}$-phenyl-CH=CH-C(=O)-NH-benzodioxole) | 0.27 (chloroform:methanol = 3:1) | 7.68(1H, d), 7.44(2H, d), 7.40(1H, s), 7.25(1H, d), 7.18(2H, d), 6.90(1H, t), 6.73(1H, d), 6.65(1H, t), 2.62(2H, t), 1.62(2H, m), 1.20–1.45(4H, m), 0.89(3H, t) | 3250, 2930, 2850, 1660, 1620, 1600, 1525, 1445, 1340, 1255, 1180, 1070, 980, 825, 765, 710 | 405, 349, 336, 325, 306, 201, 131, 115 | pale brown powder |
| 1(526) | (structure with Cl-(CH$_2$)$_6$-O-phenyl-C(=O)-NH-naphthalene-tetrazole) | 0.40 (methylene chloride:methanol = 5:1) | 8.31(1H, s), 7.94(2H, d), 7.86(1H, d), 7.72(1H, d), 7.68(1H, d), 7.57(1H, d), 7.41(1H, t), 6.90(2H, d), 3.96(2H, d), 3.55(2H, t) | 3400, 2920, 1615, 1605, 1480, 1300, 1250, 1170, 830, 750 | 239 | yellow powder |

EXAMPLE 2

Synthesis of 8-(3-methoxy-4-pentyloxycinnamoyl)amino-2-(5-tetrazolyl)-1,4-benzodioxane

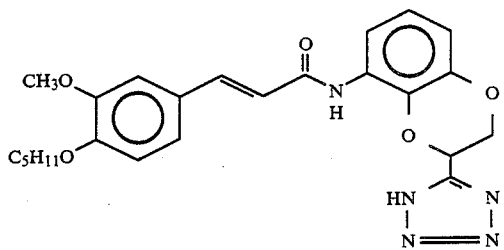

Sodium azide (490 mg) and pyridinium chloride (870 mg) were added to a solution of 8-(3-methoxy-4-pentyloxycinnamoyl)amino-1,4-benzodioxane (560 mg; synthesized in reference example 2) in dry dimethylformamide (3 ml). In an atmosphere of argon, the solution was stirred for 1.5 hrs at 100° C. The reaction solution cooled to room temperature was poured into 1N hydrochloric acid, and the mixture was extracted with ethyl acetate. The extract was washed with water and a saturated aqueous solution of sodium chloride, dried, and then concentrated under reduced pressure. The residue was recrystallized from ethyl acetate to give the title compound (390 mg) having the following physical data:

TLC : Rf 0.10 (chloroform: methanol=5:1);

NMR : δ7.69(1H, d), 7.68(1H, s), 7.05–7.25(2H, m), 6.80–7.00(2H, m), 6.74(1H, m), 6.65(1H, d), 5.73(1H, m), 4.69(1H, dd), 4.51(1H, dd), 4.05(2H, t), 3.92(3H, s), 1.87(2H, m), 1.30–1.55(4H, m), 0.94(3H, t);

IR : ν2940, 2850, 1655, 1600, 1540, 1505, 1450, 1260 cm$^{-1}$;

Mass: m/e 465(M+), 247, 177, 145.

EXAMPLE 2(1)–2(46)

By the same procedures as reference example 1, 2 and example 1, using a corresponding carboxylic acid and 3-aminopyrocatechol, following compounds having the following physical data, shown in table [XII] were given.

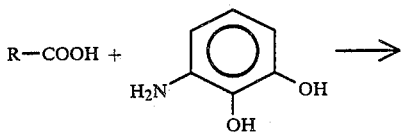

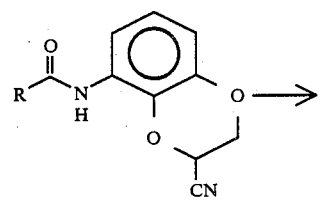

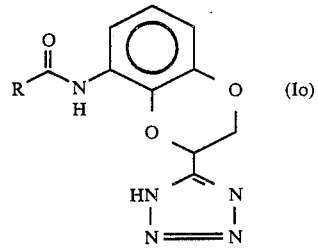 (Io)

TABLE XII

| Example No. | Substituent R in the general formula (Io) | Rf value in TLC (developing solvent) | NMR (δppm) | IR (νcm$^{-1}$) | Mass | Appearance |
|---|---|---|---|---|---|---|
| 2(1) | 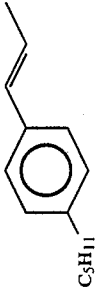 C$_5$H$_{11}$ | 0.28 (methylene chloride: methanol = 5:1) | 7.72(1H,m),7.46(2H,d), 7.18(2H,dd),6.88(1H,d), 6.72(1H,dd),5.67(1H,dd), 2.62(2H,t),1.62(2H,m),1.20–1.45 (4H,m),0.88(3H,t) | 3250,2930,2860 1660,1610,1540 1260,1200,1100 965,775,715 | 419(M$^+$) 219,201 131 | white powder |
| 2(2) | 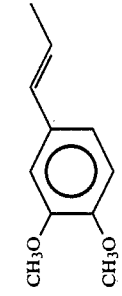 CH$_3$O, CH$_3$O | 0.3 (methylene chloride: methanol = 4:1) | (DMSO—d$_6$) 9.24(1H,s),7.78(1H,d),7.15– 7.30(2H,m),7.00(1H,d)6.94(1H,d)6.87 (1H,t),6.68(1H,dd),6.00(1H,dd),4.68(1H, dd),4.49(1H,dd),3.82(3H,s),3.80(3H,s) | 1660,1600,1540 1510,1480,1450 | 409(M$^+$) 366,353 315,296 258,233 219,191 | pale yellow powder |
| 2(3) | 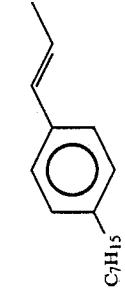 C$_7$H$_{15}$ | 0.3 (methylene chloride: methanol = 5:1) | 8.02(1H,s),7.80(1H,d),7.35–7.50(2H, m),7.24(1H,d)7.20–7.35(2H,m),6.83 (1H,5),6.72(1H,d),6.62(1H,d),5.73 (1H,m),4.72(1H,dd),4.56(1H,dd) | (liquid film) 1650, 1610,1540,1480 1450 | 447(M$^+$) 419,404 391,353 334,229 219 | white powder |
| 2(4) | 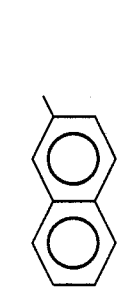 | 0.3 (methylene chloride: methanol = 5:1) | 8.46(1H,s),7.8–8.1(4H,m),7.5–7.7 (3H,m),6.94(1H,t),6.78(1H,dd), 5.78(1H,dd),4.52–4.74(2H,m) | 1620,1605,1540, 1500,1450,1430 | 373(M$^+$) 331,296 223,155 | white powder |
| 2(5) | 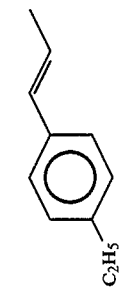 C$_2$H$_5$ | 0.3 (methylene chloride: methanol = 5:1) | (CDCl$_3$) 7.85(1H,d),7.4–7.55(2H,m),7.34(1H, s),7.15–7.30(2H,m),6.7–6.9(3H,m), 6.56(1H,dd),5.78(1H,m),4.98(1H,dd), 4.50(1H,dd),2.68(2H,q),1.25(3h,t) | 1650,1605,1530 1475,1450 | 377(M$^+$) 219,159 129 | pale yellow powder |
| 2(6) | 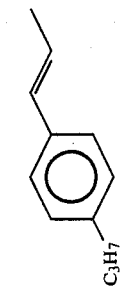 C$_3$H$_7$ | 0.3 (methylene chloride: methanol = 5:1) | 7.64(1H,d),7.40–7.55(2H,m),7.10– 7.25(2H,m)6.98(1H,dd),6.86(1H,t), 6.76(1H,dd),6.57(1H,d),5.78(1H,m), 4.90(1H,dd),4.52(1H,d) | 1660,1650,1530 1480,1445 | 391(M$^+$) 219,173 131,115 | pale yellow powder |
| 2(7) | 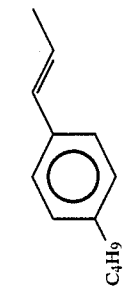 C$_4$H$_9$ | 0.3 (methylene chloride: methanol = 5:1) | 7.82(1H,d),7.40–7.55(2H,m),7.1–7.25 (2H,m),7.11(1H,d),6.85(1H,t), 6.74(1H,dd),6.59(1H,d),5.76(1H,m), 4.81(1H,d),4.54(1H,d) | 1660,1605,1535 1480,1450 | 405(M$^+$) 219,187 131 | pale yellow powder |
| 2(8) | 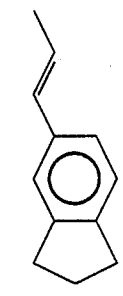 | 0.3 (methylene chloride: methanol = 5:1) | 7.76(1H,d),7.52(1H,d),7.40(1H,s) 7.32(1H,d),7.20(1H,d),6.89(1H,t), 6.73(1H,dd),6.65(1H,d),5.72(1H,dd), 4.64(1H,dd),4.54(1H,dd) | 1650,1605,1540 1470,1450 | 389(M$^+$) 276,219 171,143 128,115 | pale brown powder |

TABLE XII-continued

| Example No. | Substituent R in the general formula (Io) | Rf value in TLC (developing solvent) | NMR (δppm) | IR (νcm⁻¹) | Mass | Appearance |
|---|---|---|---|---|---|---|
| 2(9) | 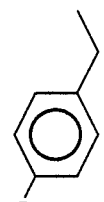 C₅H₁₁ | 0.45 (methylene chloride: methanol = 5:1) | (CDCl₃) 7.23(5H,m),6.77(3H,m),5.75(1H,t), 4.93(1H,dd),4.46(1H,dd),3.76(2H,s), 2.61(2H,t),1.61(2H,m),1.33(4H,m), 0.88(3H,t) | 3600–2300,1660 1620,1605,1550 1465,1270,1205, 1090,780 | 407(M⁺) 219,188 161 | yellow powder |
| 2(10) | 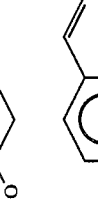 C₅H₁₁O | 0.20 (chloroform: methanol = 4:1) | (CDCl₃) 8.0(1H,s),7.80(2H,d),6.7-7.1(5H,m), 5.75(1H,m),4.85(1H,dd),4.50(1H, dd),4.00(2H,t) | 2950,1640,1610 1540,1510,1460 1260,1180,1100, 845,780 | 409(M⁺) 366,259 191,121 | white powder |
| 2(11) | 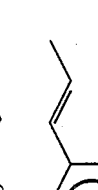 C₅H₁₁O | 0.20 (chloroform: methanol = 4:1) | 7.86(1H,s),7.76(1H,d),7.39(2H,d), 7.17(1H,d),6.70(2H,d),6.76(1H,t), 6.66(1H,dd),6.48(1H,d),5.69(1H,dd), 4.66(1H,dd),4.51(1H,dd),3.92(2H,t) | 2950,1655,1600, 1535,1505,1450, 1250,1165,1100, 960,820,770 | 435(M⁺) 392,259 217,147 119 | pale yellow powder |
| 2(12) | 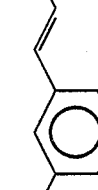 C₅H₁₁ | 0.55 (methylene chloride: methanol = 4:1) | 8.09(1H,d),7.77(2H,d),7.23(3H,m), 6.92(1H,m),6.71(2H,m),5.73(1H,dd), 4.69(1H,dd),4.49(1H,dd),2.78(2H,t), 1.58(2H,m),1.34(4H,m),0.83(3H,t) | 3600–2200,1660 1620,1605,1555 1450,1270,1200 1105,970,780 760 | 419(M⁺) 219,201 | white powder |
| 2(13) | 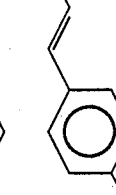 C₈H₁₇ | 0.71 (methylene chloride: methanol = 4:1) | 7.72(1H,d),7.76(1H,dd),7.28(4H,m), 6.90(1H,t),6.76(1H,d),6.73(1H,dd), 5.72(1H,dd),4.67(1H,dd),4.49(1H,dd), 2.61(2H,t),1.62(2H,m),1.26(10H,m), 0.87(3H,t) | 3600–2300,1660 1650,1555,1460 1260,1190,1100 980,960,775 | 461(M⁺) 243,219 | white powder |
| 2(14) | 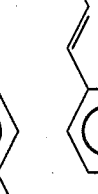 C₆H₁₃ | 0.30 (methylene chloride: methanol = 4:1) | 7.76(1H,d),7.52(1H,d),7.47(2H,d), 7.19(2H,d),6.90(1H,t),6.75(1H,dd), 6.67(1H,d),5.72(1H,dd),4.70–4.50 (2H,m) | 3300–2300,1670, 1625,1555,1470 | 433(M⁺) 219,215 | white crystal |
| 2(15) | 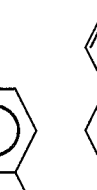 C₉H₁₉ | 0.30 (methylene chloride: methanol = 4:1) | 7.75(1H,d),7.52(1H,d),7.46(2H,d), 7.17(2H,d),6.88(1H,t),6.75(1H,dd), 6.66(1H,d),5.70(1H,dd),4.80–4.45 (2H,m) | 3300–2300,1675, 1635,1620,1560, 1465,1270 | 475(M⁺) 257,219 | white crystal |
| 2(16) | 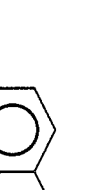 C₈H₁₇ | 0.30 (methylene chloride: methanol = 5:1) | 7.76(1H,d),7.53(1H,d),7.46(2H,d), 7.18(2H,d),6.89(1H,t),6.74(1H,dd), 6.68(1H,d),4.72(1H,dd) | 3500–2300,1665, 1630,1615,1550, 1460,1260 | 461(M⁺) 243,219 | white crystal |

TABLE XII-continued

| Example No. | Substituent R in the general formula (Io) | Rf value in TLC (developing solvent) | NMR (δppm) | IR (νcm$^{-1}$) | Mass | Appearance |
|---|---|---|---|---|---|---|
| 2(17) | ⌬–C$_8$H$_{17}$ | 0.52 (methylene chloride: methanol = 17:3) | 7.72(3H,m),7.33(2H,m),6.88(1H,t), 6.73(1H,dd),5.60(1H,dd),4.51(2H,t), 2.65(2H,t),1.62(2H,m),1.28(10H,m), 0.87(3H,t) | 3650–2700,2920, 2840,1650,1605, 1520,1450,1260, 1080,900,870 | 218,217 | pale yellow powder |
| 2(18) | ⌬–C$_5$H$_{11}$ | 0.40 (methylene chloride: methanol = 17:3) | 7.98(1H,m),7.50(1H,m),7.39(1H,m), 7.30(3H,m),6.94(1H,t),6.79(1H,dd), 5.74(1H,m),4.62(2H,m),2.83(2H,t), 1.65(2H,m),1.28(4H,m),0.86(3H,m) | 3600–2300,1660, 1640,1610,1520, 1480,1450,1260, 1100,775 | 393(M$^+$) 219,175 | yellow powder |
| 2(19) | CH$_3$O–⌬–C$_5$H$_{11}$O | 0.10 (chloroform: methanol = 5:1) | (CDCl$_3$) 7.92(1H,s),7.40–7.60(2H,m),7.10–7.25 (1H,m),6.70–7.00(4H,m),5.77(1H,t),4.97 (1H,dd),4.50(1H,dd),4.07(2H,t),3.94(3H, s),1.88(2H,m),1.30–1.60(4H,m),0.94(3H,t) | 2930,1630,1600, 1580,1540,1505, 1460,1340,1265 | 439,341 221,151 123 | white powder |
| 2(20) | ⌬–OC$_5$H$_{11}$ | 0.10 (chloroform: methanol = 5:1) | (CDCl$_3$) 7.98(1H,s),7.30–7.55(3H,m),7.05–7.20(1H, m),6.70–7.00(3H,m),5.77(1H,t),4.95(1H, dd),4.50(1H,dd),4.02(2H,t),1.82(2H,m), 1.25–1.60(4H,m),0.94(3H,t) | 2950,1635,1605, 1580,1540,1450, 1335,1260,1230, 1085,780 | 409(M$^+$) 259,191 138,121 93 | white powder |
| 2(21) | ⌬–OC$_5$H$_{11}$ with CH=CHCH$_3$ | 0.10 (chloroform: methanol = 5:1) | (CDCl$_3$) 7.70–7.90(2H,m),6.50–7.50(9H,m), 5.74(1H,m),4.80(1H,m),4.52(1H,m), 3.93(2H,t),1.78(2H,m),1.20–1.60 (4H,m),0.93(3H,t) | 2950,2860,1660, 1600,1540,1450, 1260,1195,1100, 1050,970,780 | 435(M$^+$) 219,217 191,175 147 | white powder |
| 2(22) | ⌬–OC$_5$H$_{11}$ | 0.10 (chloroform: methanol = 5:1) | (CDCl$_3$)10.03(1H,d),8.35(1H,dd),7.50 (1H,m),7.25(1H,s),7.15(1H,m),7.03(1H, d),6.70–6.95(3H,m),5.75(1H,t),4.98(1H, dd),4.50(1H,dd),4.20(2H,t),1.90(2H,m), 1.20–1.60(4H,m),0.90(3H) | 3320,2950,2860 1640,1610,1545, 1460,1300,1235 1085,775,760 | 409(M$^+$) 367,191 149,121 | white powder |
| 2(23) | ⌬–OC$_5$H$_{11}$ with CH=CHCH$_3$ | 0.10 (chloroform: methanol = 5:1) | (CDCl$_3$)8.11(1H,d),7.40–7.60(2H,m),7.20– 7.40(1H,m),7.02(1H,d),6.65–6.95(5H,m), 5.76(1H,t),4.85(1H,m),4.52(1H,m),4.00 (2H,t),1.85(2H,m),1.20–1.60(4H,m), 0.92(3H,t) | 2950,2860,1655, 1610,1540,1480, 1450 | 435(M$^+$) 407,348 341,219 217,147 | white powder |

TABLE XII-continued

| Example No. | Substituent R in the general formula (Io) | Rf value in TLC (developing solvent) | NMR (δppm) | IR (νcm⁻¹) | Mass | Appearance |
|---|---|---|---|---|---|---|
| 2(24) | 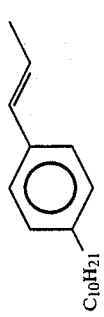 | 0.30 (chloroform: methanol = 5:1) | 7.77(1H,d),7.65(1H,d),7.50(2H,d), 7.22(2H,d),6.93(1H,t),6.76(1H,dd), 6.73(1H,d),5.74(1H,dd),4.69(1H,dd), 4.54(1H,dd) | 3300-2500,1670, 1630,1620,1555, 1460,1260 | 489(M⁺) 271,219 | white crystal |
| 2(25) | 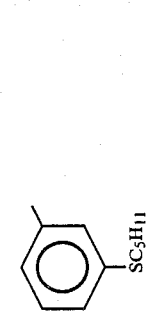 | 0.37 (methylene chloride: methanol = 17:3) | 7.86(1H,s),7.68(1H,dd),7.42(4H,m), 6.92(1H,m),6.77(1H,dd),5.75(1H,dd), 4.61(2H,m),2.98(2H,t),1.67(2H,m), 1.38(4H,m),0.89(3H,t) | 3600-2300,1640, 1610,1540,1455, 1340,1270,1260, 1090,770 | 425(M⁺) 207 | white powder |
| 2(26) | 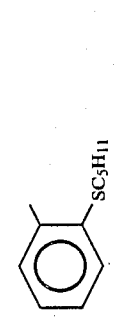 | 0.47 (methylene chloride: methanol = 17:3) | 7.81(1H,d),7.26(4H,m),6.91(1H,t), 6.77(1H,dd),5.75(1H,dd),4.69(1H,dd), 4.58(1H,dd),2.92(2H,t),1.60(2H,,m), 1.32(4H,m),0.86(3H,t) | 3600-2300,1640, 1610,1540,1460, 1320,1260,1090, 780,740 | 425(M⁺) 219,207 | yellow powder |
| 2(27) | 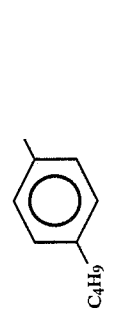 | 0.14 (chloroform: methanol = 4:1) | (CDCl₃) 7.92(1H,s),7.85(2H,d),7.30(2H,d),6.70- 7.00(3H,m),5.76(1H,t),4.95(1H,dd),4.50 (1H,dd),2.70(2H,t),1.50-1.80(2H,m), 1.20-1.50(2H,m),0.94(3H,t) | 2930,2850,1610, 1535,1460,1330, 1280,1260,1090 | 379(M⁺) 229,161 118,91 | white powder |
| 2(28) | 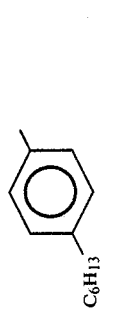 | 0.14 (chloroform: methanol = 4:1) | (CDCl₃) 8.12(1H,s),7.82(2H,d),7.26(2H,d),6.70- 7.10(3H,m),5.72(1H,t),4.83(1H,dd),4.47 (1H,dd),2.66(2H,t),1.62(2H,m),1.10- 1.45(6H,m),0.88(3H,t) | 2930,2850,1640, 1610,1545,1455, 1330,1280,1260, 1090,770 | 407(M⁺) 257,189 118,91 | white powder |
| 2(29) | 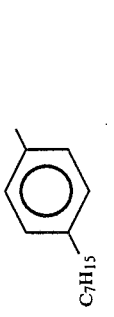 | 0.14 (chloroform: methanol = 4:1) | (CDCl₃) 8.04(1H,s),7.83(2H,d),7.28(2H,d),6.70- 7.10(3H,m),5.74(1H,t),4.85(1H,dd),4.48 (1H,dd),2.67(2H,t),1.63(2H,m),1.10- 1.45(8H,m),0.88(3H,t) | 2930,2850,1640, 1620,1550,1460, 1340,1280,1270, 1100 | 421(M⁺) 271,203 131,118 91 | white powder |
| 2(30) | 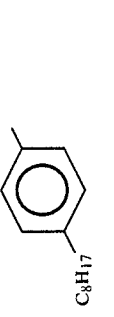 | 0.14 (chloroform: methanol = 4:1) | (CDCl₃) 8.07(1H,s0,7.83(2H,d),7.27(2H,d),6.70- 7.10(3H,m),5.74(1H,t),4.85(1H,dd),4.48 (1H,dd),2.67(2H,t),1.63(2H,m),1.10- 1.45(10H,m),0.88(3H,t) | 2930,2850,1640, 1620,1550,1460, 1340,1280,1270, 1100 | 435(M⁺) 285,217 131,118 91 | pale yellow powder |

TABLE XII-continued

| Example No. | Substituent R in the general formula (Io) | Rf value in TLC (developing solvent) | NMR (δppm) | IR (νcm⁻¹) | Mass | Appearance |
|---|---|---|---|---|---|---|
| 2(31) | 4-(N-pentyl-aminomethyleneoxy)phenyl-propenyl | 0.14 (chloroform: methanol = 4:1) | (CDCl₃)7.81(1H,d),7.50(1H,s),7.47 (2H,d),6.70–7.10(5H,m),6.48(1H,d), 5.76(1H,m),4.86(1H,dd),4.70(2H,m), 4.53(1H,dd),2.22(2H,t),1.60(1H,s),1.50 (2H,m),1.15–1.45(4H,m),0.87(3H,t) | 2930,2860,1660, 1600,1540,1505, 1450,1260,1170, 1100,1000,960, 825,775 | 473(M⁺) 255,219 147,119 | white powder |
| 2(32) | 3-(SC₅H₁₁)phenyl-propenyl | 0.46 (methylene chloride: methanol = 17:3) | 7.69(1H,d),7.44(1H,m),7.28(3H,m) 6.86(1H,t),6.71(1H,dd),6.68(1H,d), 5.69(1H,t),4.60(2H,m),2.91(2H,t), 1.64(2H,m),1.36(4H,m),0.88(3H,t) | 3600–2200,1650, 1605,1540,1450, 1260,1190,1090, 960,780,770 | 451(M⁺) 233,219 | white powder |
| 2(33) | 2-(SC₅H₁₁)phenyl-propenyl | 0.36 (methylene chloride: methanol = 17:3) | 8.29(1H,d),7.51(2H,m),7.28(3H,m), 6.86(1H,t),6.71(1H,dd),6.62(1H,d), 5.71(1H,dd),4.60(2H,m),2.88(2H,t), 1.62(2H,m),1.36(4H,m),0.88(3H,t) | 3600–2300,1660, 1620,1555,1450, 1265,1200,1105, 970,780,760 | 451(M⁺) 348 | pale yellow powder |
| 2(34) | 4-isopropylphenyl-propenyl | 0.49 (methylene chloride: methanol = 17:3) | 7.74(1H,d),7.48(3H,m),7.24(3H,m), 6.87(1H,t),6.72(1H,dd),6.67(1H,d), 5.70(1H,m),4.59(2H,m),1.26(6H,d) | 3600–2300,1640, 1610,1540,1450, 1255,1200,1090, 960,820 | 391(M⁺) 219,173 | white powder |
| 2(35) | 4-isobutylphenyl-propenyl | 0.62 (methylene chloride: methanol = 17:3) | 7.74(1H,d),7.43(3H,m),7.22(2H,d), 6.85(1H,t),6.70(1H,dd),6.66(1H,d), 5.68(1H,m),5.59(2H,m),2.48(2H,d), 1.86(1H,m),0.90(6H,d) | 3600–2300,1655, 1610,1540,1455, 1260,1100,965, 835,770,710 | 405(M⁺) 219,187 | white powder |
| 2(36) | 4-methylphenoxy-(pentyl)propenyl | 0.10 (chloroform: methanol = 4:1) | (CDCl₃) 7.80(1H,d),7.66(1H,s),7.42(2H,d),7.08 (1H,d),6.65–7.10(4H,m),6.48(1H,d),5.55– 6.00(3H,m),4.75(1H,d),4.40–4.65(3H,m) 2.08(2H,m),1.10–1.60(6H,m),0.88(3H,t) | 2930,2860,1680, 1600,1540,1510, 1460,1265,1180, 1100,970,830, 780 | 585, 475(M⁺) 329,121 | pale brown powder |

TABLE XII-continued

| Example No. | Substituent R in the general formula (Io) | Rf value in TLC (developing solvent) | NMR (δppm) | IR (νcm⁻¹) | Mass | Appearance |
|---|---|---|---|---|---|---|
| 2(37) | 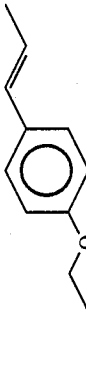 | 0.10 (chloroform: methanol = 4:1) | (CDCl₃) 7.80(1H,d),7.66(1H,s),7.42(2H,d),7.08 (1H,d),6.65-7.10(4H,m),6.48(1H,d),5.55-6.00(3H,m),4.75(1H,dd),4.40-4.65(3H,m), 2.08(2H,m),1.60(6H,m),0.88(3H,t) | 2930,2860,1680, 1600,1540,1510, 1460,1265,1180, 1100,970,830,780 | 585, 475(M⁺) 329,147 | white powder |
| 2(38) | 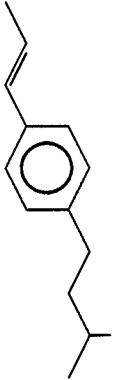 | 0.57 (chloroform: methanol = 4:1) | 7.74(1H,d),7.59(1H,d),7.47(2H,d), 7.19(1H,d),6.90(1H,t),6.73(1H,dd), 6.68(1H,d),5.71(1H,dd),4.66(1H,dd), 4.52(1H,dd),2.63(2H,m),2.40(1H,m), 1.52(2H,m),0.94(6H,d) | 3600-2300,1660, 1610,1540,1460, 1265,1200,1100, 965 | 419(M⁺) 219,201 | white powder |
| 2(39) | 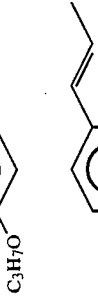 | 0.42 (methylene chloride: methanol = 17:3) | 7.30(1H,m),7.03(1H,m),6.84(1H,t), 6.72(1H,d),6.03(1H,d),5.70(1H,m), 4.60(1H,m),2.23(2H,m),1.36(22H,m), 0.88(3H,t) | 3600-2200,2900,2835, 1675,1660,1610,1530, 1460,1440,1260,1205, 1100,1040,970,910, 860,770,710 | 455(M⁺) 237,219 | white powder |
| 2(40) | 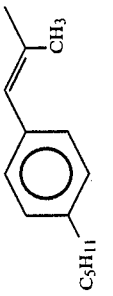 | 0.10 (chloroform: methanol = 4:1) | (CDCl₃ + DMSO—d₆) 7.52(2H,d),6.91(2H,d),6.91(1H,t). 6.70(1H,d),6.68(1H,d),5.70(1H,dd), 4.78(1H,dd),4.40(1H,dd),3.96(2H,t), 1.83(2H,m) | 2970,2680,1660, 1600,1540,1510, 1455,1260,1170, 1100,970,825, 770,710,560,515 | 407(M⁺) 219,189 147,119 91 | white powder |
| 2(41) | 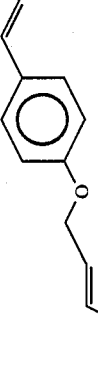 | 0.10 (chloroform: methanol = 4:1) | (CDCl₃ + DMSO—d₆) 8.68(1H,s),7.86(1H,d),7.72(1H,d),7.52 (2H,d),6.91(1H,t),6.90(2H,d),6.71(1H, d),6.67(1H,d),5.70(1H,dd),4.78(1H,dd), 4.40(1H,dd),4.00(2H,t) | 2970,2870,1660, 1600,1540,1510, 1460,1260,1190, 1175,1100,970, 830,770,715,565 | 421(M⁺) 219,203 147,119 91,69 | white powder |
| 2(42) | 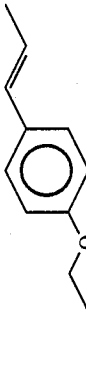 | 0.10 (chloroform: methanol = 4:1) | (CDCl₃ + DMSO—d₆) 8.62(1H,s),7.81(1H,d),7.72(1H,d),7.50 (2H,d),6.90(1H,t),6.88(2H,d),6.70(1H, d),6.65(1H,d),5.68(1H,dd),4.76(1H,dd), 4.40(1H,dd),3.98(2H,t) | 2920,2850,1660, 1600,1540,1510, 1460,1260,1170, 1100,970,910,825, 770,715,565,520 | 477(M⁺) 259,219 189,147 119 | pale yellow powder |
| 2(43) | 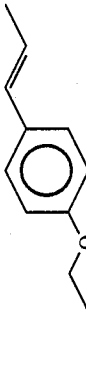 | 0.30 (methylene chloride: methanol = 5:1) | 7.52(1H,s),7.30(2H,d),7.20(2H,d) 7.15(1H,dd),6.89(1H,t),6.76(1H,dd), 5.78(1H,dd),4.80(1H,dd),4.52(1H,dd) | 3250,3200-2300, 1640,1600,1550, 1530,1490,1470, 1110,780 | 433(M⁺) 286,281 215 | white powder |

TABLE XII-continued

| Example No. | Substituent R in the general formula (Io) | Rf value in TLC (developing solvent) | NMR (δppm) | IR (νcm⁻¹) | Mass | Appearance |
|---|---|---|---|---|---|---|
| 2(44) | C₅H₁₁–CH=CH–C(=O)–NH–C₆H₄–CH₃ | 0.35 (chloroform: methanol = 4:1) | 7.88(2H,d),7.70(2H,d),7.51(1H,dd), 6.96(2H,m),6.76(1H,dd),6.04(1H,d), 5.76(1H,t),4.61(2H,m),2.25(2H,m), 1.49(2H,m),1.34(4H,m),0.89(3H,t) | 3600–2300,1650, 1610,1520,1445, 1260,1100,980, 850,780 | 462(M⁺) 419,244 | pale brown crystal |
| 2(45) | (phenyl)-(CH₂)₃-O-C₆H₄-CH₃ | 0.18 (chloroform: methanol = 4:1) | 7.87(1H,dd),7.82(2H,d),7.30–7.16 (5H,m),6.92(2H,d),6.84(1H,t), 6.69(1H,dd),5.57(1H,dd),4.62(1H,dd), 4.45(1H,dd) | 3600–2300,1650, 1610,1535,1510, 1460,1260 | 471(M⁺) 383,253 121 | white powder |
| 2(46) | CH₃-C₆H₄-O-CH₂-CH=CH-(CH₂)₃-CH₃ | 0.20 (methylene chloride: methanol = 5:1) | 7.89(1H,dd),7.83(2H,d),6.96(2H, brd),6.86(1H,t),6.70(1H,dd), 5.96–5.54(3H,m),4.65(1H,dd), 4.52(2H,d),4.46(1H,dd) | 3700–2200,2940, 1640,1600,1540, 1510,1460,1340, 1260,1180,1100, 1000,980,850,780 | 449(M⁺) 339,231 219,121 | white powder |

EXAMPLE 2(101)-2(107)

By the same procedures as reference example 1, 2 and example 2, using a corresponding carboxylic acid and 3-aminopyrocatechol which have corresponding substituents $R^2$ and $R^3$, following compounds having the following physical data, shown in table [XIII] were given.

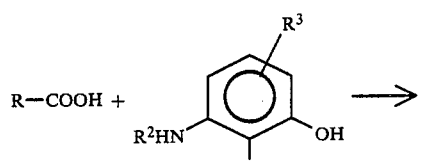

R—COOH +

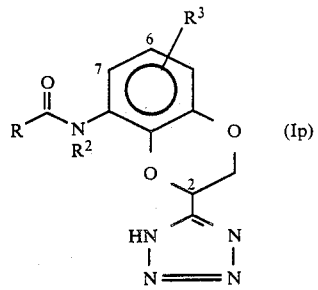

(Ip)

TABLE XIII

| Example No. | Substituent R,$R^2$,$R^3$ in the general formula (Ip) | Rf value in TLC (developing solvent) | NMR (δppm) | IR (νcm$^{-1}$) | Mass | Appearance |
|---|---|---|---|---|---|---|
| 2(101) | C$_5$H$_{11}$-[styryl] $R^2$ = CH$_3$, $R^3$ = H | 0.38 (methylene chloride: methanol = 3:1) | (CDCl$_3$) 7.92(1H,d), 7.52(2H,d), 7.22(2H,d), 7.00(1H,d), 6.96-6.74(3H,m), 5.77 (1H,m), 5.04(1H,d), 4.50(1H,dd), 3.59(3H,s), 0.88(3H,t) | (liquid film) 3500-2300, 1650, 1590, 1480, 1275, 1100 | 433(M$^+$) 233, 201 | pale brown solid |
| 2(102) | C$_5$H$_{11}$-[styryl] $R^2$ = H, $R^3$ = 6-Cl | 0.29 (chloroform: methanol = 3:1) | 8.03(1H,d), 7.71(1H,d), 7.48(2H,d), 7.18(2H,d), 6.81(1H,d), 6.71(1H,d), 4.79(1H,dd), 4.74(1H,dd), 4.35 (1H,dd) | (liquid film) 3600-3100, 1690, 1610, 1540, 1460, 1440, 1220 | 455, 453 255, 253 201 | pale brown oil |
| 2(103) | C$_5$H$_{11}$-[styryl] $R^2$ = H, $R^3$ = 6-Me | 0.30 (chloroform: methanol = 3:1) | 7.83(2H, 7.68(1H,d), 7.48(2H,d), 7.17(2H,d), 6.86(1H,d), 6.51(1H,d), 5.51(1H,dd), 4.70(1H,dd), 4.28 (1H,dd) | 3600-2500, 1680, 1620, 1610, 1540, 1460 | 201, 189, 175 | white solid |
| 2(104) | C$_5$H$_{11}$-[aryl] $R^2$ = H, $R^3$ = 6-Cl | 0.25 (chloroform: methanol = 3:1) | 7.81(2H,d), 7.65(1H,d), 7.38(1H,d), 6.77(1H,d), 5.75(1H,dd), 4.74-4.50 (2H,m), 0.88(3H,t) | 3300, 3200-2300, 1640, 1620, 1545, 1470, 1430, 1100, 860, 740 | 427(M$^+$) 243, 175 | brown crystal |
| 2(105) | C$_8$H$_{17}$O-[aryl] $R^2$ = Me, $R^3$ = H | 0.44 (methylene chloride: methanol = 17:3) | (CD$_3$OD) 7.20(3H,m), 6.74(4H,m), 5.22(1H,m), 4.40(2H,m), 3.92(2H,m), 3.36(3H,s), 1.73(2H,m), 1.31(10H,m), 0.90(3H,t) | 3600-2300, 1605, 1590, 1470, 1420, 1380, 1300, 1260, 1180, 1090, 1060, 1040, 1015, 895, 840, 760 | 465(M$^+$) 301, 233 | white powder |
| 2(106) | C$_5$H$_{11}$-CH=CH-CH$_2$-O-[aryl] $R^2$ = Me, $R^3$ = H | 0.41 (methylene chloride methanol = 17:3) | CD$_3$OD) 7.20(3H,m), 6.73(4H,m), 5.70(2H,m), 5.20(1H,m), 4.41(3H,m), 3.36(3H,s), 2.65(2H,m), 1.30(6H,m), 0.88(3H,t) | 3600-2300, 1610, 1595, 1470, 1420, 1380, 1300, 1250, 1220, 1175, 1090, 1040, 990, 960, 895, 840, 760 | 463(M$^+$) 343, 233 231 | white powder |
| 2(107) | C$_8$H$_{17}$O-[aryl] $R^2$ = H, $R^3$ = 7-COOCH$_3$ | 0.32 (chloroform: methanol = 4:1) | 7.99(2H,d), 7.63(1H,d), 7.00(2H,d), 6.88(1H,d), 5.97(1H,m), 4.60(2H,m), 4.05(2H,t), 3.88(3H,s), 1.83(2H,m), 1.32(10H,m), 0.90(3H,t) | 3600-2300, 1690, 1655, 1610, 1500, 1470, 1280, 1260, 1080, 910, 840, 780, 760 | 509(M$^+$) 449, 329 233 | white powder |

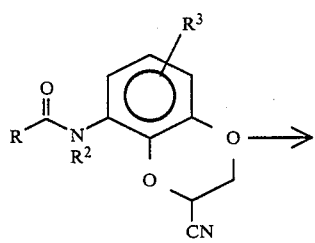

EXAMPLE 2(201)-2(204)

By the same procedure as reference example 1, 2 and example 2, using with a corresponding carboxylic acid and 3-aminopyrocatechol which have corresponding substituent $R^3$, following compounds having following physical data were given.

2(201)

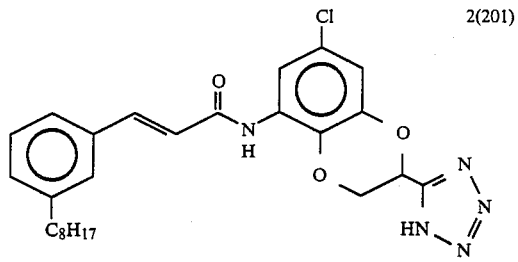

TLC : Rf 0.21 (Chloroform: methanol=3:1);

NMR : δ8.03(1H, d), 7.70(1H, d), 7.48(2H, d), 7.20 (2H, d), 6.71(1H, d), 6.65(1H, d), 5.57(1H, s), 4.70-4.40(2H, m), 2.62(2H, t);

IR : $\nu$3700-3000; 1680, 1625, 1610, 1535 1470, 1440 cm$^{-1}$;

Mass: m/e 201, 179, 162;

Appearance: white powder.

2(202)

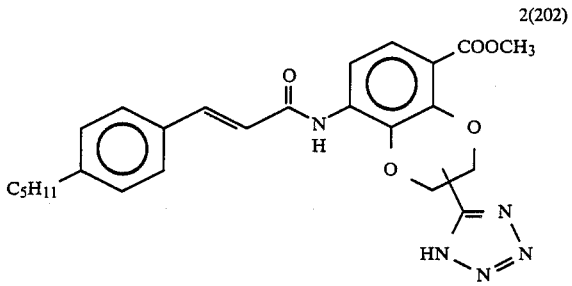

(The substituting position of tetrazolyl was not known.)

TLC : Rf 0.22 (methylene chloride: methanol=5:1);

NMR : δ8. 21(1H, d), 7.74(1H, d), 7.57(1H, d), 7.49(2H, d), 7.20(2H, d), 6.62(1H, d), 5.74(1H, dd), 4.89(1H, dd), 4.54(1H, dd);

IR : $\nu$3370, 3200-2300, 1695, 1630, 1610, 1520, 1430, 1270, 1140 cm$^{-1}$;

Mass: m/e 477(M+), 291, 201;

Appearance: white crystal.

2(203)-2(204)

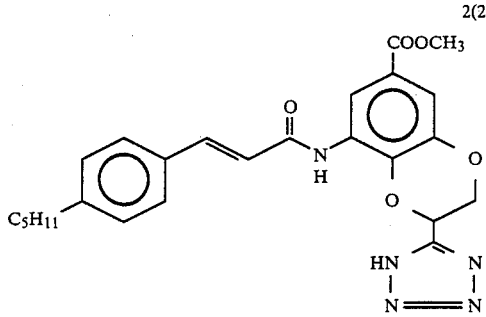

and

-continued

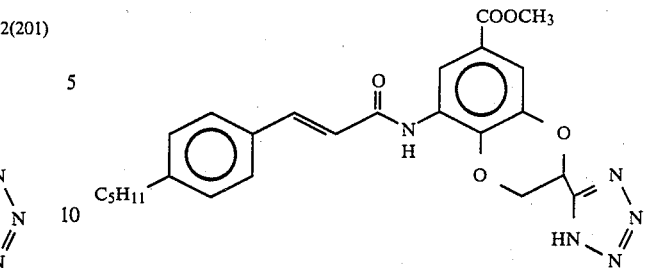

less polar compound:

TLC : Rf 0.18 (methylene chloride: methanol=5:1);

NMR (CDCl$_3$): δ9.88(1H, s), 7.81(1H, d), 7.45(3H, s), 7.18(2H, s), 6.69(1H, s), 6.64(1H, d), 6.04(1H, s), 5.60(1H, s), 4.50(1H, s), 3.84(3H, s), 0.88(3H, t);

IR : $\nu$3600-2300, 1695, 1630, 1610, 1515, 1470, 1280 cm$^{-1}$;

Mass: m/e 477(M+), 446, 291, 201;

Appearance: white crystal.

more polar compound:

TLC : Rf 0.12 (methylene chloride: methanol=5:1);

NMR (CDCl$_3$): δ9.44(1H, s), 7.46(1H, s), 7.25(1H, s), 7.13(2H, s), 6.88(2H, s), 6.60-6.30(2H, s), 5.20(1H, s), 4.20-3.60(2H, s), 3.72(3H, s), 0.83(3H, t);

IR : $\nu$3600-3000, 1695, 1630-1610, 1520 1480, 1280 cm$^{-1}$;

Mass: m/e 477(M+), 446, 291, 201;

Appearance: white crystal.

EXAMPLE 2(301)

By the same procedure as example 2, using with 8-(p-pentylcinnamoyl)amino-1,4-benzodioxane-2-acetonitrile (synthesized in reference example 5), following compound having the following physical data was given.

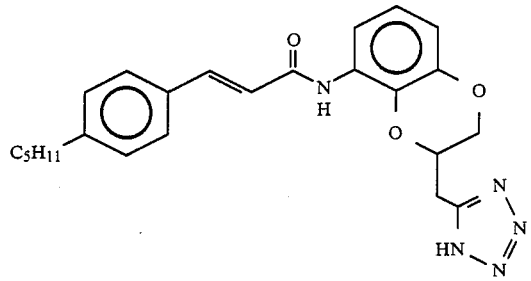

TLC : Rf 0.36 (methylene chloride: methanol=5:1);

NMR : δ7.88(1H, d), 7.70(1H, d), 7.47(2H, d), 7.20(2H, d), 6.84(1H, t), 6.63(1H, dd), 6.57(1H, d), 3.36(2H, d);

IR : $\nu$3300, 3200-2300, 1660, 1605, 1530, 1460 cm$^-$

Mass: m/e 433(M+), 233, 201;

Appearance: dark brown powder.

EXAMPLE 2(302)-2(303)

By the same procedure as example 2, using with a corresponding nitrile, following compounds having the following physical data were given.

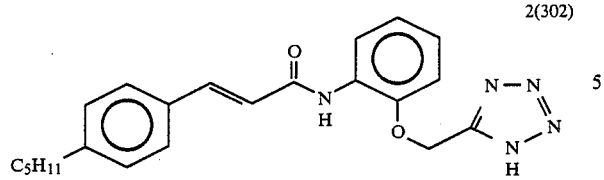

2(302)

TLC : 0.3 (methylene chloride: methanol=5:1);
IR : ν1655, 1615, 1600, 1540, 1490 cm$^{-1}$;
Mass: m/e 391(M+), 349, 309, 217, 201, 191;
Appearance: pale yellow powder.

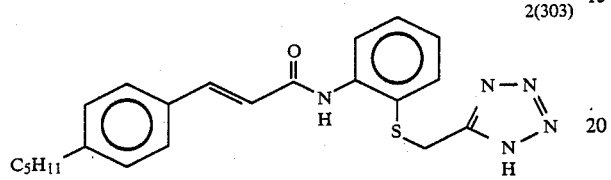

2(303)

TLC : 0.22 (chloroform: methahol=9:1);
IR : ν3300-2300, 2920, 1655, 1620, 1540, 1470, 1350, 1045, 980 cm$^{-1}$;
Mass: m/e 407(M+), 324, 292, 201;
Appearance: pale yellow crystal.

EXAMPLE 3

Synthesis of 8-(p-pentylcinnamoyl)amino-4-oxo-4H-1-benzopyran-2-carboxylic acid ethyl ester

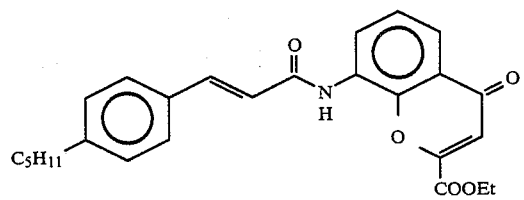

Oxalyl chloride (3.4 ml) was added to p-pentyl cinnamic acid (327 mg), and the mixture was stirred for 30 min at room temperature. Excess oxalyl chloride was removed from the mixture under reduced pressure. The residue was dissolved to methylene chloride (5 ml). In an atmosphere of argon, a solution of 8-amino-4-oxo-4H-1-benzopyran-2-carboxylic acid ethyl ester (420 mg) in a mixture of methylene chloride (5 ml) and triethylamine (0.6 ml) was added slowly. The reaction solution was stirred for 1 hr at room temperature, and then poured into 0.1 N hydrochloric acid. The mixture was extracted wita ethyl acetate. The extract was washed with water, a saturated aqueous solution of sodium bicarbonate and a saturated aqueous solution of sodium chloride, successively, dried, and concentrated under reduced pressure. The residue was purified by column chromatography on silica gel (ethyl acetate: hexane=1:3) to give the title compound (140 mg) having the following physical data:

TLC : Rf 0.60 (ethyl acetate: hexane=1:1);
NMR (CDCl$_3$): δ8.76(1H, dd), 8.23(1H, s), 7.72(1H, dd), 7.65(1H, d), 7.38(2H, d), 7.27(1H, t), 7.07(2H, d), 7.00(1H, s), 6.52(1H, d);
IR : ν3270, 2930, 1730, 1660, 1630, 1530, 1430, 1290, 1260, 1180, 770 cm$^{-1}$;

Mass: m/e 433(M+), 404, 388, 376, 360, 318, 233, 201, 131;
Appearance: white powder.

EXAMPLE 4

Synthesis of 8-(p-pentylcinnamoyl)amino-4-oxo-4H-1-benzopyran-2-carboxylic acid

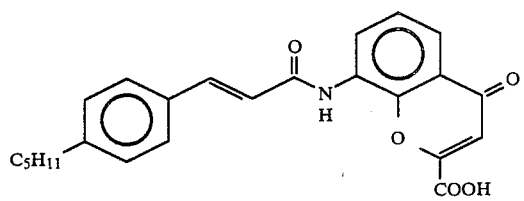

8-(p-pentylcinnamoyl)amino-4-oxo-4H-1-benzopyran-2-carboxylic acid ethyl ester (132 mg; synthesized in example 3) was dissolved into ethanol (10 ml). To the solution, an aqueous solution (1 ml) of sodium bicarbonate (126 mg) was added. The mixture was refluxed for 15 min. To the reaction solution mixture cooled to room temperature, water (20 ml) and 1N hydrochloric acid (2 ml) were added. The mixture was extracted with ethyl acetate. The extract was washed with water and a saturated aqueous solution of sodium chloride, dried, and concentrated under reduced pressure. The residue was washed with a mixture of ethyl acetate and hexane (1:1), and dried to give the title compound (62 mg) having the following physical data:

TLC : Rf 0.25 (ethyl acetate: methanol=5:1);
NMR : δ8.66(1H, dd), 7.86(1H, dd), 7.73(1H, d), 7.53(2H, d), 7.43(1H, t), 7.22(2H, d), 7.15(1H, s), 7.08(1H, d);
IR : ν3400, 2930, 1635, 1520, 1430, 1360 cm$^{-1}$;
Mass: m/e 405(M+), 361, 201, 181, 169, 131, 69;
Appearance: yellow powder.

EXAMPLE 4(1)–4(3)

By the same procedure as example 3 and 4, using with a corresponding carboxylic acid and 8-amino-4-oxo-4H-1-benzopyran-1-carboxylic acid ethyl ester which have corresponding substituent R$^3$, following compounds having the following physical data, shown in table [XIV] were given.

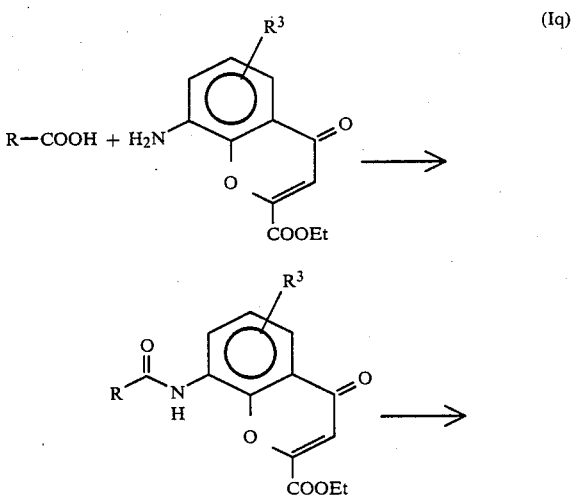

(Iq)

-continued

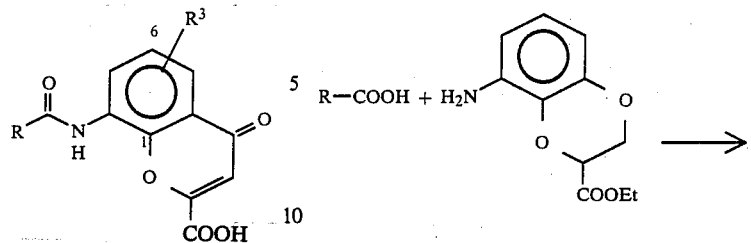
(Ir)

TABLE XIV

| Example No. | Substituent R,R³ in the general formula (Iq) | Rf value in TLC (developing solvent) | NMR (δppm) | IR (νcm⁻¹) | Mass | Appearance |
|---|---|---|---|---|---|---|
| 4(1) | (structure with alkyne-O-phenyl-vinyl); R³ = H | 0.2 (methylene chloride: methanol = 5:1) | 8.90(1H,dd), 7.88(1H,dd), 7.74(1H, d), 7.5–7.6(2H,m), 7.46(1H,t), 7.18 (1H,s), 6.95–7.05(2H,m), 6.88(1H, d), 4.70(2H,t) | 1650, 1630, 1600, 1580, 1540, 1510 | 459(M⁺) 415, 351 255,164 147 | pale yellow powder |
| 4(2) | C₅H₁₁-phenyl-vinyl; R³ = 6-Me | 0.20 (ethyl acetate: methanol = 5:1) | 8.75(1H,d), 7.76(1H,d), 7.68(1H,m), 7.54(2H,d), 7.22(2H,d), 7.16(1H,s), 6.99(1H,d), 2.64(2H,t), 2.50(3H,s), 1.64(2H,m), 1.20–1.50(4H,m), 0.90 (3H,t) | 3450, 2930, 2850, 1735, 1625, 1600 1535, 1445, 1270, 1210, 1180, 980, 820 | 419(M⁺) 219, 201 131 | pale yellow powder |
| 4(3) | C₅H₁₁-phenyl-; R³ = H | 0.17 (chloroform: methanol = 4:1) | 8.46(1H,dd), 7.92(1H,dd), 7.92(2H, d), 7.46(1H,t), 7.32(2H,d), 7.08 (1H,s), 2.70(2H,t), 0.90(3H,t) | 3270, 1700, 1650, 1630, 1620, 1580, 1525, 1440, 1360 | 175, 173 | yellow powder |

EXAMPLE 4(101)–4(104)

By the same procedure as example 3 and 4, using with corresponding carboylic acid and 8-amino-1,4-benzodioxane-2-carboxylic acid ethyl easter, following compounds having the following physical data, shown in table [XV] were given.

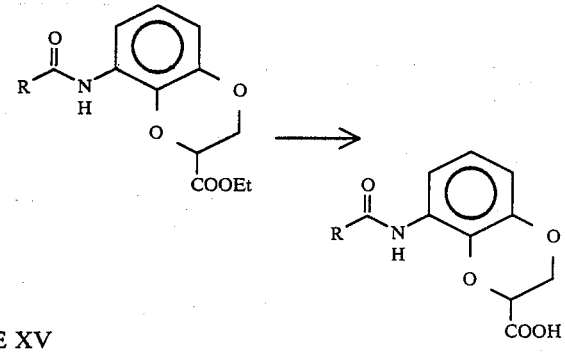

TABLE XV

| Example No. | Substituent R in the general formula (Ir) | Rf value in TLC (developing solvent) | NMR (δppm) | IR (νcm⁻¹) | Mass | Appearance |
|---|---|---|---|---|---|---|
| 4(101) | C₅H₁₁-phenyl-vinyl | 0.10 (ethyl acetate: methanol = 10:1) | (CD₃OD) 7.80(1H,d), 7.62(1H,d), 7.50 (2H,d), 7.20(2H,d), 6.92(1H,d), 6.78(1H, t), 6.62(1H,dd), 4.70(1H,dd), 4.54(1H, dd), 4.18(1H,dd), 2.62(2H,t), 1.62(2H,m), 1.20–1.45(4H,m), 0.90(3H,t) | 3300, 2930, 2850, 1610, 1530, 1440, 1260, 1180, 1100, 975, 825, 770 | 395(M⁺) 351, 201 195, 161 127, 85 | white powder |
| 4(102) | C₈H₁₇O-phenyl- | 0.37 (chloroform: methanol = 4:1) | 7.92(2H,d), 7.69(1H,dd), 6.95(2H,dd), 6.84(1H,t), 6.66(1H,dd), 4.66(1H,m), 4.45(1H,dd), 4.27(1H,dd), 4.02(2H,t), 1.81(2H,m), 1.31(8H,m), 0.88(3H,t) | 3650–2400, 1605, 1440, 1250, 1170, 1080, 895, 840, 770 | 409(M⁺) 233 | pale yellow crystal |
| 4(103) | C₅H₁₁-vinyl-CH₂-O-phenyl- | 0.39 (chloroform: methanol = 4:1) | 7.91(2H,d), 7.71(1H,dd), 6.96(2H,d), 6.93(1H,t), 6.65(1H,dd), 5.78(2H,m), 4.68(1H,m), 4.53(2H,d), 4.41(1H,m), 4.31(1H,m), 2.09(2H,m), 1.32(6H,m), 0.88(3H,t) | 3650–2500, 1600, 1450, 1255, 1180, 1090, 1000, 840, 775 | 407, 231 | white powder |
| 4(104) | (alkyne-O-phenyl) | 0.50 (chloroform: methanol = 4:1) | 7.92(2H,d), 7.72(1H,dd), 7.02(2H,d), 6.84(1H,t), 6.65(1H,dd), 4.72(3H,t), 4.38(2H,m), 2.21(2H,m), 1.49(2H,m), 1.32(4H,m), 0.87(3H,m) | 3650–2500, 1605, 1440, 1255, 1170, 1080, 990, 890, 830, 760 | 405 219 | yellow brown powder |

EXAMPLE 4(201)–4(208)

By the same procedure as example 4, using with a corresponding carboxylic acid and a corresponding amine, following compounds having the following physical data, shown in table [XVI] were given.

TABLE XVI

| Example No. | Formula | Rf value in TLC (developing solvent) | NMR (δppm) | IR (νcm$^{-1}$) | Mass | Appearance |
|---|---|---|---|---|---|---|
| 4(201) | (structure: 4-hydroxy-8-[4-(phenylmethoxy)benzamido]quinoline-2-carboxylic acid) | 0.05 (chloroform:methanol = 4:1) | (CDCl$_3$ + DMSO-d$_6$) 10.75(1H, s), 8.62(1H, d), 7.90–8.10 (3H, m), 7.40–7.65(2H, m), 7.10–7.35 (5H, m), 7.00(2H, d), 4.07(2H, t), 2.70(2H, t), 1.85(4H, m) | 3250, 2930, 1630, 1600, 1490, 1250, 1175, 840, 755, 695 | 456(m$^+$), 412, 394, 262, 253, 121, 91 | white powder |
| 4(202) | (structure with thiophene) | 0.05 (chloroform:methanol = 4:1) | (CDCl$_3$ + DMSO-d$_6$) 10.72(1H, s), 8.60(1H, d), 7.90–8.10 (3H, m), 7.40–7.65(2H, m), 7.13(1H, dd), 7.00(2H, d), 6.91(1H, dd), 6.81(1H, d), 4.07(2H, m), 2.92(2H, m), 1.90(4H, m) | 3250, 2930, 1630, 1600, 1500, 1250, 1250, 1175, 840, 760, 695 | 462(m$^+$), 418, 400, 276, 259, 139, 121, 97 | yellow brown powder |
| 4(203) | (structure with tetrazole) | 0.05 (chloroform:methanol = 4:1) | 880(1H, dd), 7.98(2H, d), 7.92(1H, dd), 7.58(1H, s), 7.50(1H, d), 7.00(2H, d), 5.60–6.00(3H, m), 4.85–5.10(2H, m), 4.55(2H, d), 2.10(4H, m), 1.50(2H, m) | 3350, 3060, 2930, 1640, 1605, 1500–1530, 1360, 1255, 1175, 995, 965, 905, 840, 760 | | pale yellow powder |

TABLE XVI-continued

| Example No. | Formula | Rf value in TLC (developing solvent) | NMR (δppm) | IR (νcm⁻¹) | Mass | Appearance |
|---|---|---|---|---|---|---|
| 4(204) | (structure: 8-benzamido-4-hydroxyquinoline with tetrazole and benzyloxyphenyl) | 0.47 (methylene chloride: methanol = 5:1) | 8.03(1H, dd), 7.93(2H, d), 7.36–7.14 (5H, m), 7.04(1H, t), 6.96(2H, d), 6.83(1H, dd), 5.45(1H, dd), 4.60(1H, dt), 4.15(1H, dt) | 3400–2300, 1645, 1610, 1510, 1480, 1450, 1260, 1060 | 485(m⁺), 442, 439, 411, 377, 359 | white powder |
| 4(205) | (structure: 2-(pentylphenyl)-methyl-acrylamide with phenyl-S-CH₂CH₂COOH) | 0.33 (cyclohexane: ethyl acetate = 1:2) | (CDCl₃) 9.1(1H, s), 8.53(1H, d), 7.54 (1H, s), 7.38(1H, t), 7.34(2H, d), 7.22 (2H, d), 7.06(1H, t), 2.83(2H, t), 2.64(2H, t), 2.48(2H, t), 2.28(3H, d), 1.89(2H, m), 1.65(2H, m), 1.33(4H, m), 0.90(3H, t) | 3450, 3340, 2920, 2850, 1710, 1660, 1610, 1500, 1470, 1430, 1190 | 425(m⁺), 306, 215, 145 | white powder |
| 4(206) | (structure: 2-(pentylphenyl)methylacrylamide isomer with phenyl-S-CH₂CH₂COOH) | 0.30 (cyclohexane: ethyl acetate = 1:2) | (CDCl₃) 8.54(1H, s), 8.50(1H, d), 7.50(1H, d), 7.42(2H, d), 7.35(1H, t), 7.20(2H, d), 7.04(1H, t), 6.20(1H, d), 2.80(2H, t), 2.60(5H, m), 2.48(2H, t), 1.88(2H, m), 1.64(2H, m), 1.35(4H, m), 0.90(3H, t) | 3300, 2950, 2860, 1710, 1640, 1480 | 425(m⁺), 306, 215, 211 | white powder |
| 4(207) | (structure: 2-(pentylphenyl)acrylamide with phenyl-S-CH₂CH₂CH₂COOH) | 0.30 (ethyl acetate: ethanol = 1:1) | (CDCl₃) 8.64(1H, s), 8.52(1H, d), 7.75(1H, d), 7.40–7.60(3H, m), 7.36(1H, t), 7.10–7.30 (2H, m), 7.06(1H, dt), 6.56(1H, d), 2.82 (2H, t), 2.63(2H, t), 2.48(2H, t), 1.80–2.00(2H, m) | 1700, 1655, 1615, 1570, 1520 | 411(m⁺), 2.92, 2.11, 201 | white powder |

TABLE XVI-continued

| Example No. | Formula | Rf value in TLC (developing solvent) | NMR (δppm) | IR (νcm$^{-1}$) | Mass | Appearance |
|---|---|---|---|---|---|---|
| 4(208) | (structure: 4-(hex-4-enyloxy)-N-(4-hydroxy-2-carboxyquinolin-8-yl)benzamide) | 0.05 (chloroform: methanol = 4:1) | (CDCl$_3$ + DMSO-d$_6$): 10.70(1H, s), 8.50(1H, dd), 8.00(3H, m), 7.50(2H, m), 7.02(2H, d), 5.60–6.00(3H, m), 4.85–5.10(2H, m), 4.58(2H, d), 2.10(4H, m), 1.50(2H, m) | 3280, 2950, 1640, 1605, 1590, 1500, 1260, 1180, 1100, 760 | | pale yellow powder |

EXAMPLE 4(301)–4(320)

By the same procedure as example 4, using with a corresponding carboxylic acid and a corresponding amine, following compounds having the following physical data, shown in table [XVII] were given.

TABLE XVII

| Example No. | Formula | Rf value in TLC (developing solvent) | Mass | Appearance |
|---|---|---|---|---|
| 4(301) | $C_5H_{11}$-C6H4-CH=CH-C(=O)-NH-C6H4-S-CH2-COOH | 0.48 (ethyl acetate) | 383($M^+$), 365, 292, 201 | pale yellow crystal |
| 4(302) | $C_5H_{11}$-C6H4-CH=CH-C(=O)-NH-C6H4-S-CH2CH2-COOH | 0.4 (ethyl acetate: hexane = 1:1) | 397($M^+$), 292, 201, 197, 141 | white powder |
| 4(303) | octenyl-O-C6H4-C(=O)-NH-C6H4-O-CH2-COOH | 0.10 (methylene chloride) | 395($M^+$), 287, 258, 229, 167 | pale brown powder |
| 4(304) | iPr-C6H4-CH=CH-C(=O)-NH-C6H4-S-(CH2)3-COOH | 0.2 (cyclohexane: ethyl acetate = 1:2) | 383($M^+$), 264, 211, 173 | white powder |
| 4(305) | cyclohexyl-C6H4-CH=CH-C(=O)-NH-C6H4-S-(CH2)3-COOH | 0.3 (cyclohexane: ethyl acetate = 1:2) | 423($M^+$), 304, 213, 211, 187, 131 | white powder |
| 4(306) | cyclohexyl-C6H4-CH=CH-C(=O)-NH-C6H4-S-(CH2)3-COOH | 0.24 (cyclohexane: ethyl acetate = 1:2) | 431($M^+$), 312, 221, 211, 125, 91 | white powder |
| 4(307) | $C_6H_{11}$-C≡C-CH2-O-C6H4-CH=CH-C(=O)-NH-C6H4-S-(CH2)3-COOH | 0.26 (cyclohexane: ethyl acetate = 1:2) | 465($M^+$), 346, 255, 245, 211, 147 | pale yellow powder |
| 4(308) | $C_5H_{11}$-C6H4-CH=CH-C(=O)-NH-C6H3(Cl)-O-(CH2)3-COOH | 0.43 (ethyl acetate) | 429($M^+$), 231, 229, 201 | white crystal |
| 4(309) | iPentyl-O-C6H4-C(Ph)=CH-C(=O)-N(CH3)-C6H4-O-(CH2)3-COOH | 0.34 (ethyl acetate) | 515($M^+$), 412, 307 | white crystal |
| 4(310) | pentyl-O-C6H4-C(CH3)=C(CH3)-C(=O)-NH-C6H4-O-(CH2)3-COOH | 0.39 (ethyl acetate: hexane = 1:1) | 439($M^+$), 245 | white crystal |
| 4(311) | heptenyl-O-C6H3(Cl)-CH=CH-C(=O)-NH-C6H4-O-(CH2)3-COOH | 0.34 (ethyl acetate) | 459($M^+$), 461, 424, 349, 265 | white crystal |

TABLE XVII-continued

| Example No. | Formula | Rf value in TLC (developing solvent) | Mass | Appearance |
|---|---|---|---|---|
| 4(312) | (phenyl-S-CH₂CH₂CH₂-O-C₆H₄-C(=O)-NH-C₆H₄-O-CH₂CH₂CH₂-COOH) | 0.44 (ethyl acetate) | 465(M⁺), 391 | white crystal |
| 4(313) | ClC₅H₁₀-C₆H₄-C(=O)-NH-C₆H₄-O-CH₂CH₂CH₂-COOH | 0.34 (ethyl acetate) | 419(M⁺), 225 | pale brown crystal |
| 4(314) | C₅H₁₁-C₆H₄-CH₂-O-C₆H₄-C(CH₃)=CH-C(=O)-NH-C₆H₄-O-CH₂CH₂CH₂-COOH | 0.23 (ethyl acetate: hexane = 1:1) | 515(M⁺), 355, 321, 161 | white powder |
| 4(315) | C₅H₁₁-O-C₆H₃(OCH₃)-C(=O)-NH-C₆H₄-O-CH₂CH₂CH₂-COOH | 0.38 (ethyl acetate: hexane = 1:1) | 415(M⁺), 221 | white crystal |
| 4(316) | C₅H₁₁-C₆H₄-CH₂-O-C₆H₃(Cl)-C(CH₃)=CH-C(=O)-NH-C₆H₄-O-CH₂CH₂CH₂-COOH | 0.06 (ethyl acetate: hexane = 1:3) | 549(M⁺), 515, 463, 355, 195, 161 | white crystal |
| 4(317) | C₅H₁₁-C₆H₄-C₆H₄-C(CH₃)=CH-C(=O)-NH-C₆H₄-O-CH₂CH₂CH₂-COOH | 0.22 (ethyl acetate: hexane = 1:1) | 499(M⁺), 394, 305 | white crystal |
| 4(318) | C₅H₁₁-C₆H₄-C(CH₃)=CH-CH=CH-C(=O)-NH-C₆H₄-O-CH₂CH₂CH₂-COOH | 0.22 (ethyl acetate: hexane = 1:1) | 435(M⁺), 241 | pale yellow powder |
| 4(319) | (phenyl-CH₂CH₂CH₂CH₂-S-C₆H₄-C(CH₃)=CH-C(=O)-NH-C₆H₄-O-CH₂CH₂CH₂-COOH) | 0.18 (ethyl acetate: hexane = 1:1) | 503(M⁺), 417, 400, 399, 398, 309 | white powder |
| 4(320) | (C₅H₁₁-C₆H₄-CH₂-O-C₆H₄-C(CH₃)=CH-C(=O)-NH-C₆H₄-O-CH₂CH₂CH₂-COOH) | 0.21 (ethyl acetate: hexane = 1:1) | 515(M⁺), 429, 355, 321 | white crystal |

EXAMPLE 5

Synthesis of
8-[p-(4-phenylbutoxy)benzoylamino]-2-(5-tetrazolyl)-2,3-dihydrobenzoxazine

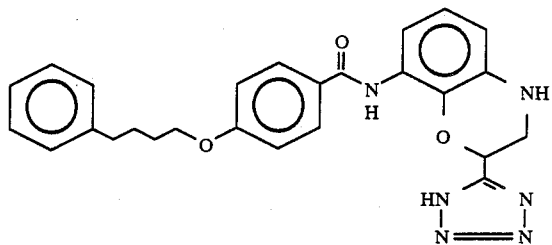

In an atmosphere of argon, a mixture of 8-[-(4-phenylbutoxy)benzoylamino]-N-trifluoroacetyl-2,3-dihydrobenzoxazin-2-nitrile (316 mg), sodium azide (196 mg), ammonium chloride (161 mg) and dimethylformamide (2.5 ml) was stirred for 1 hr at 100° C. After reaction, the reaction solution was poured into a mixture of ice and dil. hydrochloric acid, and the mixture was extracted with ethyl acetate. The extract was washed, dried over magnesium sulphate, and condensed under reduced pressure. The residue was dissolved into ethanol which was saturated with ammonia (50 ml). The solution was stirred for 20 hrs at room temperature and then concentrated under reduced pressure. The residue was purified by column chromatography on silica gel (chloroform: methanol=3:1) to give the title compound (207 mg) having the following physical data:

TLC : Rf 0.36 (chloroform: methanol=3:1);

IR : $\nu$3600–2300, 1630, 1600, 1500, 1465, 1250, 1170 cm$^{-1}$;

Mass: m/e 470(M+), 376, 358, 253;

Appearance: brown powder.

EXAMPLE 5(1)–5(10)

By the same procedure as example 5, using with a corresponding nitrile, following compounds having the following physical data, shown in table [XVIII] were given.

TABLE XVIII

| Example No. | Formula | Rf value in TLC (developing solvent) | NMR (δppm) | IR (νcm$^{-1}$) | Mass | Appearance |
|---|---|---|---|---|---|---|
| 5(1) | | 0.30 (methylene chloride: methanol = 5:1) | 8.09(1H, dd), 7.88(2H, d), 7.40–7.00 (8H, m), 6.95(2H, d), 5.54(2H, s), 4.03(2H, t), 2.71(2H, t), 1.95–1.75 (4H, m) | 3350, 3100–2300, 1610, 1600, 1560, 1530, 1510, 1450, 1260 | 443(m$^+$), 361, 343, 253 | white powder |
| 5(2) | | (CDCl$_3$) 0.30 (methylene chloride: methanol = 5:1) | 8.10(1H, s), 7.68(2H, d), 7.76–7.64(1H, d), 7.05(1H, t), 6.92(1H, t), 6.82(2H, d), 6.72(1H, d), 6.00–5.58(2H, m), 5.46(2H, d), 4.47(2H, d) | 3200, 3100–2300, 1600, 1590, 1560, 1525, 1500, 1250 | 421(m$^+$), 331, 311, 301, 231 | white powder |
| 5(3) | | 0.36 (methylene chloride: methanol = 3:1) | 7.88(2H, d), 7.22(6H, m), 6.93(2H, d), 6.79(1H, t), 6.47(1H, dd), 5.68(1H, t), 4.02(2H, t), 3.89(1H, dd), 3.73(1H, dd), 2.67(2H, m), 1.84(4H, m) | 3600–2300, 1630, 1600, 1500, 1465, 1250, 1170 | 470(m$^+$), 376, 358, 253 | brown powder |

TABLE XVIII-continued

| Example No. | Formula | Rf value in TLC (developing solvent) | NMR (δppm) | IR (νcm⁻¹) | Mass | Appearance |
|---|---|---|---|---|---|---|
| 5(4) | (naphthalene-amide-tetrazole structure with allyloxy phenyl) | 0.20 (chloroform: methanol = 4:1) | (CDCl₃ + CD₃OD + DMSO—d₆) 8.06(2H, d), 7.85(1H, d), 7.64(1H, d), 7.46(1H, m), 7.38(1H, d), 7.27(1H, dd), 7.03(2H, d), 5.80(1H, m), 5.53(2H, s), 5.00(2H, m), 4.06(2H, t), 2.08(2H, m), 1.83(2H, m), 1.45(6H, m) | 3220, 2930, 2850, 1620, 1600, 1495, 1250, 1225, 1170, 1055, 840, 825 | 471(m⁺), 389, 231, 121 | grey powder |
| 5(5) | (naphthalene-amide-tetrazole structure with benzyloxy phenyl) | 0.20 (chloroform: methanol = 4:1) | (DMSO—d₆) 8.06(2H, d), 7.95(1H, d), 7.80(1H, d), 7.61(1H, d), 7.20–7.55(8H, m), 7.10(2H, d), 5.58(2H, s), 4.31(2H, t), 3.30(1H, s), 3.10(2H, t) | 3270, 1620, 1600, 1490, 1260, 1175, 835 | 465(m⁺), 422, 383, 262, 225, 121, 105 | grey powder |
| 5(6) | (naphthalene-amide-tetrazole structure with phenoxy phenyl) | 0.20 (chloroform: methanol = 4:1) | (DMSO—d₆) 8.04(2H, d), 7.94(1H, d), 7.78(1H, d), 7.60(1H, d), 7.49(1H, d), 7.41(1H, t), 7.35–7.11(6H, m), 7.06(2H, d), 5.58(2H, s), 4.09(2H, t) | 3500–2300, 1620, 1600, 1570, 1520, 1490, 1250 | 493(m⁺), 411, 253 | grey powder |

TABLE XVIII-continued
| Example No. | Formula | Rf value in TLC (developing solvent) | NMR (δppm) | IR (νcm⁻¹) | Mass | Appearance |
|---|---|---|---|---|---|---|
| 5(7) | 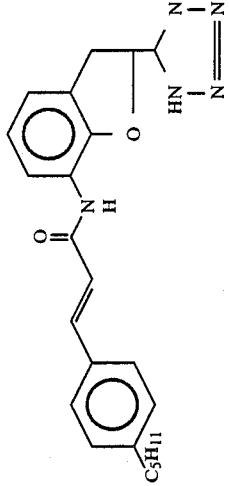 | 0.34 (chloroform: methanol = 4:1) | 7.77(1H, d), 7.56–6.89(7H, m), 6.47(2H, d), 6.20(1H, dd), 3.87(1H, dd), 2.62(2H, t), 0.90(3H, t) | 3300, 2950, 1670, 1630, 1540, 1450, 1190 | 403(m⁺), 346, 328, 201 | pale brown powder |
| 5(8) | 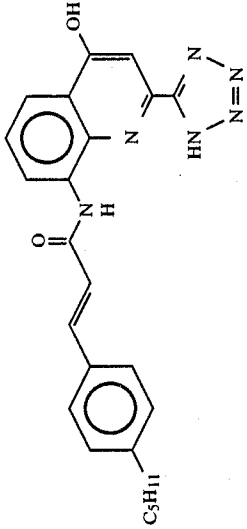 | 0.10 (chloroform: methanol = 4:1) | | | 428(M⁺), 410, 400, 296, 201 | yellow powder |
| 5(9) | 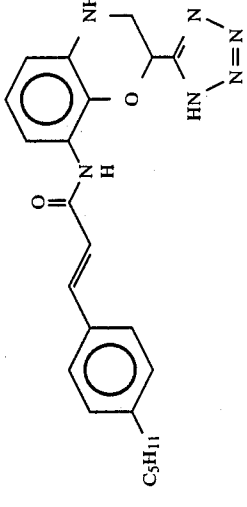 | 0.24 (chloroform: methanol = 3:1) | | | 418(M⁺), 201 | white powder |
| 5(10) | 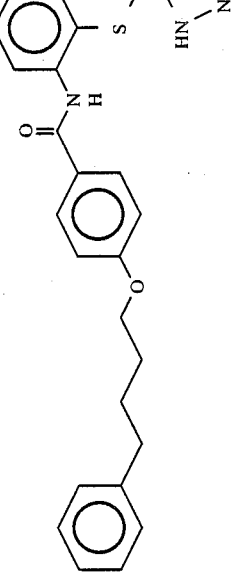 | 0.7 (methylene chloride: methanol = 3:1) | | | 296, 253 | yellow powder |

EXAMPLE 6

Synthesis of 4-[2-(p-pentyl-2-methylcinnamoyl)-aminophenoxy]-butanoic acid and ethyl ester thereof.

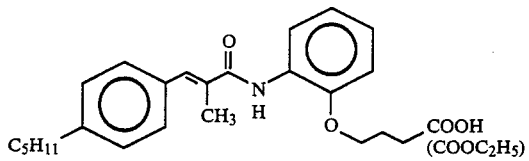

A mixture of 2-(p-pentyl-2-methylcinnamoyl)-aminophenol (267 mg), 4-bromobutanoic acid ethyl ester (322 mg), potassium carbonate (135 mg) and acetone (2 ml) was refluxed overnight. After cooling, the reaction solution was diluted with ethyl acetate, precipitation was removed by filtration from the solution. The solution was concentrated under reduced pressure to give the title compound (ester) having the following physical data:

TLC : Rf 0.66 (toluene: ethyl acetate=10:1);
Mass: m/e 437(M+).

Ester obtained was dissolved into methanol (3.2 ml). To the solution, a 2N aqueous solution of sodium hydroxide (1.64 ml), and the solution was stirred for 1.5 hrs at 40° C. After reaction, the solution was acidified with dil. hydrochloric acid. The mixture was extracted with ethyl acetate. The extract was washed with water, dried and concentrated under reduced pressure to give the title compound (acid; 285 mg) having the following physical data:

TLC : Rf 0.60 (methylene chloride: methanol=5:1);
IR : $\nu$3470, 3200–2300, 1710, 1670, 1620, 1600, 1530, 1450, 750 cm$^{-1}$;
NMR (CDCl$_3$): $\delta$8.44(1H, dd), 8.28(1H, s), 7.45(1H, s), 7.30(2H, d), 7.18(1H, dd), 4.11(2H, t);
Mass: m/e 409(M+), 215, 187;
Appearance: white powder.

EXAMPLE 6(1)–6(2)

By the same procedure as Example 6, using a corresponding pheno , following compounds were given.

6(1)

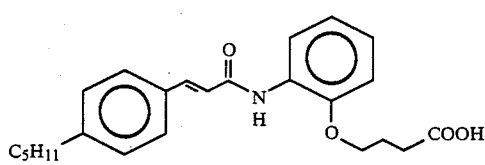

TLC: Rf 0.48 (ethyl acetate);
IR: $\nu$3320, 3200–2300, 1700, 1660, 1630, 1610, 1540 cm$^{-1}$;
NMR (CDCl$_3$): $\delta$8.40(1H, d), 8.22(1H, s), 7.60(1H, d), 7.34(2H, s), 7.04(2H, d), 6.85(1H, dd), 6.76(1H, d), 6.69(1H, dd);
Mass: m/e 395(M+), 201, 195; Appearance: white powder.

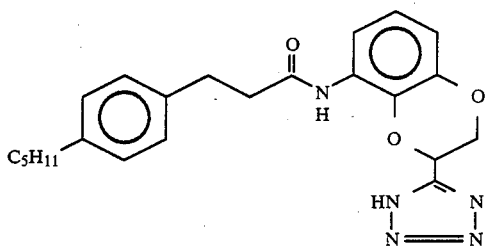

TLC:0.4 (methylene chloride: methanol =5:1);
IR: $\nu$1655, 1600, 1520, 1445 cm$^{-1}$;
Mass: m/e 445M+), 363, 345, 255, 191, 147;
Appearance: pale yellow powder.

EXAMPLE 7

Synthesis of 8-[3-(p-pentylphenyl)propionyl]amino-2-(5-tetrazolyl)-1,4-benzodioxane

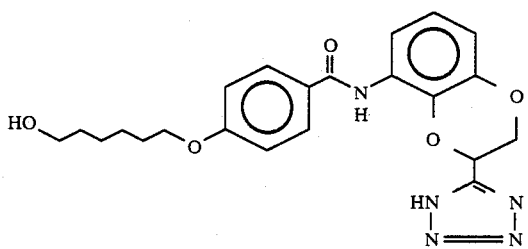

8-(p-pentylcinnamoyl)amino-2-(5-tetrazolyl)-1,4-benzodioxane (216 mg; synthesized in example 2(1)) and palladium-carbon (50 mg; content 5%) were suspended in a mixed solvent (6 ml) of methanol, ethanol and ethyl acetate (1:1:1). In an atmosphere of hydrogen, the suspension was stirred for 90 min at room temperature. After stirring, the suspension was filtered through celite. The filtrate was condenced under reduced pressure. Thre residue was purified by column chromatography on silica gel (methylene chloride: methanol=19:1) to give the title compound (202 mg) having the following physical data:

TLC: Rf 0.54 (methylene chloride: methanol=4:1);
NMR (CDCl$_3$): $\delta$7.28(1H, s), 7.11(4H, 2d), 6.76(2H, m), 6.60(1H, dd), 5.68(1H, t), 4.93(1H, dd), 3.04(2H, t), 2.77(2H, m), 2.56(2H, t), 1.58(2H, m), 1.30(4H, m), 0.88(3H, t);
IR: $\nu$3600–2300, 1650, 1615, 1530, 1460, 1260, 1100, 780 cm$^{-1}$;
Mass: m/e 421(M+), 219;
Appearance: white crystal.

EXAMPLE 8

Synthesis of 8-[p-(6-hydroxyhexyloxy)benzoyl]amino-2-(5-tetrazolyl)-1,4-benzodioxane A 1N aqueous solution of sodium hydroxide (0.5 ml) was added to a solution of 8-[p-(6-acetyloxyhexyloxy)-benzoyl]-amino-2-(5-tetrazolyl)-1,4-benzodioxane (100 mg; synthesized in example 1 (96)) in methanol (0.5 ml) at room temperature. The reaction solution was stirred for 10 min at the same temperature, and then concentrated under reduced pressure. To the residue, dil. hydrochloric acid was added and the mixture was extracted with ethyl acetate. The extract was dried and concentrated under reduced pressure. The residue was purified by column chromatography on silica gel (methylene chloride: methanol=100:1) to give the title compound (95 mg) having the following physical data:

TLC: Rf 0.23 (methylene chloride: methanol=5:1);

NMR: δ7.89(2H, d), 7.46(1H, dd), 6.95(2H, d), 6.92(1H, t), 6.76(1H, dd), 4.02(2H, t), 3.60(2H, t);

IR: ν3400, 3200–2300, 1630, 1600, 1520, 1500, 1440, 1250 cm$^{-1}$;

Mass: m/e 439(M+), 221, 149, 121;

Appearance: white amorphous.

EXAMPLE 9

Synthesis of 8-[p-[5-(N,N-dimethylamino)pentyloxy]cinnamoyl]-amino-1,4-benzodioxane sodium salt

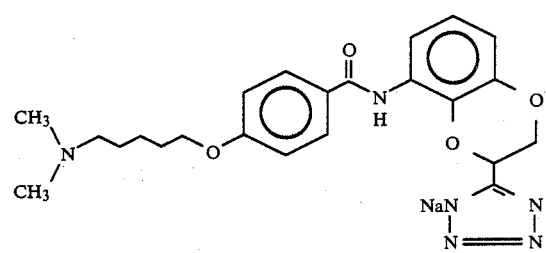

A 40% aqueous solution of dimethylamine (1 ml) was dropped to a solution of 8-[p-(5-bromopentyloxy)cinnamoyl]-amino-1,4-benzodioxane (176 mg; synthesized in example 1 (113)). The solution was stirred for 1 hr at room temperature. Volatile matter was removed with vacuum pump for 1 hr at room temperature, and for 3 hrs at 90° C. The residue was dissolved into methanol (1 ml), to the solution, a 2N aqueous solution of sodium hydroxide (360 μl). The mixture was condensed under reduced pressure. To the residue, small amount of methanol and hexane (4 ml) were added. The mixture was filtered, and volatile matter was removed from the filtrate with vacuum pump overnight at room temperature and overnight at 80° C. to give the title compound (179 mg) having the following physical data:

TLC: Rf 0.33 (ethyl acetate: acetic acid: water=3: 1:1);

NMR: δ7.87(2H, d), 7.62(1H, dd), 6.98(2H, d), 6.86(1H, t), 6.71(1H, dd), 4.06(2H, t), 2.85(2H, t), 2.64(2H, s);

IR: ν3430, 2930, 1655, 1605, 1505, 1445, 1255 cm$^{-1}$;

Mass: m/e 452M+), 233;

Appearance: white powder.

EXAMPLE 10

Synthesis of 8-(p-octyloxybenzoyl)amino-2-(5-tetrazolyl)-1,4-benzodioxane-7-carboxylic acid

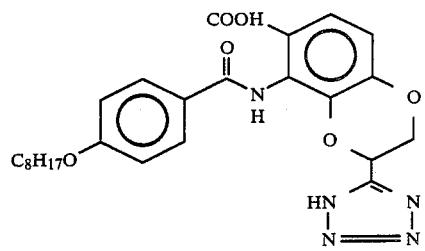

8-(p-octyloxybenzoyl)amino-2-(5-tetrazolyl)-1,4-benzodioxane-7-carboxylic acid methyl ester (332 mg; synthesized in example 2 (107) was dissolved in methanol (1.5 ml). To the solution, a 1N aqueous solution of sodium hydroxide (1.36 ml), and the mixture was stirred for 50 min at room temperature and for 2 hrs at 40° C. After cooling, 1N hydrochloric acid (2 ml) was added to the solution. The mixture was extracted with ethyl acetate. The extract was dried and concentrated under reduced pressure. The residue was purified by column chromatography on silica gel (chloroform: methanol=9:1) to give the title compound (263 mg) having the following physical data:

TLC: Rf 0.15 (chloroform: methanol=4:1);

NMR: δ8.00(2H, d), 7.68(1H, d), 6.98(2H, d), 6.82(1H, d), 6.04(1H, m), 4.56(2H, m), 4.03(2H, t), 1.82(2H, m), 1.31(10H, m), 0.88(3H, t);

IR: ν3600 –2300, 1680, 1640, 1600, 1490, 1460, 1250, 1170, 1080, 900, 840, 760 cm$^{-1}$;

Mass: m/e 495(M+), 477, 383, 233;

Appearance: pale brown powder.

EXAMPLE 11

Synthesis of 8-(p-pentylcinnamoyl)amino-2-(5-tetrazolyl)-6-methyl-1,4-benzodioxane sodium salt

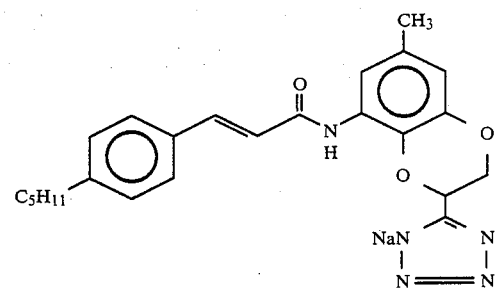

8-(p-pentylcinnamoyl)-2-(5-tetrazolyl)-6-methyl-1,4-benzodioxane (50 mg; synthesized in example 2 (103)) was dissolved in methanol (0.5 ml). To the solution, equivalent molar of a 1N aqueous solution of sodium hydroxide was added. The solution was stirred and then evaporated to dryness to give the title compound (51 mg).

EXAMPLE 11(1)

By the same procedure as example 11, corresponding salts of the compounds synthesized in examples (other than example 11 and esters) were given.

EXAMPLE 12

8-[p-(3E-hexenyloxy)benzoyl]amino-2-(5-tetrazolyl)-1,4-benzodioxane (0.5 g), cellulose calcium gluconate (200 mg; disintegrator), magnesium stearate (100 mg; lubricator) and microcrystalline cellulose (9.2 g) were admixed and punched out in conventional manner to give 100 tablets each containing 5 mg of the active ingredient.

What is claimed is:

1. A (fused)benz(thio)amide of the general formula:

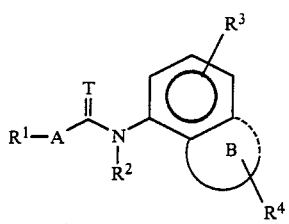

(I)

wherein

A represents a single bond or a methylene group, an ethylene group, a trimethylene group, a tetramethylene group, a vinylene group, a propenylene group, a butenylene group, a butadienylene group or an ethynylene group optionally substituted by one, two or three of straight or branched alkyl group(s) of from 1 to 10 carbon atom(s) and/or phenyl group(s);

B represents a group of general formula:

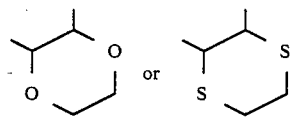

T represents an oxygen atom or a sulphur atom;
$R^1$ represents a group of general formula:

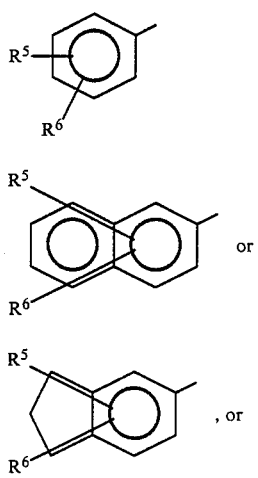

(iv) a straight or branched alkyl, alkenyl or alkynyl group of from 1 to 20 carbon atoms, wherein $R^5$ and $R^6$ independently represent a hydrogen atom or a halogen atom or a straight or branched alkyl, alkenyl or alkynyl group of up to 20 carbon atoms, one, two, three, four or five of the optional carbon atom(s) being unreplaced or replaced by one or more oxygen atom(s), sulphur atom(s), halogen atom(s), nitrogen atom(s), benzene ring(s), thiophene ring(s), naphthalene ring(s), carbocyclic ring(s), thiophene ring(s), naphthalene ring(s), carbocyclic (ring(s) of from 4 to 7 carbon atom(s), carbonyl group(s), carbonyloxy group(s), hydroxy group(s), carboxy group(s), azido group(s) and/or nitro group(s);

$R^2$ represents a hydrogen atom or a straight or branched alkyl group of from 1 to 6 carbon atom(s);

$R^3$ represents a hydrogen atom, a halogen atom, a hydroxy group, a nitro group, a group of general formula: —$COOR^7$, wherein $R^7$ represents a hydrogen atom or a straight or branched alkyl group of from 1 to 6 carbon atom(s), or a straight or branched alkyl, alkoxy or alkylthio group of from 1 to 6 carbon atom(s);

$R^4$ represents a group of general formula:

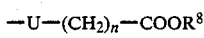

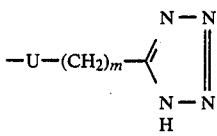

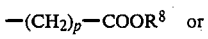

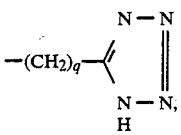

wherein U represents an oxygen atom or a sulphur atom, $R^8$ represents a hydrogen atom or a straight or branched alkyl group of from 1 to 6 carbon atoms(s), n and m represent an integer of from 1 to 10, respectively, and p and q represent zero or an integer of from 1 to 10, respectively or non-toxic salts thereof.

2. A compound according to claim 1, wherein B is 2,3,5,6-tetrahydro-1,4-dioxane ring (i.e. the formula:

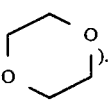

3. A compound according to claim 2, wherein A is a single bond, and the T is an oxygen atom.

4. A compound according to claim 3, wherein $R^1$ is a group of the general formula:

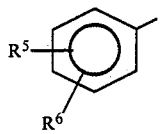

wherein R[5] and R[6] have the same meaning as in claim 1.

5. A compound according to claim 4, wherein R[5] is a hydrogen atom and R[6] is a hydrogen atom or a straight or branched alkyl group of from 1 to 20 carbon atom(s).

6. A compound according to claim 5, wherein the compound is selected from the group consisting of
8-(p-pentylbenzoyl)amino-2-(5-tetrazolyl)-1,4-benzodioxane,
8-(p-pentylbenzoyl)amino-2-(5-tetrazolyl)-6-chloro-1,4-benzodioxane,
8-(m-octylbenzoyl)amino-2-(5-tetrazolyl)-1,4-benzodioxane,
8-(o-pentylbenzoyl)amino-2-(5-tetrazolyl)-1,4-benzodioxane,
8-(p-butylbenzoyl)amino-2-(5-tetrazolyl)-1,4-benzodioxane,
8-(p-hexylbenzoyl)amino-2-(5-tetrazolyl)-1,4-benzodioxane,
8-(p-heptylbenzoyl)amino-2-(5-tetrazolyl)-1,4-benzodioxane,
8-(p-octylbenzoyl)amino-2-(5-tetrazolyl)-1,4-benzodioxane,
8-(p-nonylbenzoyl)amino-2-(5-tetrazolyl)-1,4-benzodioxane,
8-(p-decylbenzoyl)amino-2-(5-tetrazolyl)-1,4-benzodioxane,
8-(p-undecylbenzoyl)amino-2-(5-tetrazolyl)-1,4-benzodioxane and
8-(p-dodecylbenzoyl)amino-2-(5-tetrazolyl)-1,4-benzodioxane
and sodium salts thereof.

7. A compound according to claim 4, wherein R[5] is a hydrogen atom and R[6] is a straight or branched alkoxy group of from 1 to 19 carbon atom(s).

8. A compound according to claim 7, wherein the compound is selected from the group consisting of
8-(p-pentyloxybenzoyl)amino-2-(5-tetrazolyl)-1,4-benzodioxane,
8-(m-pentyloxybenzoyl)amino-2-(5-tetrazolyl)-1,4-benzodioxane,
8-(o-pentyloxybenzoyl)amino-2-(5-tetrazolyl)-1,4-benzodioxane,
8-(p-butyloxybenzoyl)amino-2-(5-tetrazolyl)-1,4-benzodioxane,
8-(p-nonyloxybenzoyl)amino-2-(5-tetrazolyl)-1,4-benzodioxane,
8-(p-propoxybenzoyl)amino-2-(5-tetrazolyl)-1,4-benzodioxane,
8-(p-hexyloxybenzoyl)amino-2-(5-tetrazolyl)-1,4-benzodioxane,
8-(p-heptyloxybenzoyl)amino-2-(5-tetrazolyl)-1,4-benzodioxane,
8-(p-octyloxybenzoyl)amino-2-(5-tetrazolyl)-1,4-benzodioxane,
8-(p-decyloxybenzoyl)amino-2-(5-tetrazolyl)-1,4-benzodioxane,
8-(p-isopentyloxybenzoyl)amino-2-(5-tetrazolyl)-1,4-benzodioxane,
8-(p-isohexyloxybenzoyl)amino-2-(5-tetrazolyl)-1,4-benzodioxane,
8-[p-(1-methylbutoxy)benzoyl]amino-2-(5-tetrazolyl)-1,4-benzodioxane,
8-[N-methyl-N-(p-octynyloxy)benzoyl]amino-2-(5-tetrazolyl)-1,4-benzodioxane,
8-(p-octyloxybenzoyl)amino-1,4-benzodioxane-2-carboxylic acid and methyl ester thereof,
8-(p-isoheptyloxybenzoyl)amino-2-(5-tetrazolyl)-1,4-benzodioxane,
8-(p-isooctyloxybenzoyl)amino-2-(5-tetrazolyl)-1,4-benzodioxane,
8-[p-(3,7-dimethyloctyloxy)benzoyl]amino-2-(5-tetrazolyl)-1,4-benzodioxane and
8-(p-octyloxybenzoyl)amino-2-(5-tetrazolyl)-1,4-benzodioxane-7-carboxylic acid and methyl ester thereof
and sodium salts thereof.

9. A compound according to claim 4, wherein R[5] is a hydrogen atom and R[6] is a straight or branched alkenyloxy group of from 3 to 19 carbon atoms.

10. A compound according to claim 9, wherein the compound is selected from the group consisting of
8-[p-(2E-octenyloxy)benzoyl]amino-2-(5-tetrazolyl)-1,4-benzodioxane,
8-[p-(3-butenyloxy)benzoyl]amino-2-(5-tetrazolyl)-1,4-benzodioxane,
8-[p-(3Z-hexenyloxy)benzoyl]amino-2-(5-tetrazolyl)-1,4-benzodioxane,
8-[p-(2Z-octenyloxy)benzoyl]amino-2-(5-tetrazolyl)-1,4-benzodioxane,
8-[p-(2E-nonenyloxy)benzoyl]amino-2-(5-tetrazolyl)-1,4-benzodioxane,
8-[N-methyl-N-[p-(2E-octenyloxy)benzoyl]amino]-2-(5-tetrazolyl)-1,4-benzodioxane,
8-[p-(2E-hexenyloxy)benzoyl]amino-2-(5-tetrazolyl)-1,4-benzodioxane,
8-[p-(3E-heptenyloxy)benzoyl]amino-2-(5-tetrazolyl)-1,4-benzodioxane,
8-[p-(2E-octenyloxy)benzoyl]amino-1,4-benzodioxane-2-carboxylic acid and methyl ester thereof,
8-[p-(2E-heptenyloxy)benzoyl]amino-2-(5-tetrazolyl)1,4-benzodioxane,
8-[p-(4-pentenyloxy)benzoyl]amino-2-(5-tetrazolyl)-1,4-benzodioxane,
8-[p-(2E-decenyloxy)benzoyl]amino-2-(5-tetrazolyl)-1,4-benzodioxane,
8-(p-geranyloxy benzoyl)amino-2-(5-tetrazolyl)-1,4-benzodioxane,
8-[p-(2E,7-octadienyloxy)benzoyl]amino-2-(5-tetrazolyl)-1,4-benzodioxane,
8-[p-(2E-pentenyloxy)benzoyl]amino-2-(5-tetrazoyl)-1,4-benzodioxane,
8-[p-(2E-butenyloxy)benzoyl]amino-2-(5-tetrazolyl)-1,4-benzodioxane,
8-[p-(3E-octenyloxy)benzoyl]amino-2-(5-tetrazolyl)-1,4-benzodioxane,
8-[p-(7-octenyloxy)benzoyl]amino-2-(5-tetrazolyl)-1,4-benzodioxane,
8-[p-(2E,4E-octadienyoxy)benzoyl]amino-2-(5-tetrazolyl)-1,4-benzodioxane and
8-[p-(2E-octenyloxy)benzoyl]amino-2-(5-tetrazolyl)-1,4-benzodioxane.
and sodium salts thereof.

11. A compound according to claim 4, wherein R[5] is a hydrogen atom and R[6] is a straight or branched alkynyloxy group of from 3 to 19 carbon atoms.

12. A compound according to claim 11, wherein the compound is selected from the group consisting of
8-[p-(2-octynyloxy)benzoyl]amino-2-(5-tetrazoyl)-1,4-benzodioxane, 8-[p-(2-octynyloxy)benzoyl]amino-1,4-benzodioxane-2-carboxylic acid and methyl ester thereof and
8-[p-(2-isooctynyloxy)benzoyl]amino-2-(5-tetrazolyl)-1,4-benzodioxane
and sodium salts thereof.

13. A compound according to claim 4, wherein $R^5$ is a hydrogen atom and $R^6$ is a straight or branched alkylthio group of from 1 to 19 carbon atom(s).

14. A compound according to claim 13, wherein the compound is selected from the group consisting of
8-(p-pentylthiobenzoyl)amino-2-(5-tetrazolyl)-1,4-benzodioxane,
8-(m-pentylthiobenzoyl)amino-2-(5-tetrazolyl)-1,4-benzodioxane,
8-(o-pentylthiobenzoyl)amino-2-(5-tetrazolyl)-1,4-benzodioxane and
8-(p-heptylthiobenzoyl)amino-2-(5-tetrazolyl)-1,4-benzodioxane
and sodium salts thereof.

15. A compound according to claim 4, wherein $R^5$ is a hydrogen atom and $R^6$ is a straight or branched alkoxy group of from 1 to 18 carbon atom(s) being substituted by halogen atom(s).

16. A compound according to claim 15, wherein the compound is selected from the group consisting of
8-[p-(6-chlorohexyloxy)benzoyl]amino-2-(5-tetrazolyl)-1,4-benzodioxane,
8-[p-(5-chloropentyloxy)benzoyl]amino-2-(5-tetrazolyl)-1,4-benzodioxane,
8-[p-(4-chlorobutoxy)benzoyl]amino-2-(5-tetrazolyl)-1,4-benzodioxane,
8[p-(7-chloroheptyloxy)benzoyl]amino-2-(5-tetrazolyl)-1,4-benzodioxane,
8-[p-(8-chlorooctyloxy)benzoyl]amino-2-(5-tetrazolyl)-1,4-benzodioxane,
8-[p-(9-chlorononyloxy)benzoyl]amino-2-(5-tetrazoyl)-1,4-benzodioxane and
8-[p-(5-bromopentyloxy)benzoyl]amino-2-(5-tetrazolyl)-1,4-benzodioxane-2-carboxylic acid and methyl ester thereof
and sodium salt thereof.

17. A compound according to claim 4, wherein $R^5$ is a hydrogen atom and $R^6$ is a straight or branched alkyloxyalkyl group of from 2 to 19 carbon atoms.

18. A compound according to claim 17, wherein the compound is 8-[p-(hexyloxymethyl)benzoyl]amino-2-(5-tetraxzolyl)-1,4-benzodioxane or sodium salt thereof.

19. A compound according to claim 4, wherein $R^5$ is a hydrogen atom and $R^6$ is a cycloalkyl group, cycloalkylalkyl group wherein the alkyl moiety is an alkyl group of from 1 to 8 carbon atom(s), or a cycloalkylalkyloxy group, wherein the alkyl moiety is an alkyl group of from 1 to 8 carbon atom(s), each of the groups represented by $R^6$ having from 4 to 7 carbon atoms which may be unsubstituted or substituted by a etraight or branched alkyl group of from 1 to 8 carbon atom(s).

20. A compound according to claim 19, wherein the compound is selected from the group consisting of
8-[p-(cyclohexylmethoxy)benzoyl]amino-2-(5-tetrazolyl)-1,4-benzodioxane,
8-[p-(4-cyclohexylbutoxy)benozyl ]amino-2-(5-tetrazolyl)-1,4-benzodioxane, and
8-[p-(2-cyclohexylethoxy)benzoyl]amino-2-(5-tetrazolyl)-1,4-benzodioxane
and sodium salts thereof.

21. A compound according to claim 4, wherein $R^5$ is a hydrogen atom and $R^6$ is a phenyl group, a phenylalkyl group wherein the alkyl moiety is an alkyl group of from 1 to 8 carbon atom(s), a phenylalkyloxy group wherein the alkyl moiety is an alkyl group of from 1 to 8 carbon atom(s), a phenylalkenyloxy group wherein the alkenyl moiety is an alkenyl group of from 2 to 8 carbon atoms, a naphthyl group, a naphthylalkyl group wherein the alkyl moiety is an alkyl group of from 1 to 8 carbon atom(s), a naphthylalkyloxy group wherein the alkyl moiety is an alkyl group of from 1 to 8 carbon atom(s), or a naphthylalkenyloxy group wherein the alkenyl moiety is an alkenyl group of from 2 to 8 carbon atoms which may be unsubstituted or substituted by a straight or branched alkyl group of from 1 to 8 carbon atom(s), one or more hydroxy group(s), one or more halogen atom(s) and/or one or more nitro group(s).

22. A compound according to claim 21, wherein the compound is selected from the group consisting of
8-[p-(p-butylphenyl)methoxybenoyl]amino-2-(5-tetrazolyl)-1,4-benzodioxane,
8-[p-(5-phenylpentyloxy)benzoyl]amino-2-(5-tetrazolyl)-1,4-benzodioxane,
8-[p-(3-phenylpropoxy)benzoyl]amino-2-(5-tetrazolyl)-1,4-benzodioxane,
8-[p-(p-propylphenyl)methoxybenzoyl]amino-2-(5-tetrazolyl)-1,4-benzodioxane,
8-[p-(3-phenyl-2-propenyloxy)benzoyl]amino-2-(5-tetrazolyl)-1,4-benzodioxane,
8-[p-(4-phenylbutoxy)benzoyl]amino-2-(5-tetrazolyl)-1,4-benzodioxane,
8-[p-(o-pentylphenyl)methoxybenzoyl amino-2-(5-tetrazolyl)-1,4-benzodioxane,
8-[p-(m-butylphenylmethoxybenzoyl]amino-2-(5-tetrazolyl)-1,4-benzodioxane,
8-(p-phenylmethoxybenzoyl)amino-2-(5-tetrazolyl)-1,4-benzodioxane,
8-[p-(2-phenylethoxy)benzoyl]amino-2-(5-tetrazolyl)-1,4-benzodioxane,
8-[p-(4-phenylbutoxy)benzoyl]amino-2-(5-tetrazolyl)-1,4-benzodioxane,
8-[p[-2-(2-naphthyl)ethoxy]benozxyl]amino-2-(5-tetrazolyl)-1,4-benzodioxane,
8-[p-[3-(p-chlorophenyl)propoxy]benzoyl]amino-2-(5-tetrazolyl)-1,4-benzodioxane and
8-[p-[4-(p-chlorophenyl)butoxy]benzoyl]amino-2-(5-tetraxzolyl)-1,4-benzodioxane
and sodium salts thereof.

23. A compound according to claim 4, wherein $R^5$ is a hydrogen atom and $R^6$ is a straight or branched alkoxy, alkenyloxy or alkoxyalkoxy group of from 1 to 18 carbon atom(s) in which one or more carbon atoms are replaced by one or more carbonyl group(s), carbonyloxyy group(s) or hydroxy group(s).

24. A compound according to claim 23, wherein the compound is selected from the group consisting of
8-[p-(5-methoxycarbonylpentyloxy)benzoyl]amino-2-(5-tetrazolyl)-1,4-benzodioxane,
8-[p-(6-acetyloxyhexyloxy)benzoyl]amino-2-(5-tetrazxolyl)-1,4-benzodioxane,
8-[p-(6-hydroxyhexyloxy)benzoyl]amino-2-(5-tetrazolyl)-1,4-benozdioxane,
8-[p-(2E-octenoyloxy)benzoyl]amino-2-(5-tetrazolyl)-1,4-benzodioxane and
8-(p-octanoylbenzoyl)amino-2-(5-tetrazolyl)-1,4-benzodioxane
and sodium salts thereof.

25. A compound according to claim 4, wherein $R^5$ is a hydrogen atom and $R^6$ is a straight or branched alkoxy group of from 1 to 17 carbon atom(s) which is substituted by a phenoxy or phenylthio group.

26. A compound according to claim 25, wherein the compound is selected form the group consisting of
8-[p-(3-phenylthiopropoxy)benzoyl]amino-2-(5-tetrazolyl)-1,4-benzodioxane,
8-[p-(3-phenoxypropoxy)benzoyl]amino-2-(5-tetrazolyl)-1,4-benzodioxane,
8-[p-(2-phenylthioethoxy)benzoyl]amino-2-(5-tetrazolyl)-1,4-benzodioxane and
8-[p-(2-phenoxyethoxy)benzoyl]amino-2-(5-tetraxrazolyl)-1,4-benzodioxane and sodium salts thereof.

27. A compound according to claim 4, wherein $R^5$ is a hydrogen atom and $R^6$ is a straight or branched alkoxy group of from 1 to 18 carbon atom(s) which is substituted by one or more thiophene ring(s).

28. A compound according to claim 27, wherein the compound is selected from the group consisting of
8-[p-[2-(3-thienyl)ethoxy]benzoyl]amino-2-(5-tetrazolyl)-1,4-benzodioxane and
8-[p-[4-(2-thienyl)butoxy]benzoyl]amino-2-(5-tetrazolyl)-1,4-benodioxane
and sodium salts thereof.

29. A compound according to claim 4, wherein $R^5$ is a hydrogen atom and $R^6$ is a straight or branched alkoxy group of from 1 18 carbon atom(s) which is substituted by one or more azido group(s), one or more nitro group(s) or one or more amino group(s) which may be unsubstituted or substituted by one or more straight or branched alkyl group(s) of from 1 to 6 carbon atom(s).

30. A compound according to claim 29, wherein the compound is selected from the group consisting of
8-[p-(5-azidopenyloxy)benozyl]amino-2-(5-tetrazolyl)-1,4-benzodioxane,
8-[p-(5-dimethylaminopentyloxy)benzoyl]amino-2-(5-tetrazolyl)-1,4-benzodioxane,
8-[p-(4-nitrobutoxy)benxzoyl amino-2-(5-tetrazolyl)-1,4-benzodioxane,
8-[p-(2-azidoethoxy)benzoyl]amino-2-(5-tetrazolyl)-1,4-benzodioxane and
8-[p-(4-azidobutoxy)benzoyl]amino-2-(5-tetrazolyl)-1,4-benzodioxane
and sodium salts thereof.

31. A compound according to claim 4, wherein $R^5$ is a hydrogen atom and $R^6$ is a straight, or branched alkyl, alkenyl, alkoxy or alkenyloxy group substituted by two kinds of groups i.e. carbonyl group(s) and amino group(s).

32. A compound according to claim 31 wherein the compound is 8-[p-(2-octenoylamino)benzoyl]amino-2-(5-tetrazolyl)-1,4-benzodioxane or sodium salt thereof.

33. A compound according to claim 4, wherein $R^5$ and $R^6$ are a halogen atom or a straight or branched alkyl, alkoxy or alkenyloxy group(s) of from 1 to 10 carbon atom(s), independently.

34. A compcund according to claim 33, wherein the compound is selected from the group consisting of
8-(p-pentyloxy-m-methoxybenzoyl)amino-2-(5-tetrazolyl)-1,4-benzodioxane and
8-[p-(2E-octenyloxy)-m-chlorobenzoy]amino-2-(5-tetrazolyl)-1,4-benzodioxane and sodium salts thereof.

35. A compound according to claim 3, wherein $R^1$ is a group of the general formula:

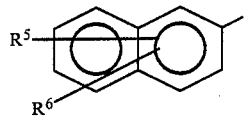

or

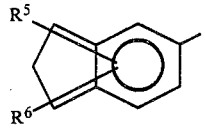

wherein $R^5$ and $R^6$ have the same meaning as set forth in claim 1.

36. A compound according to claim 35, wherein the compound is 8-(2-naphthylcarbonyl)amino-2-(5-tetrazolyl)-1,4-benzodioxane or sodium salt thereof.

37. A compound according to claim 2, wherein A is a vinylene group unsubstituted or substituted by straight or branched alkyl group(s) of from 1 to 6 carbon atom(s) or phenyl group(s) and T is an oxygen atom.

38. A compound according to claim 37, wherein in $R^1$ is a group of the general formula:

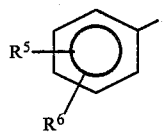

wherein $R^5$ and $R^6$ are the same meaning as set forth in claim 1.

39. A compound according to claim 38,
wherein $R^5$ is a hydrogen atom, and $R^6$ is a hydrogen atom or a straight or branched alkyl group of from 1 to 20 carbon atom(s).

40. A compound according to claim 39, wherein the compound is selected from the group consisting of
8-(p-pentylcinnamoyl)amino-2-(5-tetrazolyl)-1,4-benzodioxane,
8-(p-pentylcinnamoyl)amino-1,4-benzodioxane- 2-carboxylic acid and methyl ester thereof,
8-(p-heptylcinnamoyl)amino-2-(5-tetrazolyl)-1,4-benzodioxane,
8-[N-methyl-[N-(p-pentylcinnamoyl)]amino]-2-(5-tetrazolyl(-1,4-benzodioxane,
5-(p-pentylcinnamoyl)amino-2-(5-tetrazolyl)-7-chloro-1,4-benzodioxane,
8-(p-pentylcinnamoyl)amino-2-(5-tetrazolyl)-6-chloro-1,4-benzodioxane,
8-(p-ethylcinnamoyl)amino-2-(5-tetrazolyl)-1,4-benzodioxane,
8-(p-propylcinnamoyl)amino-2-(5-tetrazoyl)-1,4-benzodioxane,
8-(p-butylcinnamoyl)amino-2-(5-tetrazolyl)-1,4-benzodioxane,
8-(p-pentylcinnamoyl)amino-2-(5-tetrazolyl)-6-methyl-1,4-benzodioxane,
8-(o-pentylcinnamoyl)amino-2-(5-tetrazolyl)-1,4-benzodioxane,
8-(m-octylcinnamoyl)amino-2-(5-tetrazolyl)-1,4-benzodioxane,
8-(p-pentylcinnamoyl)amino-2-(5-tetrazoyl)-1,4-benzodioxane-5-carboxylic acid and methyl ester thereof, 5-(p-pentylcinnamoyl)amino-2-(5-tetrazolyl)-1,4-benzodioxane-8-carboxylic acid and methyl ester thereof,
8-(p-hexylcinnamoyl)amino-2-(5-tetrazolyl)-1,4-benzodioxane,
8-(p-nonylcinnamoyl)amino-2-(5-tetrazolyl)-1,4-benzodioxane,
8-(p-pentylcinnamoyl)amino-2-(5-tetrazolyl)-1,4-benzodioxane-6-carboxylic acid and methyl ester thereof,
5-(p-pentylcinnamoyl)amino-2-(5-tetrazolyl)-1,4-benzodioxane-7-carboxylic acid and methyl ester thereof,
8-(p-octylcinnamoyl)amino-2-(5-tetrazolyl)-1,4-benzodioxane,
8-(p-decylcinnamoyl)amino-2-(5-tetrazolyl)-1,4-benzodioxane,
8-(p-isopropylcinnamoyl)amino-2-(5-tetrazolyl)-1,4-benzodioxane,
8-(p-isobutylcinnamoyl)amino-2-(5-tetrazolyl)-1,4-benzodioxane,
8-(p-isopentylcinnamoyl)amino-2-(5-tetrazolyl)-1,4-benzodioxane,
8-(p-pentyl-2-methylcinnamoyl)amino-2-(5-tetrazolyl)-1,4-benzodioxane,
8-(p-pentyl-3-methylcinnamoyl)amino-2-(5-tetrazolyl)-1,4-benzodioxane and
8-(p-pentylcinnamoyl)amino-2-(5-tetrazolyl)methyl-1,4-benzodioxane
and sodium salts thereof.

41. A compound according to claim 38, wherein $R^5$ is a hydrogen atom, and $R^6$ is a straight or branched alkoxy group of from 1 to 19 carbon atom(s).

42. A compound according to claim 41, wherein the compound is selected from the group consisting of
8-(p-pentyloxycinnamoyl)amino-2-(5-tetrazolyl)-1,4-benzodioxane,
8-(m-pentyloxycinnamoyl)amino-2-(5-tetrazolyl(-1,4-benzodioxane,
8-(o-pentyloxycinnamoyl)amino-2-(5-tetrazolyl)-1,4-benzodioxane,
8-(p-propoxycinnamoyl)amino-2-(5-tetrazolyl)-1,4-benzodioxane,
8-(p-butoxycinnamoyl)amino-2-(5-tetrazolyl)-1,4-benzodioxane,
8-(p-octyloxycinnamoyl)amino-2-(5-tetrazolyl)-1,4-benzodioxane,
8-(p-hexyloxycinnamoyl)amino-2-(5-tetrazolyl(-1,4-benzodioxane,
8-(p-heptyloxycinnamoyl)amino-2-(5-tetrazolyl)-1,4-benzodioxane,
8-(p-isopentyloxycinnamoyl)amino-2-(5-tetrazolyl)-1,4-benzodioxane,
8-(p-isohexyloxycinnamoyl)amino-2-(5-tetrazolyl)-1,4-benzodioxane,
8-[p-(1-methylbutoxy)cinnamoyl]amino-2-(5-tetrazolyl)-1,4-benzodioxane,
8-(p-isoheptyloxycinnamoyl)amino-2-(5-tetrazolyl)-1,4-benzodioxane,
8-(p-isooctyloxycinnamoyl)amino-2-(5-tetrazolyl)-1,4-benzodioxane,
8-(p-isohexyloxy-2-methylcinnamoyl)amino-2-(5-tetrazolyl)-1,4-benzodioxane and
-8-(p-isohexyloxy-2-phenylcinnamoyl)amino-2-(5-tetrazolyl)-1,4-benzodioxane
and sodium salts thereof.

43. A compound according to claim 38,
wherein $R^5$ is a hydrogen atom, and $R^6$ is a straight or branched alkenyloxy group of from 3 to 19 carbon atoms.

44. A compound according to claim 43, wherein the compound is selected from the group consisting of
8-[p-(2E-octenyloxy)cinnamoyl]amino-2-(5-tetrazolyl)-1,4-benzodioxane,
8-[p-(2-propenyloxy)cinnamoyl]amino-2-(5-tetrazolyl)-1,4-benzodioxane,
8-[p-(3-butenyloxy)cinnamoyl]amino-2-(5-tetrazolyl)-1,4-benzodioxane,
8-[p-(3Z-hexenyloxy)cinnamoyl]amino-2-(5-tetrazolyl)-1,4-benzodioxane,
8-[p-(2Z-pentenyloxycinnamoyl]amino-2-(5-tetrazolyl)-1,4-benzodioxan,
8-[p-(2E-nonenyloxy)cinnamoyl]amino-2-(5-tetrazolyl)-1,4-benzodioxane,
8-[p-(3E-heptenyloxy)cinnamoyl]amino-2-(5-tetrazolyl)-1,4-benzodioxane,
8-[p-(2E-heptenyloxy)cinnamoyl]amino-2-(5-tetrazolyl)-1,4-benzodioxane,
8-[p-(2E-hexenyloxy)cinnamoyl]amino-2-(5-terrazolyl)-1,4-benzodioxane,
8-[p-(2E-pentenyloyy)cinnamoyl]amino-2-(5-tetrazolyl)-1,4-benzodioxane,
8-[p-(4-pentenyloxy)cinnamoyl]amino-2-(5-tetrazolyl)-1,4-benzodioxane,
8-[p-(2E-butenyloxy)cinnamoyl]amino-2-(5-tetrazolyl)-1,4-benzodioxane and
8-[p-(2E-decenyloxy)cinnamoyl]amino-2-(5-tetrazolyl)-1,4-benzodioxane
and sodium salts thereof.

45. A compound according to claim 38,
wherein $R^5$ is a hydrogen atom, and $R^6$ is a straight or branched alkynyloxy group of from 3 to 19 carbon atoms.

46. A compound according to claim 45, wherein the compound is selected from the group consisting of
8-[p-(2-octynyloxy)cinnamoyl]amino-2-(5-tetrazolyl)-1,4-benzodioxane and
8-[p-(2-pentynyloxy)cinnamoyl]amino-2-(5-tetrazolyl)-1,4-benzodioxane
and sodium salts thereof.

47. A compound according to claim 38,
wherein $R^5$ is a hydrogen atom, and $R^6$ is a straight or branched alkylthio group of from 1 to 19 carbon atom(s).

48. A compound according to claim 47, wherein the compound is selected from the group consisting of
8-(p-pentylthiocinnamoyl)amino-2-(5-tetrazolyl)-1,4-benzodioxane,
8(m-pentylthiocinnamoyl)amino-2-(5-tetrazolyl)-1,4-benzodioxane and
8-(o-pentylthiocinnamoyl)amino-2-(5-tetrazolyl)-1,4-benzodioxane
and sodium salts thereof.

49. A compound according to claim 38,
wherein $R^5$ is a hydrogen atom, and $R^6$ is a straight or branched alkoxy group of from 1 to 18 carbon atom(s) being substituted by halogen atom(s).

50. A compound according to claim 49, wherein the compound is selected from the group consisting of
8-[p-(6-chlorohexyloxy)cinnamoyl]amino-2-(5-tetrazolyl)-1,4-benzodioxane,
8-[p-(4-chlorobutoxy)cinnamoyl]amino-2-(5-tetrazolyl)-1,4-benzodioxane,
8-[p-(5-chloropentyloxy)cinnamoyl]amino-2-(5-tetrazolyl)-1,4-benzodioxane and
8-[p-(7-chloroheptyloxy)cinnamoyl]amino-2-(5-tetrazolyl)-1,4-benzodioxane
and sodium salts thereof.

51. A compound according to claim 38, wherein $R^5$ is a hydrogen atom, and $R^6$ is a straight or branched alkyloxyalkyl group of from 2 to 19 carbon atoms.

52. A compound according to claim 51,
wherein the compound is 8-(p-isopentyloxymethylcinnamoyl)amino-2-(5-tetrazolyl)-1,4-benzodioxane or sodium salt thereof.

53. A compound according to claim 38,
wherein $R^5$ is a hydrogen atom, and $R^6$ is a cycloalkyl, cycloalkylalkyl (wherein alkyl moiety is a group of from 1 to 8 carbon atom(s) or cycloalkylalkyloxy (wherein alkyl moiety is a group of from 1 to 8 carbon atom(s) of from 4 to 7 carbon atoms being unsubstituted or substituted by a straight or branched alkyl group of from 1 to 8 carbon atom(s).

54. A compound according to claim 53, wherein the compound is selected from the group consisting of
8-(p-cyclohexylcinnamoyl)amino-2-(5-tetrazolyl)-1,4-benzodioxane,
8-(p-cyclohexylmethoxycinnamoyl)amino-2-(5-tetrazolyl)-1,4-benzodioxane,
8-[p-(4-cyclohexylbutoxy)cinnamoyl]amino-2-(5-tetrazolyl)-1,4-benzodioxane and
8-[p-(2-cyclohexylethoxy)cinnamoyl]amino-2-(5-tetrazolyl)-1,4-benzodioxane
and sodium salts thereof.

55. A compound according to claim 38, wherein $R^5$ is a hydrogen atom, and $R^6$ is a phenyl group, a phenylalkyl group wherein the alkyl moiety is an alkyl group of from 1 to 8 carbon atom(s), a phenylalkyloxy group whereien the alkyl moiety is an alkyl group of from 1 to 8 carbon atom(s) or a phenylakenyloxy group wherein the alkenyl moiety is an alkenyl group of from 2 to 8 carbon atoms, which may be unsubstituted or substituted by one or more straight or branched alkyl group(s) of from 1 to 8 carbon atom(s), one or moe hydroxy group(s), one or more halogen atom(s) and/or one or more nitro group(s).

56. A compcund according to claim 55, wherein the compound is selected from the group consisting of
8-(p-phenylmethylcinnamoyl)amino-2-(5-tetrazolyl)-1,4-benzodioxane,
8-(p-phenylmethoxycinnamoyl)amino-2-(5-tetrazolyl)-1,4-benzodioxane,
8-[p-(2-phenylethoxy)cinnamoyl]amino-2-(5-tetrazolyl)-1,4-benzodioxane,
8-[p-(4-phenylbutoxy)cinnamoyl]amino-2-(5-tetrazolyl)-1,4-benzodioxane,
8-[p-(5-phenylpentyloxy)cinnamoyl]amino-2-(5-tetrazolyl)-1,4-benzodioxane and
8-[p-(3-phenylpropoxy)cinnamoyl]amino-2-(5-tetrazolyl)-1,4-benzodioxane
and sodium salts thereof.

57. A compound according to claim 38,
wherein $R^5$ is a hydrogen atom, and $R^6$ is a straight or alkoxy, alkenyloxy or alkoxyalkoxy group of from 1 to 18 carbon atoms(s) in which one or more carbon atoms are replaced by one or more carbonyl group(s), carbonyloxy group(s) or hydroxy group(s).

58. A compound according to claim 57,
wherein the compound is 8-[p-(6-acetyloxyhexyloxy)cinnamoyl]amino-2-(5-tetrazolyl)-1,4-benzodioxane or sodium salts thereof.

59. A compound according to claim 38,
wherein $R^5$ is a hydrogen atom, and $R^6$ is a straight or branched alkoxy group of from 1 to 18 carbon atom(s) which is substituted by thiophene ring(s).

60. A compound according to claim 59,
wherein the compound is 8-[p-[2-(2-thienyl)ethoxy]cinnamoyl]-amino-2-(5-tetrazolyl)-1,4-benzodioxane or sodium salts thereof.

61. A compound according to claim 38, wherein $R^5$ and $R^6$ are a halogen atom or a straight or branched alkyl, alkoxy or alkenyloxy group of from 1 to 10 carbon atom(s), independently.

62. A compound according to claim 61, wherein the compound is selected from the group consisting of
8-(m,p-dimethoxycinnamoyl)amino-2-(5-tetrazolyl)-1,4-benzodioxane,
8-(m-methoxy-p-pentyloxycinnamoyl)amino-2-(5-tetrazolyl)-1,4-benzodioxane and
8-(p-pentyloxy-m-chlorocinnamoyl)amino-2-(5-tetrazoylyl)-1,4-benzodioxane
and sodium salts thereof.

63. A compound according to claim 37, wherein $R^1$ is a group of the general formula:

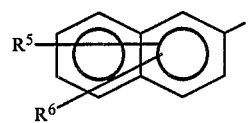

or

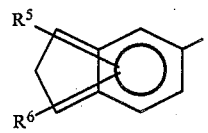

(wherein $R^5$ and $R^6$ have the same meaning as set forth in claim 1.

64. A compound according to claim 63,
wherein the compound is 8-[3-(5-indanyl)acryloyl]amino-2-(5-tetrazolyl)-1,4-benzodioxane or scdium salt thereof.

65. A compound according to claim 37, wherein $R^1$ is a straight or branched alkyl, alkenyl or alkynyl group of from 1 to 20 carbon atom(s).

66. A compound according to claim 65,
wherein the compound is N-(2-hexadecenoyl)amino-2-(5-tetrazolyl)-1,4-benzodioxane or sodium salt thereof.

67. A compound according to claim 2, wherein A is a methylene or ethylene group, and symbol T is an oxygen atom.

68. A compound according to claim 67, wherein the compound is selected from the group consisting of
8-(p-pentylphenylacetyl)amino-2-(5-tetrazolyl)-1,4-benzodioxane and
8-[3-(p-pentylphenyl)propionyl]amino-2-(5-tetrazolyl)-1,4-benzodioxane
and sodium salts thereof.

69. A compound according to claim 2, wherein A is an ethynylene or butadienylene group, and T is an oxygen atom.

70. A compound according to claim 69, wherein the compound is selected from the group consisting of
8-(p-hexylphenylpropioloyl)amino-2-(5-tetrazolyl)-1,4-benzodioxane, 8-[5-(p-propoxyphenyl)penta-2E,4E-dienoyl]amino-2-(5-tetrazolyl)-1,4-benzodioxane and
8-[5-(p-butylphenyl)penta-2E,4E-dienoyl]amino-2-(5-tetrazolyl)-1,4-benzodioxane
and sodium salts thereof.

71. A compound according to claim 2, wherein A is a single bond or vinylene group, and T is a sulphur atom.

72. A compound according to claim 71, wherein the compound is 8-(p-heptyloxybenzothioyl)amino-2-(5-tetrazolyl)-1,4-benzodioxane or sodium salt thereof.

73. A compound according to claim 1, wherein B is a 2,3,5,6-tetrahydro-1,4-dithiane ring (i.e. the formula:

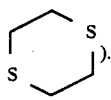
).

74. A compound according to claim 73, wherein A is a single bond or vinylene group which may be unsubstituted or substituted by one or more straight or branched alkyl group(s) of from 1 to 6 carbon atom(s) or one or more phenyl group(s) and T is an oxygen atom.

75. A compound according to claim 74, wherein $R^1$ is a group of the general formula:

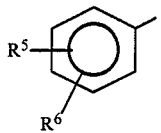

wherein $R^5$ and $R^6$ have the same meaning as set forth in claim 1.

76. A compound according to claim 75, wherein the compound is selected from the group consisting of
8-(p-pentylcinnamoyl)amino-2-(5-tetrazolyl)-2,3-dihydro-14-dithianaphthalene and
5-(p-pentylcinnamoyl)amino-2-(5-tetrazolyl)-2,3-dihydro-1,4-dithianaphthalene
and sodium salts thereof.

77. A pharmaceutical composition which contains, as an active ingredient, at least one compound of the general formula (I) as defined in claim 1, together with a pharmaceutically acceptable carrier and/or coating.

* * * * *

UNITED STATES PATENT AND TRADEMARK OFFICE
CERTIFICATE OF CORRECTION

PATENT NO.   : 4847,275
DATED        : July 11, 1989
INVENTOR(S)  : Masaaki Toda, Tumoru Miyamoto and Yoshinobu Arai It is certified that error appears in the above-identified patent and that said Letters Patent is hereby corrected as shown below:

On the Title page,
Item [30], Foreign Application Priority data, delete

"Dec. 20, 1984" and "Dec. 22, 1984" and insert

--Nov. 20, 1984-- and --Nov. 22, 1984--, respectively.

Signed and Sealed this

Fifteenth Day of June, 1993

Attest:

MICHAEL K. KIRK

Attesting Officer    Acting Commissioner of Patents and Trademarks